(12) United States Patent
Ozcelik et al.

(10) Patent No.: US 11,098,203 B2
(45) Date of Patent: Aug. 24, 2021

(54) POLYMER COATINGS

(71) Applicant: COMMONWEALTH SCIENTIFIC AND INDUSTRIAL RESEARCH ORGANISATION, Acton (AU)

(72) Inventors: Berkay Ozcelik, Dingley Village (AU); Helmut Werner Thissen, Rowville (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 0 days.

(21) Appl. No.: 16/334,650

(22) PCT Filed: Aug. 30, 2017

(86) PCT No.: PCT/AU2017/050927
§ 371 (c)(1),
(2) Date: Mar. 19, 2019

(87) PCT Pub. No.: WO2018/039721
PCT Pub. Date: Mar. 8, 2018

(65) Prior Publication Data
US 2019/0225817 A1 Jul. 25, 2019

(30) Foreign Application Priority Data
Aug. 31, 2016 (AU) ................ 2016903477

(51) Int. Cl.
*A61L 27/34* (2006.01)
*C09D 5/16* (2006.01)
(Continued)

(52) U.S. Cl.
CPC .......... *C09D 5/1662* (2013.01); *A61L 17/145* (2013.01); *A61L 27/18* (2013.01);
(Continued)

(58) Field of Classification Search
None
See application file for complete search history.

(56) References Cited

U.S. PATENT DOCUMENTS 5,182,317 A * 1/1993 Winters .............. A61L 33/0029
523/112
7,883,694 B2 * 2/2011 Rhee ........................ C08H 1/00
424/78.3
(Continued)

FOREIGN PATENT DOCUMENTS

WO 2006/121937 A1 11/2006
WO 2007/085042 A1 8/2007
(Continued)

OTHER PUBLICATIONS

Environmentally friendly processing of thermosets by two-stage sequential aza Michael addition and free radical polymerization of amine acrylate mixtures, Gonzalez et al. Polymer Chem., 2015, 6, 6987 (Year: 2015).*
(Continued)

*Primary Examiner* — Peter A Salamon
(74) *Attorney, Agent, or Firm* — Merchant & Gould P.C.

(57) ABSTRACT

The application is directed to polymer coatings which can be modified to control biointerfacial interactions including biofilm formation and protein adsorption onto said coatings. The polymer coatings comprise a First Component comprising epoxide or alkenyl groups, and a Second Component comprising at least one amine group. The polymer coatings further comprise at least one bioactive agent which may control said biofilm formation and/or protein adsorption. Also disclosed herein are methods for producing said coatings incorporating bioactive molecules in one or two step procedures on a substrate. The polymer coating may be immobilised on the substrate via the reaction of functional groups present on the First Component and/or Second
(Continued)

Component with complimentary functional groups disposed on at least one surface of the substrate.

13 Claims, 22 Drawing Sheets

(51) Int. Cl.

| | | |
|---|---|---|
| *A61L 17/14* | (2006.01) | |
| *A61L 29/08* | (2006.01) | |
| *C08G 59/50* | (2006.01) | |
| *C08G 59/18* | (2006.01) | |
| *A61L 27/18* | (2006.01) | |
| *A61L 29/06* | (2006.01) | |
| *A61L 29/16* | (2006.01) | |
| *A61L 27/54* | (2006.01) | |
| *C09D 163/00* | (2006.01) | |
| *C09D 133/26* | (2006.01) | |
| *C09D 171/00* | (2006.01) | |

(52) U.S. Cl.
CPC ............... *A61L 27/34* (2013.01); *A61L 27/54* (2013.01); *A61L 29/06* (2013.01); *A61L 29/085* (2013.01); *A61L 29/16* (2013.01); *C08G 59/18* (2013.01); *C08G 59/184* (2013.01); *C08G 59/50* (2013.01); *C09D 5/1637* (2013.01); *C09D 133/26* (2013.01); *C09D 163/00* (2013.01); *C09D 171/00* (2013.01); *A61L 2300/404* (2013.01)

(56) References Cited

U.S. PATENT DOCUMENTS

| | | | | |
|---|---|---|---|---|
| 2002/0068157 | A1* | 6/2002 | Wischerhoff | .... G01N 33/54353 428/212 |
| 2004/0246321 | A1* | 12/2004 | Takashima | .............. C09D 11/40 347/100 |
| 2005/0031793 | A1* | 2/2005 | Moeller | ............... C09D 201/02 427/384 |
| 2008/0003259 | A1* | 1/2008 | Salamone | ................ A61L 27/34 424/427 |
| 2009/0155335 | A1 | 6/2009 | O'Shaughnessey et al. | |
| 2010/0145286 | A1 | 6/2010 | Zhang et al. | |
| 2012/0277719 | A1* | 11/2012 | Shukla | ................. A61L 26/0038 604/500 |
| 2013/0190890 | A1* | 7/2013 | Shah | ........................ A61L 27/34 623/23.56 |
| 2013/0302401 | A1* | 11/2013 | Ma | ........................... A61L 31/10 424/450 |
| 2019/0225817 | A1* | 7/2019 | Ozcelik | .................... A61L 27/18 |

FOREIGN PATENT DOCUMENTS

| | | | |
|---|---|---|---|
| WO | 2010/065960 | A2 | 6/2010 |
| WO | 2016/048155 | A1 | 3/2016 |
| WO | WO-2016048155 | A1 * | 3/2016 ............. A61L 27/18 |

OTHER PUBLICATIONS

Extended European Search Report for corresponding European Patent Application No. 17844683.7 dated Apr. 28, 2020, 9 pages.
International Search Report and Written Opinion of the International Searching Authority for International Patent Application No. PCT/AU2017/050927 dated Nov. 13, 2017, 14 pages.
Gonzalez, G. et al., "Environmentally-friendly processing of thermosets by two-stage sequential aza-Michael addition and free-radical polymerization of amine-acrylate mixtures", Polym. Chem., 6: 6987-6997 (2015).
Mondrzyk, A. et al., "Antibacterial materials: structure-bioactivity relationship of epoxy-amine resins containing quaternary ammonium compounds covalently attached", Polym. Int., 63: 1192-1196 (2014).
Barraud, N. et al., "Involvement of Nitric Oxide in Biofilm Dispersal of Pseudomonas aeruginosa", Journal of bacteriology, 188: 7344-7353 (2006).
Chen, R. et al., "Synthesis, characterization and in vitro activity of a surface-attached antimicrobial cationic peptide", Biofouling, 25(6): 517-524 (2009).
Chen, R. et al., "Characterization of chemoselective surface attachment of the cationic peptide melimine and its effects on antimicrobial activity", Acta Biomaterialia, 8: 4371-4379 (2012).
Coad, B. et al., "A substrate-independent method for surface grafting polymer layers by atom transfer radical polymerization; Reduction of protein adsorption", Acta Biomaterialia, 8: 608-618 (2012).
Gong, C. et al., "Biodegradable In Situ Gel-Forming Controlled Drug Delivery System Based on Thermosensitive PCL-PEG-PCL Hydrogel: Part 1—Synthesis, Characterization, and Acute Toxicity Evaluation", J. Pharm. Sci., 98(12): 4684-4694 (2009).
Ho, K. et al., "Quorum sensing inhibitory activies of surface immobilized antibacterial dihydropyrrolones via click chemistry", Biomaterials, 35: 2336-2345 (2014).
Ho, K. et al., "Charterisation and in vitro activities of surface attached dihydropyrrol-2-ones against Gram-Negative and Gram-positive bacterial", Biofouling, 26: 913-921 (2010).
Kirov, S. et al., "Biofilm differentiation and dispersal in mucoid Pseudomonas aeruginosa isolates from patients with cystic fibrosis", Microbiology, 153: 3264-3274 (2007).
Li, B. et al., "Systemic toxicity and toxicokinetics of a high dose of polyethylene glycol 400 in dogs following intravenous injection", Drug and Chem. Toxicol., 34: 208-212 (2011).
Lowe, A., "Thiol-ene "click" reactions and recent applications in polymer and materials synthesis", Polymer Chemistry, 1: 17-36 (2010).
Moad, G. et al., "Living Radical Polymerization by the RAFT Process", Aust. J. Chem., 58: 379-410 (2005).
Ozcelik, B. et al., "Biodegradable and Biocompatible Poly(Ethylene Glycol)-based Hydrogel Films for the Regeneration of Corneal Endothelium", Adv. Healthcare Mater., 3: 1496-1507 (2014).
Riches, A. et al., "Scalable synthesis of an integrin-binding peptide mimetic for biomedical applications", Tetrahedron, 68: 9448-9455 (2012).
Willcock, H. et al., "End group removal and modification of RAFT polymers", Polym. Chem., 1: 149-157 (2010).

* cited by examiner

POLYMER COATINGS

CROSS-REFERENCE TO RELATED APPLICATIONS

This application is a National Stage Application of PCT/AU2017/050927, filed on 30 Aug. 2017, which claims benefit of Australian Provisional Patent Application No 2016903477, filed on 31 Aug. 2016, and which applications are incorporated herein by reference. To the extent appropriate, a claim of priority is made to each of the above disclosed applications.

TECHNICAL FIELD

The present disclosure is directed to polymer coatings which can be modified to control biointerfacial interactions including biofilm formation and protein adsorption onto said coatings. Also disclosed herein are methods for producing said coatings incorporating bioactive molecules in one or two step procedures.

BACKGROUND

The ability to control the biological response to material surfaces effectively is of interest in a wide range of biomedical applications, such as biosensors, cell culture tools and implantable medical devices. Biological responses that are of particular interest include non-specific interactions such as protein adsorption and biofouling, mammalian cellular responses (including attachment, growth and differentiation), and also microbial attachment and biofilm formation. Undesired non-specific interactions between biology and synthetic implantable device surfaces have been demonstrated to be the underlying cause for many adverse clinical events such as infection, inflammation, and implant encapsulation, which can limit the performance of devices and can result in their failure. The successful control over these non-specific interactions in turn can provide the opportunity to display bioactive signals on surfaces that lead to exclusively specific biointerfacial interactions.

Cell attachment to a material surface is mediated by proteins and other biomolecules that adsorb onto synthetic surfaces within seconds once the material comes in to contact with body fluids or a cell culture medium. Therefore, non-specific protein adsorption and cell attachment are interrelated. A similar relationship exists between non-specific protein adsorption and the initial phase of microbial attachment. Polymer based coatings can be tailored for the effective reduction of non-specific protein/biomolecule adsorption and subsequent events such as cell attachment and microbial attachment.

Immobilisation of specific bioactive signals displayed on low-fouling coatings can also be used to combat bacterial colonisation of surfaces. For example, integrin-binding peptides or peptide mimetics such as the antimicrobial peptides (AMPs) act by disrupting bacterial cell membranes via direct interaction with the lipid bilayer structure. While antibiotics target specific cellular activities and the numbers of antibiotic resistant bacteria are on the rise, the direct targeting of membranes by AMPs makes it very difficult for bacteria to develop complete resistance. Although there are concerns regarding adverse effects towards mammalian cells, synthetic AMPs can potentially overcome these issues. An example is melimine, which is a synthetic peptide derived from portions of the cationic peptides melittin and protamine, demonstrating broad spectrum antimicrobial capabilities while being non-cytotoxic and non-haemolytic at therapeutic levels. Additionally, melimine retains its antimicrobial properties even when immobilised onto surfaces both in vitro and in vivo.

The concept of immobilising bioactive signals, such as peptides, to influence specific biointerfacial interactions and in some cases prevent non-specific interactions on a background coating, is considered to be important for biomedical applications. Of significant interest is the application of such coatings for antimicrobial purposes. As the struggle between host tissue integration and bacterial colonisation on medical device surfaces becomes much more competitive with the increasing use of implants, it is imperative that the device surface provides maximum resistance capabilities towards biofilm formation. For many people suffering from disease, trauma or old age, the development of implantable medical devices has greatly improved their quality of life. On the other hand, these devices have also introduced new medical challenges. In particular, device related infections have emerged as an increasingly significant problem. These infections, if not prevented or treated can lead to significant morbidity and mortality. Unfortunately, while alleviating one problem, an implanted medical device also presents a surface for bacteria to attach and proliferate, leading to the formation of biofilm communities, which are exceedingly difficult to extinguish once they are established.

Although both low fouling coatings and bactericidal coatings, including silver releasing surfaces, show promising outcomes in regard to reducing biofilm formation, there is broad agreement that multifunctional coatings that display multiple layers of defence, such as low-fouling characteristics combined with the display of AMPs, will lead to improved outcomes. However, to date it is difficult to achieve this in a simple one-step procedure, and the complexity of many coating strategies has prevented their translation into biomedical products.

Another attractive strategy is the exploitation of the communication between bacteria known as quorum sensing (QS). QS is a mechanism employed by bacteria that utilises chemical signalling to coordinate bacterial communities to alter their collective behaviour. A number of naturally occurring halogenated furanone compounds, also known as fimbrolides produced by the Australian red alga (Delisea pulchra), have been identified to disrupt the QS mechanism of several bacteria. The downside of naturally occurring fimbrolides is that most of them are cytotoxic towards mammalian cells. In order to address this problem, alternative compounds, such as 1, 5-dihydropyrrol-2-one based compounds, can be utilised. These compounds demonstrate excellent antimicrobial properties while maintaining low cytotoxicity towards mammalian cells.

Furthermore, with the increasing use of implants to alleviate tissue dysfunction, trauma and disease, it is imperative that device surfaces provide maximum resistance capabilities towards biofilm formation to minimise associated bacterial infections. Although both low fouling coatings and bactericidal coatings, including silver releasing surfaces, show promising outcomes in regard to reducing biofilm formation, only the development of multifunctional coatings that display multiple defence mechanisms, such as low-fouling characteristics combined with the display of surface active antimicrobials will lead to more versatile ways to combat biofilm formation and improved outcomes.

While there is a broad commercial interest in coatings that combine multiple defence mechanisms to provide protection against biofilm formation, there is also resistance against complex coatings where parameters are difficult to control.

Furthermore, the biomedical industry is particularly conservative and cost conscious, leading to a high barrier to adoption of new or improved materials and change. Therefore, new and improved coatings should preferably combine high effectiveness in regards to performance with simplicity and easy-to-control processing parameters in regard to the application of the coating. Conversely, a highly effective coating produced using commercially available precursors applied via conventional coating methods (e.g., spray coating, dip coating, solvent casting) in one or two steps is highly attractive in regard to commercial translation.

In addition, there is a real need to make coatings simply and cheaply. Many manufacturers are reluctant to replace conventional coatings, which have been shown to be effective, with new functionally sophisticated ones that are complex to make. In order to overcome the barriers and resistance to new technology, one catalyst to change is to provide facile, simple methods to produce the new coatings, avoiding the need for detailed and complicated synthetic methodologies.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

Disclosed herein is a versatile platform coating made via a simple process which can be applied to substrate materials using commercially available precursors via a solvent system. Various bioactive agents, such as peptides, and compounds that disrupt the QS mechanism of bacteria, may be incorporated into the coatings via one or two-step procedures while retaining their biological activity.

Preferred aims of the present disclosure are to provide one or two step process for forming coatings, and outlining facile methods for covalently incorporating of a broad range of bioactive compounds. These methods allow highly effective control over biological responses due to a combinatorial effect of low fouling and bioactive coating components. In addition the methods can exhibit excellent control over the concentration/density of bioactive compounds—for example, to increase the density of bioactive compounds bound to a substrate surface—this is very difficult to achieve with conventional bioactive coating methods.

The present invention aims to provide an advantage in relation to existing technologies. For example, the methods outlined herein may be performed in the absence of a vacuum or an inert environment. The methods and processes outlined herein may, for example be water-based. Further advantages can potentially also include: very little or no waste material generated via the adoption of the disclosed methods; the desired coating composition may be easily tailored for different applications; and/or the process may be easily translated to current commercial coating processes.

Furthermore, the polymer coatings defined herein may be produced from commercially available precursors. In addition, the synthetic steps required for the formation of the polymer coatings may not require the presence of a catalyst or an oxygen free environment.

The methods outlined herein allow a bioactive agent to be incorporated into a polymer coating as described herein, in either a single one-step process, or in a two-step process.

Preferably the bioactive agent is incorporated into a polymer coating in a one-step process.

In addition, the polymer coatings disclosed herein may show anti-fouling properties.

Furthermore, the polymer coatings disclosed herein may show antimicrobial properties.

The reduction of non-specific interactions and the provision of low protein fouling surfaces is a desired feature in controlling biointerfaces for applications including antimicrobial coatings, since it can act as a first layer of defence by resisting bacterial attachment.

The simple and effective coating platform disclosed herein can provide access to a broad range of biologically active surfaces for a number of biomedical devices where effective control over biointerfacial interactions is required.

In a first aspect, disclosed herein is a method for coating a substrate on at least one surface of the substrate, the method comprising:
a) providing:
   a First Component comprising at least two epoxide groups or at least two alkenyl groups;
   a Second Component comprising at least one amine group; and
b) forming a covalently crosslinked polymer coating with the First Component and the Second Component, the polymer coating being immobilised on the substrate,
wherein at least one bioactive agent comprising at least one suitable reactive group for incorporation into the covalently crosslinked polymer coating is introduced prior to, during or after the formation of the covalently crosslinked polymer.

In one embodiment of the first aspect, the at least one bioactive agent comprising at least one suitable reactive group for incorporation into the covalently crosslinked polymer coating is introduced in step a).

In a second aspect, disclosed herein is a composition produced by the method according to the first aspect.

In a third aspect, disclosed herein is a composition comprising:
a substrate;
a crosslinked polymer coating which is immobilised on the substrate, wherein the crosslinked polymer coating is formed from:
a First Component comprising at least two epoxide groups or at least two alkenyl groups;
a Second Component comprising at least one amine group; and
at least one bioactive agent.

In a fourth aspect, disclosed herein is a composition consisting essentially of:
a substrate;
a crosslinked polymer coating which is immobilised on the substrate via functional groups present on a surface of the substrate, wherein the crosslinked polymer coating is formed from:
a First Component comprising at least two epoxide groups or at least two alkenyl groups;
a Second Component comprising at least one amine group; and
at least one bioactive agent.

In a fifth aspect, disclosed herein is use of a composition according to the second, third or fourth aspect, as an antimicrobial coating.

In a sixth aspect, disclosed herein is use of a composition according to the second, third or fourth aspect, as an antifouling coating.

In a seventh aspect, disclosed herein is use of a composition according to the second, third or fourth aspect, for coating a substrate wherein the substrate is in the form of a medical device to which the composition is applied as a coating.

In an eighth aspect, disclosed herein is use of a composition according to the second, third or fourth aspect, for coating a substrate wherein the substrate is in the form of a medical device to which the composition is applied as a coating, wherein the medical device is selected from the group consisting of: surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronisation therapy devices, ventricular assist devices, heart valves, catheters including vascular, urinary, neurological, peritoneal, and interventional catheters, shunts, wound drains, dialysis membranes, infusion ports, cochlear implants, endotracheal tubes, guide wires, fluid collection bags, sensors, wound treatments including dressings, bandages, sutures, cell scaffolds, bone cements and particles, ophthalmic devices, orthopaedic devices including hip implants, knee implants, spinal implants, screws, plates, rivets, rods, intramedullary nails, bone cements, artificial tendons, and other prosthetics or fracture repair devices, dental implants, breast implants, penile implants, maxillofacial implants, cosmetic implants, valves, appliances, scaffolding, suturing material, needles, hernia repair meshes, tension-free vaginal tape and vaginal slings, tissue regeneration and cell culture devices.

BRIEF DESCRIPTION OF DRAWINGS

Embodiments of the invention will now be described, by way of example only, with reference to the accompanying figures:

FIG. 1 shows polymer casting on a surface and with an exemplified crosslink-coating on the surface. Substituent "X" is a functional group, for example $NH_2$, OH or COOH.

In FIG. 12: 1=ALAPP; 2=ALAPP-DHP; 3=$^{1:1}$PEGDAP; 4=$^{1:1}$PEGDAP-DHP-OS$_3$; 5=$^{1:1}$PEGDAP-DHP-OS$_{1.5}$; 6=$^{1:1}$PEGDAP-DHP-ITS$_3$; 7=$^{1:1}$PEGDAP-DHP-DTS$_3$; 8=ALAPP; 9=ALAPP-DHP; 10=$^{2:1}$PEGDAP; 11=$^{2:1}$PEGDAP-DHP-OS$_3$; 12=$^{2:1}$PEGDAP-DHP-OS$_{1.5}$; 13=$^{2:1}$PEGDAP-DHP-ITS$_3$; and 14=$^{2:1}$PEGDAP-DHP-DTS$_3$.

DESCRIPTION OF EMBODIMENTS

Terms and Definitions

Figure 1:
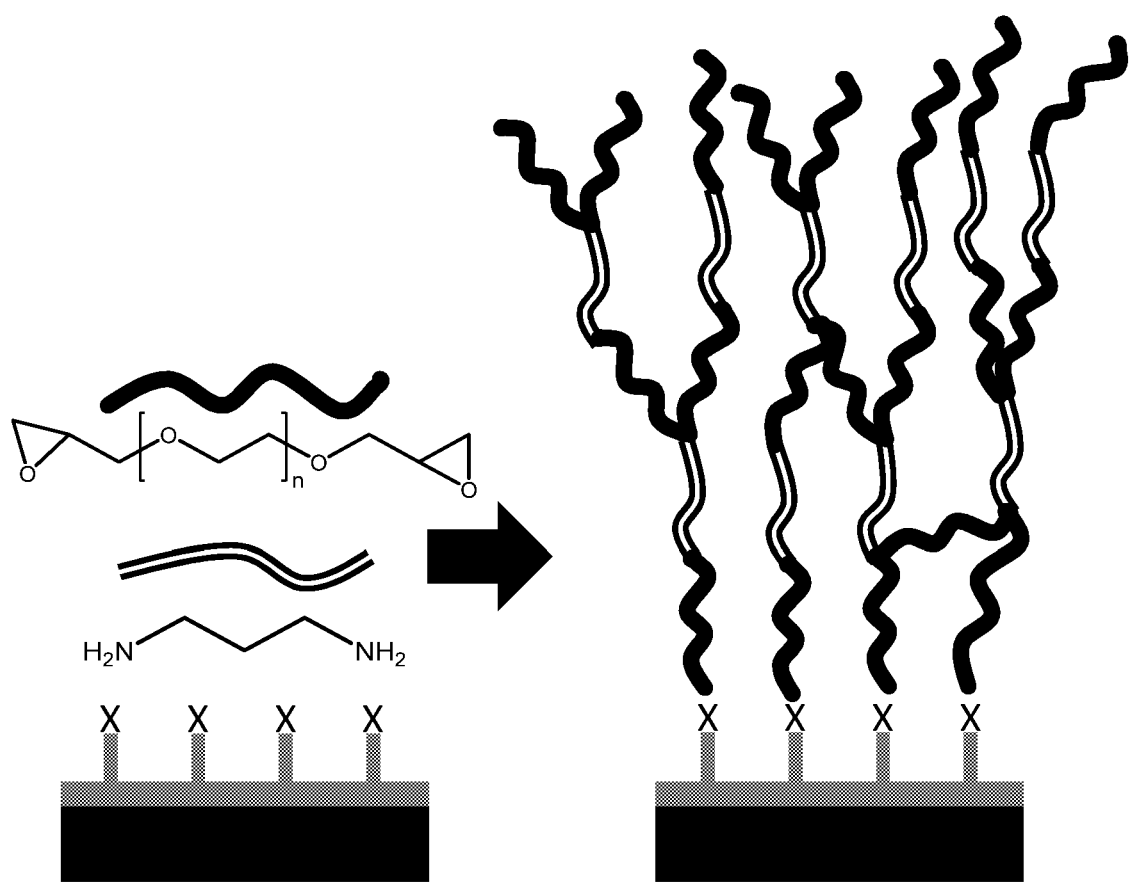
FIG. 1—Preparation of a poly(ethylene glycol) diglycidyl ether (PEGDGE) and 1,3-diaminopropane (DAP) coating.

With regards to the definitions provided herein, unless stated otherwise, or implicit from context, the defined terms and phrases include the provided meanings. Unless explicitly stated otherwise, or apparent from context, the terms and phrases below do not exclude the meaning that the term or phrase has acquired by a person skilled in the relevant art. The definitions are provided to aid in describing particular embodiments, and are not intended to limit the claimed invention, because the scope of the invention is limited only by the claims. Furthermore, unless otherwise required by context, singular terms shall include pluralities and plural terms shall include the singular.

Throughout the present specification, various aspects and components of the invention can be presented in a range format. The range format is included for convenience and should not be interpreted as an inflexible limitation on the scope of the invention. Accordingly, the description of a range should be considered to have specifically disclosed all the possible sub-ranges as well as individual numerical values within that range, unless specifically indicated. For example, description of a range such as from 1 to 5 should be considered to have specifically disclosed sub-ranges such as from 1 to 3, from 1 to 4, from 1 to 5, from 2 to 4, from 2 to 5, from 3 to 5 etc., as well as individual and partial (except where integers are required), numbers within the recited range, for example, 1, 2, 3, 4, 5, 5.5 and 6. This applies regardless of the breadth of the disclosed range. Where specific values are required, these will be indicated in the specification.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting essentially of" is intended to exclude elements which would materially affect the properties of the claimed composition, although may include elements that do not materially affect properties.

Herein the phrase "biointerfacial interaction" relates to interactions at the interface between a material surface and a biological environment in vitro or in vivo.

"Polymer", as used herein, includes homopolymers and copolymers. Examples of copolymers include, but are not limited to: alternating, statistical, block or gradient copolymers.

Macromonomers may also be utilised herein as a First or Second component. Herein a "macromonomer" is a polymer or oligomer the molecules of which may act as a First Component or Second Component, so that each individual polymer or oligomer molecule contributes only a "single" macromonomer monomer unit to a polymer coating.

Herein the term "inert environment" is a local environment for producing a crosslinked polymer coating, as defined herein, which is substantially depleted of atmospheric oxygen and water vapour. Examples of inert environments include reactions run under atmospheres of nitrogen or argon.

"Antimicrobial" as used herein, refers to molecules and/or compositions that kill (i.e., bactericidal), inhibit the growth of (i.e., bacteristatic), and/or prevent fouling by, microorganisms including bacteria, yeast, fungi, *mycoplasma*, viruses or virus infected cells, cancerous cells, and/or protozoa. In order to measure the level of antimicrobial inhibition, the surface coverage of *S. aureus* (SA38) on a sample disclosed herein can be compared to standard tissue culture polystyrene plates (TCPS), for example by comparing % of a sample polymer coated plate covered with the organism compared to TCPS. Other methods of measuring antimicrobial activity, known to those skilled in the art include: bacterial colonisation and biofilm formation assays, minimum inhibitory concentration assays to evaluate performance of antimicrobial compounds, drip-flow biofilm assays, disk diffusion assays, agar bacterial attachment assays, and other associated methods known to the skilled in the art.

Herein "Anti-fouling" or "non-fouling", refers to a composition that reduces or prevents the amount of adhesion of proteins, including blood proteins, plasma, cells, tissue and/or microbes to the substrate relative to the amount of adhesion to a reference coating or substrate such as tissue culture polystyrene (TCPS). Methods for measuring the "anti-fouling" characteristics of a material include: protein adsorption assays (e.g., enzyme-linked immunosorbent assays (ELISA), quartz crystal microbalance (QCM) based measurements, X-ray photoelectron spectroscopy (XPS) based analysis, the use of labelled proteins such as tritium labelled or lanthanide labelled proteins and the associated readout), mammalian cell attachment assays, bacterial colonisation and biofilm formation assays. In some cases a person skilled in the art can compare protein adsorption and/or cell attachment as a measure of anti-fouling and compare the levels to TCPS.

Herein "substantially non-cytotoxic", refers to a polymer coating that does not result in a substantial reduction or a change in the metabolism, proliferation, or viability of mammalian cells that contact the surface of the composition. Unless otherwise indicated, herein the cytotoxicity for the coatings was quantified using International Standard ISO10993-5/12.

"Immobilisation" or "immobilised", as used herein, refers to a material, such as a polymer coating as defined herein and/or a bioactive agent, which is covalently or non-covalently attached directly or indirectly to a substrate. Preferably the immobilisation of the material (for example the polymer coating) or bioactive agent is due to covalent bonding. For example, a polymer formed from a First Component, Second Component and at least one bioactive agent as defined herein may be immobilised on a substrate via the interaction of the First Component, Second Component and/or the at least one bioactive agent with functional groups present on at least one surface of the substrate. In an alternative example, a polymer formed from a First Component, Second Component and at least one bioactive agent as defined herein may be immobilised on a substrate via the interaction of photoreactive groups present on the First Component, the Second Component and/or the at least one bioactive agent with complementary groups present on at least one surface of the substrate. "Co-immobilisation" refers to immobilisation of two or more agents.

"Substrate", as used herein, refers to the material on which a polymer coating as defined herein is applied, or which is formed all or in part of a polymer coating, or on which the polymer coating (including one or more bioactive agents) is immobilised, such as via functional groups disposed on at least one surface of the substrate. Substrate also includes a primer layer of another polymer or coating which itself is then applied to another substrate. Preferably the substrate is a medical device.

"Coating", as used herein, refers to any temporary, semi-permanent or permanent layer, or layers, treating or covering a surface. The coating may be a chemical modification of the underlying substrate or may involve the addition of new materials to the surface of a substrate. It includes any increase in thickness to the substrate or change in surface chemical composition of the substrate. A polymer coating may be applied as a liquid and solidified into a solid coating.

Crosslinking

One potential advantage obtained from the crosslinking of the polymer coatings is the stability of the resulting coatings, for example crosslinking can reduce the solubility of the coating in comparison to similar compositions which are not crosslinked. In addition, the crosslinked nature of the polymer coatings may increase the chemical resistance of the composition. The application of a crosslinked polymer to a surface of an article, for example a medical device, may also yield a surface which has an increased heat tolerance, decreased permeability, better abrasion resistance and/or extend the life of the article.

Substrate

Herein the substrate could be an inert surface or it could comprise functional groups on at least one surface thereon, which can be used to anchor or immobilise a polymer coating. The functional groups can react to form covalent bonds between complimentary moieties on the First Component, the Second Component, or possibly one or more bioactive agents.

The polymer coating may be immobilised on a variety of different substrates. Examples of suitable substrate materials include, but are not limited to: metals, ceramics, glass, polymers (such as plastics), materials of biological origin, woven and non-woven fibres, inert materials such as silicon, and combinations thereof. In one embodiment the substrate is selected from the group consisting of: plastics, metals, ceramics, woven materials, silicon materials, and combinations thereof The coating may utilise premade polymers that are covalently attached to the surface and crosslinked. Multifunctional crosslinkers allow both attachment to the surface and crosslinking between the components of polymer, which can provide the low fouling properties.

Suitable metallic materials which may act as substrates include, but are not limited to: metals and alloys based on titanium, such as unalloyed titanium (ASTM F67) and titanium alloys, such as ASTM F1108, Ti-6A1-4V ELI (ASTM F136), Nitinol (ASTM F2063), nickel titanium alloys, and thermo-memory alloy materials; stainless steel (such as ASTM F138 and F139), tantalum (such as ASTM F560), palladium, zirconium, niobium, molybdenum, nickel-chrome, or certain cobalt alloys including Stellite, cobalt-chromium (such as Vitallium, ASTM F75 and Wrought cobalt-chromium (ASTM F90)), and cobalt-chromium-nickel alloys (such as ELGILOY® and PHYNOX®).

Suitable ceramics which may act as substrates include, but are not limited to: oxides, carbides, or nitrides of the transition elements such as titanium oxides, hafnium oxides, iridium oxides, chromium oxides, aluminium oxides, and zirconium oxides. Silicon based materials, such as silica, may also be used.

Suitable polymer substrates include, but are not limited to: polystyrene and substituted polystyrenes, polyalkylenes, such as polyethylene and polypropylene, poly(urethane)s, polyacrylates and polymethacrylates, polyacrylamides and polymethacrylamides, polyesters (for example DACRON®), polysiloxanes, poly-ethers, poly(orthoesters), poly(carbonates), poly(hydroxyalkanoate)s, polyfluorocarbons (for example polytetrafluoroethylene), polyether ether ketone (PEEK), parylene based polymers, dopamine based polymers, hydrogen cyanide derived polymers (aminomalononitrile), silicones, epoxy resins, polyalkenes, phenolic resins, aromatic polyamides, natural and synthetic elastomers, adhesives and sealants, polyolefins, polysulfones, polyacrylonitrile, biopolymers such as polysaccharides and natural latex copolymers thereof, and combinations thereof.

Substrates may be in the form of, or form part of: films, particles (for example: nanoparticles, microparticles, or millimetre diameter beads), fibres (such as: wound dressings, bandages, gauze, tape, pads, sponges, including woven and non-woven sponges and those designed specifically for dental or ophthalmic surgeries), surgical, medical or dental instruments, blood oxygenators, ventilators, pumps, drug delivery devices, tubing, wiring, electrodes, contraceptive devices, feminine hygiene products, endoscopes, grafts (including small diameter <6 mm), stents (including: coronary, ureteral, renal, biliary, colorectal, oesophageal, pulmonary, urethral, and vascular stents), stent grafts (including: abdominal, thoracic, and peripheral vascular stent grafts), pacemakers, implantable cardioverter-defibrillators, cardiac resynchronization therapy devices, cardiovascular device leads, ventricular assist devices and drivelines, heart valves, vena cava filters, endovascular coils, catheters (including: central venous, peripheral central, midline, peripheral, tunnelled, dialysis access, urinary, neurological, peritoneal, intra-aortic balloon pump, angioplasty balloon, diagnostic, interventional, or drug delivery catheters), catheter connectors and valves (including needleless connectors), intravenous delivery lines and manifolds, shunts, wound drains (internal or external including ventricular, ventriculoperitoneal, and lumboperitoneal), dialysis membranes, infusion ports, cochlear implants, endotracheal tubes, tracheostomy tubes, ventilator breathing tubes and circuits, guide wires, fluid collection bags, drug delivery bags and tubing, implantable sensors (e.g., intravascular, transdermal or intracranial sensors), ophthalmic devices including contact lenses, orthopaedic devices (including: hip implants, knee implants, shoulder implants, spinal implants (including: cervical plates systems, pedicle screw systems, interbody fusion devices, artificial disks, and other motion preservation devices), screws, plates, rivets, rods, intramedullary nails, bone cements, artificial tendons, and other prosthetics or fracture repair devices), dental implants, periodontal implants, maxillofacial implants, cosmetic implants, valves, appliances, scaffolding, suturing material, needles, hernia repair meshes, prosthetic neurological devices, tissue regeneration or cell culture devices, or other medical devices used within or in contact with a body or any portion of any of these items.

The polymer coatings can also be immobilised on to industrial or residential or other common substrates to prevent mildew, bacterial contamination, and in other applications where it is desirable to prevent fouling, such as: marine applications (ship hull coatings), fuel tanks, oil pipelines, industrial piping, pharmaceutical equipment, drug delivery devices such as inhalers, contact lenses, dental implants, coatings for in vivo sensors, textiles such as hospital drapes, gowns, or bedding, ventilation conduits, doorknobs, devices for separations, such as membranes for microbial suspension, biomolecule separation, protein fractionation, cell separation, waste water treatment, water purification, bioreactors, and food processing.

These polymer coatings can also be used to coat and thus treat surfaces of fibres, particulates and films for the applications of textiles, additives, electric/optical appliances, packaging materials and colorants/inks.

First Component

In one embodiment, the polymer coating described herein comprises at least one component defined herein as a "First Component".

In yet another embodiment the polymer coating comprises two or more components defined herein as a "First Component".

In one embodiment the First Component is a polymer, for example a macromonomer. In another embodiment the First Component is not a polymer.

The First Component may be a polymer which has been modified to include at least two alkenyl or epoxide groups, for example two or three alkenyl or epoxide groups. In one embodiment the First Component comprises at least two epoxide groups (for example at least two glycidyl groups). In another embodiment the First Component comprises at least two alkenyl groups.

The First Component may be a polymer, for example a macromonomer, (comprising at least two alkenyl or epoxide groups), the polymer being selected from, but not limited to: polyethylene glycols, polypropylene glycols, and poly(tetrahydrofurans), poly(dimethyl siloxanes), poly(vinyl alcohols), poly(acrylamides), poly(acrylates), poly(methacrylates), poly(methacrylamides), polypeptides, proteins, poly(vinyl pyrrolidone), polylactic acid, polyglycolic acid, poly(L-lactide), poly(D,L-lactide)polyglycolic acid [polyglycolide], poly(L-lactide-co-D,L-lactide), poly(L-lactide-co-glycolide), poly(D, L-lactide-2-co-glycolide), co-glycolide), poly(glycolide-co-trimethylene carbonate), poly(D,L-lactide-co-caprolactone), poly(glycolide-co-caprolactone), polyethylene glycol, polypropylene glycol, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly(phosphazene), poly(phosphate ester), poly(amino acid), maleic anhydride copolymers, polyiminocarbonates, poly[(97.5% dimethyl-trimethylene carbonate)-co-(2.5% trimethylene carbonate)], poly(orthoesters), polyalkylene oxides, dextran, hydroxypropylmethylcellulose, polysaccharides, and copolymers or mixtures thereof.

In a preferred embodiment the First Component may be a polyethylene glycol or a polyacrylamide. For example, a polyethylene glycol or a polyacrylamide comprising at least two epoxide groups or alkenyl groups.

In another preferred embodiment, the First Component may be a polymer comprising at least two epoxide groups (for example glycidyl groups) on terminal chain ends of the polymer, for example the polymer comprises two epoxide groups, wherein each epoxide group is located on a different terminal end group of the polymer. Alternatively, the First Component may be a polymer comprising at least two epoxide groups (for example glycidyl groups), wherein at least one of these epoxide groups is not located on a terminal chain end group.

The First Component may be a polymer comprising at least two alkenyl groups selected from an acrylate, acrylamide, allyl or vinyl group, wherein the at least two alkenyl groups are on terminal chain ends of the polymer. For example the polymer comprises two alkenyl groups, wherein each alkenyl group is located on a different terminal end group of the polymer. Alternatively, the First Component may be a polymer comprising at least two alkenyl groups, wherein at least one of these alkenyl groups is not located on a terminal chain end group.

Epoxide Groups

In one embodiment the First Component comprises multiple epoxide groups.

In one embodiment the First Component comprises at least two epoxide groups.

In another embodiment the First Component comprises two epoxide groups.

In another embodiment the First Component comprises three epoxide groups.

In yet another embodiment the First Component comprises more than three epoxide groups.

In yet another embodiment, the epoxide groups present on the First Component, for example on the terminal units of a polymer, are in the form of:

The First Component may be a non-polymer compound comprising two or three epoxide groups. For example, the First Component may be selected from, but not limited to: glycerol diglycidyl ether, neopentyl glycol diglycidyl ether-glycerol triglycerol ethertrimethylolpropane triglycidyl ether, trimethylolethane triglycidyl ether, trimethylolpropane triglycidyl ether, or mixtures thereof.

The First Component may be produced by converting hydroxy groups to glycidyl ether groups. For example, monohydric or polyhydric alcohols, such as dihydric alcohols, can be converted to the corresponding glycidyl ethers by a reaction with epichlorohydrin.

In another embodiment, compounds comprising more than two hydroxyl groups can be converted to the corresponding glycidyl ethers by reaction with epichlorohydrin.

In one embodiment the First Component is a polymer comprising two epoxide groups (for example glycidyl groups), wherein each epoxide group is at a different site along the polymer backbone.

In another embodiment the First Component is a polymer comprising two epoxide groups (for example glycidyl groups), wherein each epoxide group is on a chain end of the polymer. In yet another embodiment the epoxide groups are on different chain ends of the polymer.

The First Component may be a polymer selected from, for example: polyethylene glycols, polypropylene glycols, and poly(tetrahydrofurans), wherein corresponding glycidyl ethers can be obtained using epichlorohydrin, or other techniques known by a person skilled in the art.

In addition to homopolymers, it is possible to produce copolymers (for example block, gradient or statistical copolymers) comprising, for example, polyethylene glycol, polypropylene glycol and/or poly(tetrahydrofuran) monomers, wherein the copolymer comprises at least two epoxide groups.

Polyethylene glycol, polypropylene glycol and/or poly(tetrahydrofuran) homopolymers and/or copolymers comprising at least two epoxide groups may be utilised as a First Component for the polymer coatings, and may have molecular weights in a range of about 200 to about 50000 g mol$^{-1}$. For example, the polyethylene glycol, polypropylene glycol and/or poly(tetrahydrofuran) homopolymers and/or copolymers may have a molecular weight of: about 200, about 500, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, about 30000, about 31000, about 32000, about 33000, about 34000, about 35000, about 36000, about 37000, about 38000, about 39000, about 40000, about 41000, about 42000, about 43000, about 44000, about 45000, about 46000, about 47000, about 48000, about 49000, or about 50000 g mol$^{-1}$.

Polyethylene glycol (PEG) is a versatile material which has been utilised for many applications for the preparation of hydrogels for drug delivery and tissue engineering applications and for increasing circulation of bioactive molecules in vivo. All of these applications rely on the resistance of PEG towards non-specific protein adsorption and related biological responses such as immune responses.

In one embodiment the First Component is polyethylene glycol comprising two or three epoxide groups. For example, the First Component may be a polyethylene glycol comprising two epoxide groups.

Examples of useful polyepoxides which may be utilised as a First Component include, without limitation: epichlorohydrin resins and glycidol derivatives such as glycidyl esters, glycidyl ethers and N-glycidyl compounds. Non-limiting examples also include: polyglycidyl esters, diglycidyl butanediol ester, ethanediol diglycidyl ester, erythritol anhydride (EDE), butanediol diglycidyl ether (GAB), ethylene glycol diglycidyl ether, propylene glycol diglycidyl ether, glycerol-1,3-diglycidyl ether, polyethylene glycol diglycidyl ether, 1,6-hexanediol diglycidyl ether, propylene glycol diglycidyl ether, glycerol triglycidyl ether, diglycidyl, triglycidyl, and tetraglycidyl ethers and esters. Some specific examples of the foregoing include, without limitation: sorbitol polyglycidyl ether, polyglycerol polyglycidyl ether, pentaerythritol polyglycidyl ether, diglycerol polyglycidyl ether, triglycidyl tris (2-hydroxyethyl) isocyanurate, glycerol polyglycidyl ether, trimethylolpropane polyglycidyl ether, trimethylol propane triglycidyl ether, resorcinol diglycidyl ether, glycidyl ester ether of p-hydroxybenzoic acid, hydroquinone diglycidyl ether, neopentyl glycol diglycidyl ether, bisphenol A (PO)$_2$ diglycidyl ether, bisphenol S diglycidyl ether, hydrogenated bisphenol A diglycidyl ether, ethylene polyethylene glycol diglycidyl ether, propylene polypropylene glycol diglycidyl ether, polytetramethylene glycol diglycidyl ether, adipic acid diglycidyl ester, terephthalic acid diglycidyl ester, o-phthalic acid diglycidyl ester, higher dicarboxylic acid diglycidyl esters, and mixtures thereof.

Alkenyl Groups

In one embodiment the First Component comprises at least two alkenyl groups selected from: acrylate, acrylamide, allyl and vinyl groups, or a mixture thereof.

In another embodiment the First Component comprises at least two acrylate groups.

In another embodiment the First Component comprises at least two acrylamide groups.

In another embodiment the First Component comprises at least two allyl groups.

In another embodiment the First Component comprises at least two vinyl groups.

In one embodiment the First Component comprises a mixture of alkenyl groups, wherein each alkenyl group is selected from: acrylate, acrylamide, allyl and vinyl groups.

In another embodiment the First Component comprises multiple alkenyl groups selected from: acrylate, acrylamide, allyl and vinyl groups, or a mixture thereof.

In yet another embodiment the First Component comprises two alkenyl groups selected from: acrylate, acrylamide, allyl and vinyl groups, or a mixture thereof.

In another embodiment the First Component comprises three alkenyl groups selected from: acrylate, acrylamide, allyl and vinyl groups, or a mixture thereof.

In another embodiment the First Component comprises more than 3 alkenyl groups selected from: acrylate, acrylamide, allyl and vinyl groups, or a mixture thereof.

In one embodiment the First Component is a non-polymer compound comprising two or three alkenyl groups selected from: acrylate, acrylamide, allyl and vinyl groups, or a mixture thereof.

The First Component may be produced by converting functional groups present on compounds or polymers into appropriate alkenyl groups. For example hydroxyl or amine groups present on a compound or polymer can be treated with acryloyl chloride or acrylic anhydride.

In another embodiment, compounds comprising more than two hydroxyl groups can be can be treated with acryloyl chloride or acrylic anhydride. Examples of compounds comprising more than two hydroxyl groups include, but is not limited to: trimethylolethane, trimethylolpropane, glycerol, polyether triols, pentaerythritol, 1,2,5-pentanetriol, 1,2,6-hexanetriol, cyanuric acid, sorbitan, sugars such as sucrose, glucose, and mannose, and oligo and polysaccharides.

In one embodiment the First Component is a polymer comprising two alkenyl groups selected from: acrylate, acrylamide, allyl and vinyl groups, or a mixture thereof, wherein each alkenyl group is at a different site along the polymer backbone.

In another embodiment the First Component is a polymer comprising two alkenyl groups selected from: acrylate, acrylamide, allyl and vinyl groups, or a mixture thereof, wherein each alkenyl group is on a chain end of the polymer. In yet another embodiment the alkenyl groups are on different chain ends of the polymer.

The First Component may be produced by converting functional groups present on polymers into appropriate alkenyl groups. For example hydroxyl or amine groups present on a compound or polymer can be treated with acryloyl chloride or acrylic anhydride. Examples of polymers that can bet treat in this way may be selected from: polyethylene glycols, polypropylene glycols, and poly(tetrahydrofurans).

In addition to homopolymers, it is possible to produce copolymers (for example block, gradient or statistical copolymers) comprising, for example, polyethylene glycol, polypropylene glycol and/or poly(tetrahydrofuran) monomers, wherein the copolymer comprises at least two alkenyl groups.

Polyethylene glycol, polypropylene glycol and/or poly(tetrahydrofuran) homopolymers and/or copolymers comprising at least two alkenyl groups may be utilised as a First Component for the polymer coatings, and may have molecular weights in a range of about 200 to about 50000 g mol$^{-1}$. For example, the polyethylene glycol, polypropylene glycol and/or poly(tetrahydrofuran) homopolymers and/or copolymers may have a molecular weight of: about 200, about 500, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, about 30000, about 31000, about 32000, about 33000, about 34000, about 35000, about 36000, about 37000, about 38000, about 39000, about 40000, about 41000, about 42000, about 43000, about 44000, about 45000, about 46000, about 47000, about 48000, about 49000, or about 50000 g mol$^{-1}$.

Unreacted alkenyl and/or epoxide groups in the First Component may be utilised as conjugation points for compounds such as bioactive agents. For example, a free epoxide group can provide a conjugation point for an amine containing bioactive agent such as a peptide.

In one embodiment, the First Component comprises reactive groups (for example epoxide or alkenyl groups) that react with complimentary functional groups present on at least one surface of a substrate, to anchor a polymer coating to the substrate.

In another embodiment, the First Component comprises at least one group defined herein as a "bioactive agent". In this embodiment one or more bioactive agents are covalently bound to the First Component and may have been introduced during the formation of the First Component (for example the bioactive agent may be introduced as a monomer during a polymerisation reaction to produce a First Component), or after the formation of the First Component (for example, in a post-polymerisation modification).

Second Component

In one embodiment the polymer coating defined herein comprises at least one component defined herein as a "Second Component".

In yet another embodiment the polymer coating comprises two components defined herein as a "Second Component".

A suitable Second Component may be a straight-chain or branched, linear or cyclic, aliphatic or aromatic hydrocarbon which possess at least one amine group, for example 1, 2 or 3 amine groups. The amine groups may be primary amines or secondary amines. The Second Component may be a non-polymer compound, for example a non-polymer compound selected from, but not limited to: 1,2-diaminoethane, 1,2-diaminopropane, 1,3-diaminopropane, 1,3-diamino-2-propanol, 3,3'-diamino-N-methyldipropylamine, 1,4-diaminobutane, 1,3-diaminobutane, 1,2-diaminobutane, 1,5-diaminopentane, 1,4-diaminopentane, 1,3-diaminopentane, 1,2-diaminopentane, 1,5-diamino-2-methylpentane, 1,6-diaminohexane, 1,5-diaminohexane, 1,4-diaminohexane, 1,3-diaminohexane, 1,2-diaminohexane 1,12-dodecanediamine, 1,11-diamino-3,6,9-trioxaundecane, diethylenetriamine, isophoronediamine, or mixtures thereof.

The Second Component may be a polymer. For example the Second Component may be a polymer comprising 1, 2 or 3 primary or secondary amines groups. Alternatively, the Second Component may be a polymer selected from, but not limited to: polyacrylamide, polyallylamine, polyethyleneimine, polylysine, proteins, chitosan, or a mixture thereof.

In one embodiment, the Second Component is polyacrylamide.

The Second Component may be a polymer which inherently comprises at least one two or three amine groups, or can be modified to include at least one, two or three amine groups. The polymer may be selected, but not limited to, the group consisting of: polyethylene glycols, polypropylene glycols, poly(dimethyl siloxanes), poly(vinyl alcohols), poly(acrylamides), poly(acrylates), poly(methacrylates), poly(methacrylamides), polypeptides, proteins, poly(vinyl pyrrolidone), poly(tetrahydrofurans), polylactic acid, polyglycolic acid, poly(L-lactide), poly(D,L-lactide) polyglycolic acid[polyglycolide], poly(L-lactide-co-D,L-lactide), poly(L-lactide-co-glycolide), poly(D, L-lactide-2-co-glycolide), co-glycolide), poly(glycolide-co-trimethylene carbonate), poly(D,L-lactide-co-caprolactone), poly(glycolide-co-caprolactone), polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, zwitterionic polymers, and copolymers or mixtures thereof.

Furthermore, the Second Component may be a polymer which has been modified to include at least one amine group, for example two or three amine groups. The modified polymer may be selected from, but not limited to: polyvinyl alcohol, dextrans, polylactic acid, polyglycolic acid, poly(L-lactide), poly(D,L-lactide)polyglycolic acid[polyglycolide], poly(L-lactide-co-D,L-lactide), poly(L-lactide-co-glycolide), poly(D, L-lactide-2-co-glycolide), co-glycolide), poly(glycolide-co-trimethylene carbonate), poly(D,L-lactide-co-caprolactone), poly(glycolide-co-caprolactone), polyethylene glycol, polypropylene glycol, polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly(phosphazene), poly(phosphate ester), poly(amino acid), maleic anhydride copolymers, polyiminocarbonates, poly[(97.5% dimethyl-trimethylene carbonate)-co-(2.5% trimethylene carbonate)], poly(orthoesters), polyalkylene oxides, dextran, hydroxypropylmethylcellulose, polysaccharides, zwitterionic polymers, and copolymers or mixtures thereof. Trimethylolpropane tris[poly(propylene glycol), amine terminated] ether is an example of a polymer comprising 3 amino groups which could be used as a Second Component.

In one embodiment, the Second Component is a polyethylene glycol or polypropylene glycol homopolymer or copolymer, which comprises at least one amine group, for example 1, 2 or 3 amine groups. The polyethylene glycols or polypropylene glycols may have a molecular weight in a range of about 200 to about 50000 g mol$^{-1}$, for example: about 200, about 500, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000, about 20000, about 21000, about 22000, about 23000, about 24000, about 25000, about 26000, about 27000, about 28000, about 29000, about 30000, about 31000, about 32000, about 33000, about 34000, about 35000, about 36000, about 37000, about 38000, about 39000, about 40000, about 41000, about 42000, about 43000, about 44000, about 45000, about 46000, about 47000, about 48000, about 49000, or about 50000 g mol$^{-1}$.

The Second Component may be a homopolymer or copolymer which is formed from amine containing monomers. Examples of amine containing monomers include, but are not limited to: acrylamide, methacrylamide, N-methylacrylamide, N,N-dimethylacrylamide, N-tert-butylmethacrylamide, N-isopropylacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, 2-hydroxylpropyl methacrylamide, 2-hydroxylpropyl acrylamide, zwitterionic acrylamide, and mixtures thereof.

Alternatively, homopolymers or copolymers can be synthesised and undergo post-synthesis modification to introduce one or more amine groups, onto the polymer backbone or on one or more terminal groups at the end(s) of a polymer or copolymer chain. These polymers may be initially formed by any technique known in the art, including, but not limited to: free radical polymerisation, ionic polymerisation, ring opening metathesis polymerisation (ROMP), atom transfer radical polymerisation (ATRP), catalytic chain transfer polymerisation (CCTP) nitroxide mediated polymerisation (NMP), or reversible addition fragmentation chain transfer (RAFT) polymerisation. These techniques can be utilised to polymerise monomers including, but not limited to: maleic anhydride, N-alkylmaleimide, N-arylmaleimide, dialkyl fumarate, cyclopolymerisable monomers, acrylate and methacrylate esters, acrylic and methacrylic acid, styrene, acrylamides, methacrylamides, methacrylonitrile, and mixtures thereof.

The Second Component may be a polymer synthesised via the RAFT process. The use of the RAFT technique for synthesising polymers from a vast array of monomers is known (G. Moad et al., "*Living Radical Polymerization by the RAFT Process*", *Australian Journal of Chemistry*, 58(6) 379-410, 2005). The RAFT process can be applied to any monomers or monomer combinations which are susceptible to free-radical polymerisation. Such monomers include, but are not limited to: maleic anhydride, N-alkylmaleimide, N-arylmaleimide, dialkyl fumarate, cyclopolymerisable monomers, acrylate and methacrylate esters, acrylic and methacrylic acid, styrene, acrylamides, methacrylamides, methacrylonitrile, and mixtures thereof. Examples of amine containing monomers which can be polymerised via the RAFT process include, but are not limited to: acrylamide, methacrylamide, N-methylacrylamide, N,N-dimethylacrylamide, N-tert-butylmethacrylamide, N-isopropylacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, 2-hydroxylpropyl methacrylamide, 2-hydroxylpropyl acrylamide, zwitterionic acrylamide, and mixtures thereof.

In one embodiment the Second Component is a homo- or co-polymer of: 2-hydroxylpropyl acrylamide, acrylamide, 2-hydroxyl propyl methacrylamide, polyethylene glycol methacrylate, polyethylene glycol acrylate, polyethylene glycol acrylamide, polyethylene glycol methacrylamide, monomers carrying zwitterionic groups such as carboxy betaine methacrylate, monomers carrying carbohydrate moieties, such as methacryloxy ethyl glucoside, vinyl alcohol, N-vinyl pyrrolidone, or a mixture thereof.

End-group modification of polymers is known in the art, this includes the post-synthesis modification of polymers produced via the RAFT technique (H. Willock, et al., "End Group Removal and Modification of RAFT Polymers", *Polym. Chem.*, 1, 149-157, 2010). The dithioester end group on a polymer produced via the RAFT process, can, for example be removed via aminolysis to yield a free thiol which can then possibly undergo a further conjugation reaction, for example by reacting the thiol with an alkene via a "thiol-ene" reaction (A. B. Lowe, "Thiol-Ene "Click" Reactions and Recent Applications in Polymer and Materials Synthesis", *Polym. Chem.*, 1, 17-36, 2010).

In one embodiment, the Second Component is a polymer produced via the RAFT technique. In a further embodiment the chain ends of a polymer produced via the RAFT technique are modified after the synthesis of the polymer, for example, at least one chain end is modified to incorporate a free amine, such as a primary amine.

In one embodiment, the Second Component comprises reactive groups (for example amine groups) that react with complimentary functional groups on a substrate, to anchor a polymer coating to the substrate.

The First Component or the Second Component or both Components may further comprise photoreactive groups (for example at least one, two or three photoreactive groups). The photoreactive groups may be benzophenone derivates and phenylazide derivates. These additional groups can provide a mechanism for crosslinking of polymer coatings as well as covalent attachment of these coatings on a substrate material that are lacking functional groups. Such photoreactive groups can be incorporated into the coating formulations described by the present invention by simply adding photoreactive molecules that contain suitable functional groups for covalent incorporation in the final coating, such as an amine or epoxy group, or by using the First Component of the present invention comprising at least two epoxide groups, or at least two alkenyl groups, and further comprising at least one photoreactive group, or by using a modified Second Component of the present invention comprising at least one amine group that also contains at least one photoreactive group. By using these photoreactive groups, the need for functional groups on the substrate material is eliminated while covalent attachment of the coating described in the present invention can be achieved.

Examples of photoreactive groups which may be present on the First Component, Second Component or on an additional compound added to a coating mixture include, but are not limited to: benzophenone groups, benzophenone derivates, phenyl azide, ortho-hydroxphenyl azide, meta-hydroxphenyl azide, tetraflurorophenyl azide, ortho-nitrophenyl azide, meta-nitrophenyl azide, diazirine, azido-methylcoumarin, or mixture thereof.

The molar ratio of the First Component and the Second Component may be in a range of about 4:1 to about 1:4. For example the molar ratio between the First Component and the Second Component may be about 4:1; about 3:1; about 2:1; about 1:1; about 1:2; about 1:3, or about 1:4.

In another embodiment, the Second Component comprises at least one group defined herein as a "bioactive agent". In this embodiment at least one bioactive agent is covalently bound to the Second Component and may have been introduced during the formation of the Second Component (for example the bioactive agent may be introduced as a monomer during a polymerisation reaction to produce a Second Component), or after the formation of the Second Component (for example, in a post-polymerisation modification).

Bioactive Agent

The crosslinked polymer coatings defined herein comprise at least one bioactive agent. At least one bioactive agent may be incorporated in conjunction with the formation of the crosslinked polymer coating in a one-step, i.e., "one pot", procedure. Alternatively at least one bioactive agent may be incorporated into the crosslinked polymer coating after the coating has been formed via a two-step process.

Said one-pot-reaction is preferred as it may be more cost-, time- and/or volume-efficient than a corresponding two-step process.

Alternatively, the at least one bioactive agent may be covalently bound to the First or Second Component before forming the crosslinked polymer coating. This may be achieved for example, by co-polymerisation via RAFT polymerisation or via a post-polymerisation modification.

The number of bioactive agents incorporated into a polymer coating as defined herein will depend on a number of factors, for example the number and type of different bioactive agents may be dictated by the final application for the substrate being coated. For example a polymer coating as defined herein may require the presence of 1, 2, 3, or more different bioactive agents. In one embodiment at least one bioactive agent is incorporated into a polymer coating as defined herein. In another embodiment, at least two different bioactive agents are incorporated into a polymer coating as defined herein. In yet another embodiment more than two different types of bioactive agent are incorporated in a polymer coating as defined herein.

Herein, the terms "bioactive agent", "bioactive molecule" or "biomolecule", refer to any organic or inorganic molecule that may be therapeutic, prophylactic or diagnostic that actively or passively influences a biological system. Bioactive agents which can be incorporated in the polymer coating described herein, include, but is not limited to: pharmaceutical drugs, compounds which act as quorum sensing inhibitors (such as fimbrolides), metal complexing compounds (such as those carrying silver or bismuth), antimicrobial compounds, amino acids, peptides (such as peptides comprising free amino groups or antimicrobial peptides), peptidomimetics, synthetic analogues of natural bioactive molecules, synthetic peptide mimetics, proteins (such as antibodies, activating, signalling or signal amplifying biomolecules, including, but not limited to: a protein kinase, cell adhesion mediators, a cytokine, a chemokine, an interferon, tumour necrosis factor, growth factor, growth factor inhibitor, hormone, cohesin, laminin, fibronectin, fibrinogen, osteocalcin, osteopontin, osteoprotegerin, enzymes), receptor-targeting ligands, gene silencing agents, ambisenses, antisenses, an RNA, a living cell, antibiotics, or a mixture thereof.

Suitable bioactive agents may be enzymes, glycoproteins, peptides, oligopeptides, polypeptides, inorganic compounds, organometallic compounds, or organic compounds. The bioactive agent may be naturally occurring or a synthetically derived compound.

The terms "polypeptide", "peptide", and "oligopeptide" encompass organic compounds composed of amino acids, whether natural, synthetic or mixtures thereof, that are linked together chemically by peptide bonds. The polypeptides can be "exogenous," or "heterologous," i.e., production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

The bioactive agent can be incorporated into the polymer coating utilising, for example, amino, epoxy, acrylate or acrylamide reactive groups present in the bioactive agent. Alternatively, the bioactive agent may be modified prior to incorporation into a polymer coating described herein. For example, reactive groups such as: amino groups, epoxide groups, acrylate groups, vinyl groups or allyl groups may be introduced into the bioactive agent. Reactive groups present on the bioactive agent can react with complimentary groups on: the First Component, Second Component, and/or functional groups present on the substrate.

Preferred bioactive agents include peptides, metal complexing compounds, enzymes and small organic molecules.

In one embodiment the bioactive agent is a peptide.

Examples of specific bioactive agents include, but are not limited to: RGD and RAD cyclic peptides, melimine antimicrobial peptide, 5-methylene-1-(prop-2-enoyl)-4-(2-fluorophenyl)-dihydropyrrol-2-one (DHP), or a mixture thereof. Melimine is a custom synthesised antimicrobial peptide derived from portions of melittin and protamine and has the following amino acid sequence:

TLISWIKNKRKQRPRVSRRRRRRGGRRRR.

Figure 11:
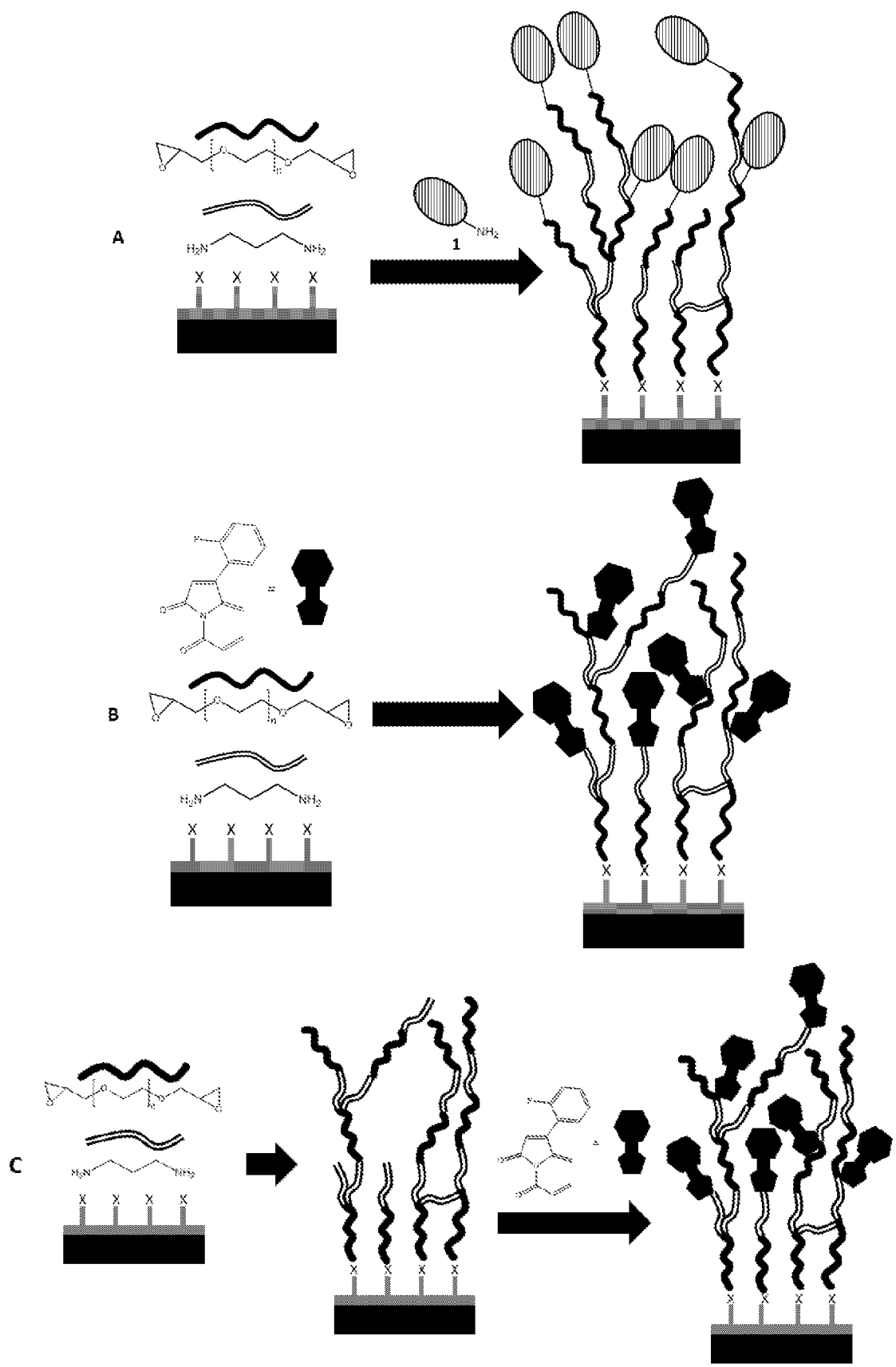
FIG. 11—Image A shows the preparation of a PEGDGE and DAP coating, and the incorporation of an amine containing bioactive agent (Component 1). Images B and C show the preparation of a PEGDGE and DAP coating, and the incorporation of 5-methylene-1-(prop-2-enoyl)-4-(2-fluorophenyl)-dihydropyrrol-2-one (DHP) using either a one-step method (image B) or a two-step method (image C).

When forming a polymer coating as disclosed herein, one or more bioactive agents can be incorporated in the initial formation of the polymer coating, or in a post modification or reaction step following the formation of the polymer coating (i.e., at least one bioactive agent can be incorporated into a polymer coating in a one or two step process). An example of this is shown in FIG. 11. In image A of FIG. 11, a one-step procedure is used to form the polymer coating with poly(ethylene glycol) diglycidyl ether (PEGDGE) and 1,3-diaminopropane (DAP), with an exemplary bioactive, such as a peptide (shown as component 1), being incorporated in situ during the formation of the polymer coating. In image B of FIG. 11, a one-step procedure is used to form the polymer coating with PEGDGE with 5-methylene-1-(prop-2-enoyl)-4-(2-fluorophenyl)-dihydropyrrol-2-one (DHP) incorporated in situ during the formation of the polymer coating. In image C of FIG. 11 a two-step procedure is used to form the polymer coating with PEGDGE and DAP. In this scenario the DHP is incorporated in a second step following the formation of the polymer coating.

One or more bioactive agents may be incorporated into the polymer coating due to reactive groups on the one or more bioactive agents reacting with complimentary groups present on at least one of a First Component, Second Component or a substrate.

In one embodiment the formation of the polymer coating and the incorporation of at least one bioactive agent into the polymer coating is performed in a one-step procedure In another embodiment the formation of the polymer coating and the incorporation of at least one bioactive agent into the polymer coating, is performed in a two-step procedure, wherein the polymer coating is initially formed and the at least one bioactive agent is introduced into the polymer coating in a second step. In a two-step process, the bioactive agent may be introduced during the formation of the polymer coating, or after the formation of the polymer coating during a post-modification procedure.

Polymer Coatings and Methods for Producing Polymer Coatings

Disclosed herein are polymer coatings derived from a First Component, Second Component and at least one bioactive agent as defined herein. In one preferred embodiment the polymer coating as defined herein are crosslinked.

Disclosed herein is a method for coating a substrate on at least one surface of the substrate, the method comprising:
a) providing:
 a First Component comprising at least two epoxide groups or at least two alkenyl groups; and
 a Second Component comprising at least one amine group; and
b) forming a covalently crosslinked polymer coating with the First Component and the Second Component, the polymer coating being immobilised on the substrate,
wherein at least one bioactive agent comprising at least one suitable reactive group for incorporation (such as covalent incorporation), into the covalently crosslinked polymer coating is introduced prior to, during or after the formation of the covalently crosslinked polymer.

In one embodiment at least one bioactive agent is introduced in step a), for example together with the First Component and the Second Component, to provide a crosslinked polymer coating comprising one or more bioactive agents in a one-step process.

In another embodiment the at least bioactive agent may be introduced during the formation of the crosslinked polymer coating in step b).

In another embodiment the at least bioactive agent may be introduced after the crosslinked polymer coating has been formed in step b), to provide a crosslinked polymer coating comprising one or more bioactive agents in a two-step process.

Also disclosed herein is a method for coating a substrate that comprises functional groups on at least one surface of the substrate, the method comprising:
a) providing:
 a First Component comprising at least two epoxide groups or at least two alkenyl groups; and
 a Second Component comprising at least one amine group; and
b) forming a covalently crosslinked polymer coating with the First Component and the Second Component, the polymer coating being immobilised (such as covalently immobilised) on the substrate via the functional groups,
wherein at least one bioactive agent comprising at least one suitable reactive group for incorporation into the covalently crosslinked polymer coating is introduced prior to, during or after the formation of the covalently crosslinked polymer.

Also disclosed herein is a method for coating a substrate on at least one surface of the substrate, the method comprising:
a) providing:
 a First Component comprising at least two epoxide groups or at least two alkenyl groups; and
 a Second Component comprising at least one amine group, with the proviso that at least one of the First Component and the Second component further comprises at least one photoreactive group; and
b) forming a covalently crosslinked polymer coating with the First Component and the Second Component, the polymer coating being immobilised on the substrate,
wherein at least one bioactive agent comprising at least one suitable reactive group for incorporation into the covalently crosslinked polymer coating is introduced prior to, during or after the formation of the covalently crosslinked polymer.

In another embodiment the substrate contains functional groups and the polymer coating is covalently immobilised on the substrate via the functional groups.

Also disclosed herein is composition produced by a method as defined herein.

Also disclosed herein is a polymer coating, which is preferably crosslinked, the polymer coating being formed from:
a First Component comprising at least two epoxide groups or at least two alkenyl groups;
a Second Component comprising at least one amine group; and
at least one bioactive agent.

In one embodiment, at least one of the First Component, Second Component or bioactive agent further comprises at least one photoreactive group.

Also disclosed herein is a composition comprising:
a substrate;
a crosslinked polymer coating which is immobilised on the substrate, wherein the crosslinked polymer coating is formed from:
 a First Component comprising at least two epoxide groups or at least two alkenyl groups;
 a Second Component comprising at least one amine group; and
 at least one bioactive agent.

In one embodiment, the substrate comprises functional groups. In another embodiment the crosslinked polymer coating is immobilised on the substrate via these functional groups.

In yet another embodiment, at least one of the First Component and/or the Second Component further comprise at least one photoreactive group. The photoreactive group may immobilise the crosslinked polymer coating in cases where the substrate comprises no appropriate inherent functional groups, or no functional groups have been introduced via synthetic processes known in the art.

Also disclosed herein is a composition comprising:
a substrate;
a crosslinked polymer coating which is immobilised (for example covalently bound) on the substrate via functional groups present on a surface of the substrate,
wherein the crosslinked polymer coating is formed from:
 a First Component comprising at least two epoxide groups or at least two alkenyl groups;
 a Second Component comprising at least one amine group; and
 at least one bioactive agent.

Also disclosed herein is a composition comprising:
a substrate;
a crosslinked polymer coating which is immobilised on the substrate,
wherein the crosslinked polymer coating is formed from:
 a First Component comprising at least two epoxide groups or at least two alkenyl groups;
 a Second Component comprising at least one amine group; and
 at least one bioactive agent,
with the proviso that at least one of the First Component and the Second component further comprises at least one photoreactive group.

Disclosed herein is a composition consisting essentially of:
a substrate;
a crosslinked polymer coating which is immobilised (for example covalently bound) on the substrate optionally via functional groups which may be present on a surface of the substrate,
wherein the crosslinked polymer coating is formed from:
a First Component comprising at least two epoxide groups or at least two alkenyl groups;
a Second Component comprising at least one amine group; and
at least one bioactive agent.

Disclosed herein is the use of a polymer coating or crosslinked polymer coating as described herein, as an antifouling coating.

Disclosed herein is the use of a polymer coating or crosslinked polymer coating as described herein, as an antimicrobial coating.

The polymer coating may be produced in the absence of a vacuum. Alternatively the polymer coating may be produced in an environment which is not an inert environment.

In one embodiment the polymer coating is produced in the absence of a catalyst.

Also disclosed herein is the use of a polymer coating as described herein for coating a substrate wherein the substrate is in the form of a medical device to which the polymer coating is applied as a coating.

Figure 2:
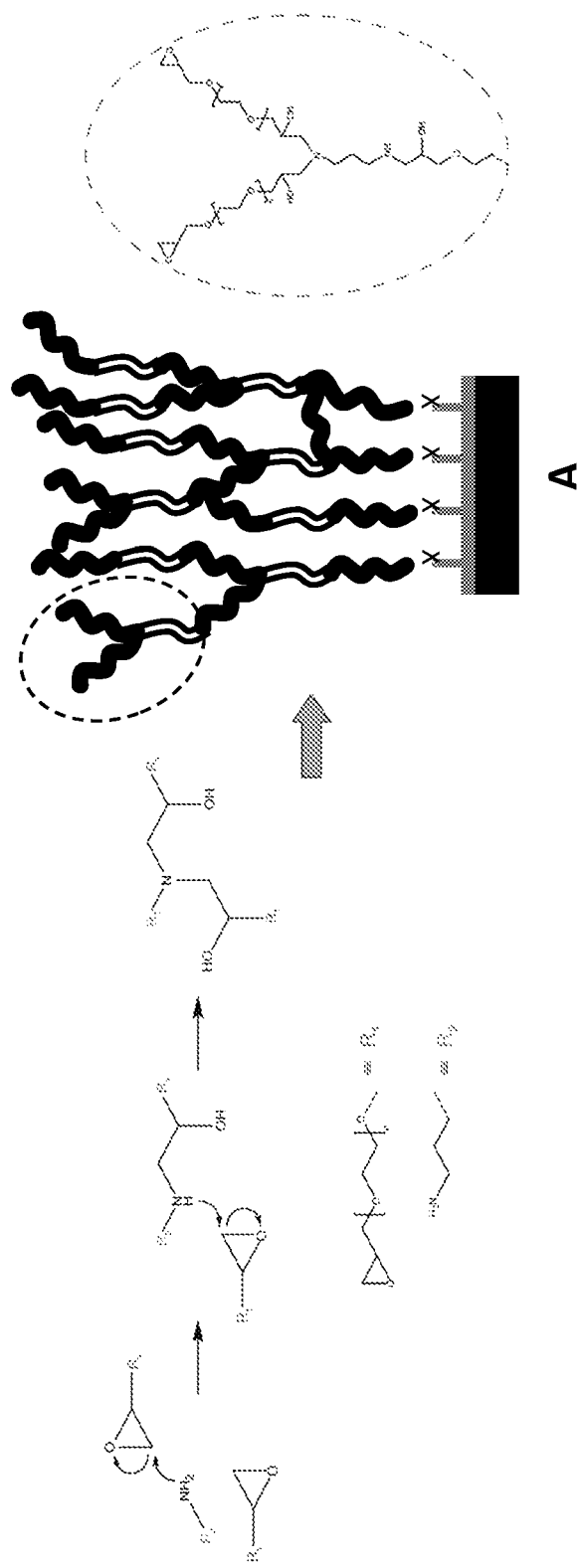
FIG. 2—A schematic showing the reaction scheme and crosslinking of poly(ethylene glycol) diglycidyl ether and diaminopropane on a functionalised surface of a substrate. Image A shows a crosslinked coating on the surface. Substituent "X" is a functional group, for example $NH_2$, OH or COOH.

FIG. 1 shows the crosslinking of poly(ethylene glycol) diglycidyl ether and diaminopropane to form the crosslinked coating. Substituent X in FIG. 1 may be a functional group such as $NH_2$, OH or COOH. Each amino group is able to react with up to two epoxide functionalities, allowing crosslinking to take place (FIG. 2). The epoxide groups are also able to react with amino groups present on the surface of a substrate, forming covalent bonds between a growing polymer coating and concurrently immobilizing the growing polymer coating on the substrate.

FIG. 1 and FIG. 11 show methods of producing polymer coatings and, in the case of FIG. 11, the incorporation of a bioactive agent in either a one-step (images A and B) or two-step process (image C). In these examples a surface of the substrate can comprise free amino groups which can be incorporated into a growing polymer coating, allowing the coating to be immobilised on the substrate.

The polymer coatings described herein may be generally prepared using grafting to methods. The polymer material can be grafted directly to the substrate surface by covalently attaching the polymer to the substrate from reactive functional groups present on a surface of the substrate.

Herein the substrate can comprise functional groups on at least one surface thereon, which can react with complimentary groups on the First Component and/or Second Component, or even the at least one bioactive agent, in order to immobilise a polymer coating onto the substrate.

The substrate can comprise functional groups on at least one surface thereon, which can be used to anchor or immobilise a polymer coating. The functional groups can react to form covalent bonds between complimentary moieties on the First Component and/or the Second Component. These functional groups may also be used as anchoring points from which to attach therapeutic, diagnostic, prophylactic agents, or any other bioactive agent as defined herein.

More than one surface on a substrate may comprise functional groups which can react with complimentary groups on the First Component, Second Component and/or at least one bioactive agent, in order to immobilise a polymer coating onto the substrate. The substrate may be manufactured so that functional groups are disposed on specific sections of the substrate in order to localise the attachment of a polymer coating as defined herein. Alternatively entire surfaces, for example as the entire external surface of a substrate such as a medical device, may be treated to incorporate appropriate functional groups which can be used as anchor points to immobilise the polymer coating to the substrate.

Covalent attachment of these coatings on a substrate material that are lacking functional groups can be with the use of photoreactive groups. These groups can be incorporated into the coating formulations described by the present invention by adding photoreactive molecules that contain suitable functional groups for covalent incorporation in the final coating, such as an amine or epoxy group, or by using the First Component of the present invention comprising at least two epoxide groups that contains at least one photoreactive group, or by using a modified Second Component of the present invention comprising at least one amine group that also contains at least one photoreactive group. By using these photoreactive groups, the need for functional groups on the substrate material is eliminated while covalent attachment of the coating described in the present invention can be achieved.

The substrate may comprise at least one surface comprising functional groups selected from, but not limited to: hydroxyl groups, amino groups, carboxylic groups, epoxide groups, vinyl groups, allyl groups, acrylate groups, acrylamide groups, siloxane groups, aldehyde groups, azide groups, alkyne groups, thiol groups, isocyanate groups, N-hydroxysuccinimide groups, maleimido groups, or mixtures thereof. The functional groups may be inherently present in or on the substrate, or be introduced via synthetic means, such as chemical modification.

The substrate may comprise small molecules or polymers with functional groups selected from, but not limited to: hydroxyl groups, amino groups, carboxylic groups, epoxide groups, vinyl groups, allyl groups, acrylate groups, acrylamide groups, siloxane groups, aldehyde groups, azide groups, alkyne groups, thiol groups, isocyanate groups, N-hydroxysuccinimide groups, maleimido groups, or mixtures thereof.

The use of functional groups on a surface of the substrate is beneficial as it allows for a uniform distribution of functional groups to be present which can advantageously lead to much higher coating densities in comparison to methods utilising graft to methods. This is because the functional groups can be packed closer together on and/or in the substrate, than larger polymer molecules synthesised in solution.

In order to form the polymer coating, at least one compound designated herein as a "First Component" and at least one compound defined herein as a "Second Component" are utilised.

The First Component may comprise at least two epoxy groups, or at least two alkenyl groups. The Second Component may comprise at least one amine group, or at least two amine groups.

Amine groups on the Second Component can react with epoxy groups in a ring opening reaction as shown in FIG. 2. Alternatively, alkenyl groups, such as acrylate or acrylamide groups, present on a First Component can undergo reactions such as a Michael Addition polymerisation reaction with amine groups present on the Second Component.

Functional groups on the substrate can react with complimentary components on the first and Second Component. For example hydroxyl or amino functional groups can react with epoxide groups on the First Component, or carboxylic functional groups can react with amine groups on the Second Component to produce an amide linkage.

The general procedure described herein can be modified as necessary to accommodate different substrate materials, functional group systems, and/or monomer compositions.

For a new coating method to be translated into commercial products, it is preferable that the precursors are cost effective, easily procurable and that the coating manufacture is facile and amenable for scale-up. In the present disclosure, commercially available precursors can be utilised which allow the preparation of effective low fouling coatings using the presently described technique. Moreover, coatings prepared by the presently disclosed method allows, inter alia, direct coupling of amine containing bioactive molecules.

High density surface grafting of polymers is a versatile technique for the preparation of low-fouling and/or highly functional coatings with a large range of polymers. However, often catalysts and/or an inert atmosphere (i.e., nitrogen) are required for the preparation of such surfaces. These required conditions often can be an obstacle in the scale-up and wide application of such coatings. In the present disclosure, utilising reactions such as epoxy-amine chemistry can be performed without the need for initiators, catalysts or an inert atmosphere.

In one embodiment the polymer coating is antimicrobial.

In one embodiment the extent to which a coating is described as being antimicrobial is its relative ability to exclude coverage of a microbial species compared to the standard tissue culture polystyrene plate (TCPS). That is, an antimicrobial coating of the present invention presents a surface that contains less than 5% of coverage of S. aureus compared to standard tissue culture polystyrene plate.

In yet another embodiment, protein adsorption and/or cell attachment can be measured and compared to TCPS.

In another embodiment the polymer coating is anti-fouling.

In one embodiment the extent to which a coating is described as being anti-fouling is its relative ability to exclude attachment of cells or proteins compared to the standard tissue culture polystyrene plate. In another embodiment, an antifouling coating of the present invention presents a surface that allows no more than 0.05% of protein adsorption compared to standard tissue culture polystyrene plate and/or no more than 30% of cell attachment.

Methods of Use

The materials described herein as a "substrate", may be in the form of a medical device to which the polymer coating is applied as a coating. Suitable devices include, but are not limited to: surgical, medical or dental instruments, ophthalmic devices, wound treatments (including: bandages, sutures, cell scaffolds, bone cements, particles), appliances, implants, scaffolding, suturing material, valves, pacemaker, stents, catheters, rods, implants, fracture fixation devices, pumps, tubing, wiring, electrodes, contraceptive devices, feminine hygiene products, endoscopes, wound dressings and other devices, which come into contact with tissue, including human tissue.

In one embodiment, the polymer coatings are coated directly on a fibrous material, incorporated into a fibrous material or coated indirectly on a fibrous material (e.g., coated on a different surface coating). These include wound dressings, bandages, gauze, tape; pads, sponges, including woven and non-woven sponges and those designed specifically for dental or ophthalmic surgeries, paper or polymer materials used as surgical drapes, disposable diapers, tapes, bandages, feminine products, sutures, and other fibrous materials.

Fibrous materials are also useful in cell culture and tissue engineering devices. Bacterial and fungal contamination is a major problem in eukaryotic cell culture and this provides a safe and effective way to minimise or eliminate contamination of the cultures, while allowing selective attachment of the desired cells through the incorporation of directed adhesion proteins into the material.

The polymer coatings may be readily bound to particles, including nanoparticles, microparticles, millimetre beads, or formed into micelles, that have uses in a variety of applications including cell culture, as mentioned above, and drug delivery. Non-fouling, biocompatible, polymer micelles would prevent protein denaturation preventing activation of the immune response allowing for a more stealthy delivery of the desired therapeutic.

Also disclosed herein is the use of a polymer coating as defined herein in the form of a composition for coating a substrate, wherein the substrate is in the form of a medical device to which the composition is applied as a coating.

The polymer coatings may be applied directly to, or incorporated in, a substrate, for example a substrate composed of polymer, metallic, or ceramic elements. The polymer coatings may be applied directly to, or incorporated in a substrate such as a device, for example a medical device. Suitable devices include, but are not limited to: surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronization therapy devices, ventricular assist devices, heart valves, catheters (including vascular, urinary, neurological, peritoneal or interventional catheters), shunts, wound drains, dialysis membranes, infusion ports, cochlear implants, endotracheal tubes, guide wires, fluid collection bags, sensors, wound treatments (for example dressings, bandages, sutures, cell scaffolds, bone cements or particles), ophthalmic devices, orthopaedic devices (for example: hip implants, knee implants, spinal implants, screws, plates, rivets, rods, intramedullary nails, bone cements, artificial tendons, and other prosthetics or fracture repair devices), dental implants, breast implants, penile implants, maxillofacial implants, cosmetic implants, valves, appliances, scaffolding, suturing material, needles, hernia repair meshes, tension-free vaginal tape and vaginal slings, tissue regeneration or cell culture devices, or other medical devices used within or in contact with the body or any portion of any of these.

Preferably, the polymer coating described herein does not significantly adversely affect the desired physical properties of the substrate, for example a device. These physical properties may include, but is not limited to: flexibility, durability, kink resistance, abrasion resistance, thermal and electrical conductivity, tensile strength, hardness and/or burst pressure.

The polymer coatings can also be added to painted surfaces and other coatings and filters to prevent mildew, bacterial contamination, and in other applications where it is desirable to prevent fouling, such as: marine applications (ship hull coatings), contact lenses, dental implants, coatings for in vivo sensors, devices for separations, such as membranes for microbial suspension, biomolecule separation, protein fractionation, cell separation, waste water treatment, bioreactors, and/or food processing.

Other possible applications may include the treatment of fibres, particulates and films for applications in textiles, additives, electric/optical appliances, packaging materials and colorants/inks.

EXAMPLES

Materials and Methods

XPS Analysis

X-ray photoelectron spectroscopy (XPS) analysis was performed using an AXIS Ultra DLD spectrometer (Kratos Analytical Inc., Manchester, UK) with a monochromated Al Kα source at a power of 54 W (4.5 kV×12 mA) for survey spectra and 144 W (12 kV×12 mA) for high resolution scans. The total pressure in the main vacuum chamber during analysis was typically between $10^{-9}$ and $10^{-8}$ mbar. Survey spectra were acquired at a pass energy of 160 eV. To obtain more detailed information about chemical structure, oxidation states etc., high resolution spectra were recorded from individual peaks at 40 eV pass energy (yielding a typical peak width for polymers of 1.0 eV).

Each specimen was analysed at an emission angle of 0° as measured from the surface normal. Assuming typical values for the electron attenuation length of relevant photoelectrons the XPS analysis depth (from which 95% of the detected signal originates) ranges between 5 and 10 nm for a flat surface.

Data processing was performed using CasaXPS processing software version 2.3.15 (Casa Software Ltd., Teignmouth, UK). All elements present were identified in survey spectra. The atomic concentrations of the detected elements were calculated using integral peak intensities and the sensitivity factors supplied by the manufacturer.

Evaluation of Cellular Responses

L929 mouse fibroblasts (cell line ATCC-CCL-1, Rockville, Md.) were used to investigate cell attachment and spreading on samples. Cells were cultured in minimum essential medium (MEM, Life Technologies, USA) containing 10% (v/v) foetal bovine serum (FBS, Sigma-Aldrich) and 1% (v/v) non-essential amino acids (Life Technologies, USA). Cells were harvested with TrypLE Express (Life Technologies, USA) to produce a single cell suspension. Cells were collected by centrifugation at 300 g for 5 minutes at 4° C. and re-suspended in media at $1\times10^6$ cells/mL of media.

Prior to cell seeding all samples were pre-incubated with a double strength antibiotic-antimycotic solution (Anti-Anti, Life Technologies, USA) in phosphate buffered saline (PBS) for 1 hour at room temperature. Cells were seeded into samples wells along with tissue culture polystyrene (TCPS) control surfaces at $2.5\times10^4$ cells/cm$^2$ and incubated at 37° C., 5% $CO_2$ for 24 hours. Samples were photographed under bright-field using an Olympus IX-71 inverted microscope.

For analysis of cell attachment on polymer materials relative to a TCPS control surface, a MTS assay was employed. Stock solutions of 4 mM, 3-(4,5-dimethylthiazol-2-yl)-5(3-carboxymethoxyphenyl)-2-(4-sulfophenyl)-2H-tetrazolium (MTS, Promega) in PBS and 3 mM of phenazine methosulfate (PMS, Sigma) in PBS were used to make up a mixture of MTS and PMS reagent. A working assay reagent solution was made up by addition of 2 mL of MTS and 100 μL of PMS stock solutions per 10 mL of complete medium. Media was removed from the sample and control wells and washed with 500 μL of fresh medium; subsequently 365 μL of the assay reagent solution was added to wells then incubated for 3 hours at 37° C., 5% $CO_2$.

For colorimetric analysis, plates were read in a BioTek plate reader at wavelengths 490 nm and 655 nm. The difference in readings at the two wavelengths was used to calculate cell attachment compared to TCPS.

Figure 4:
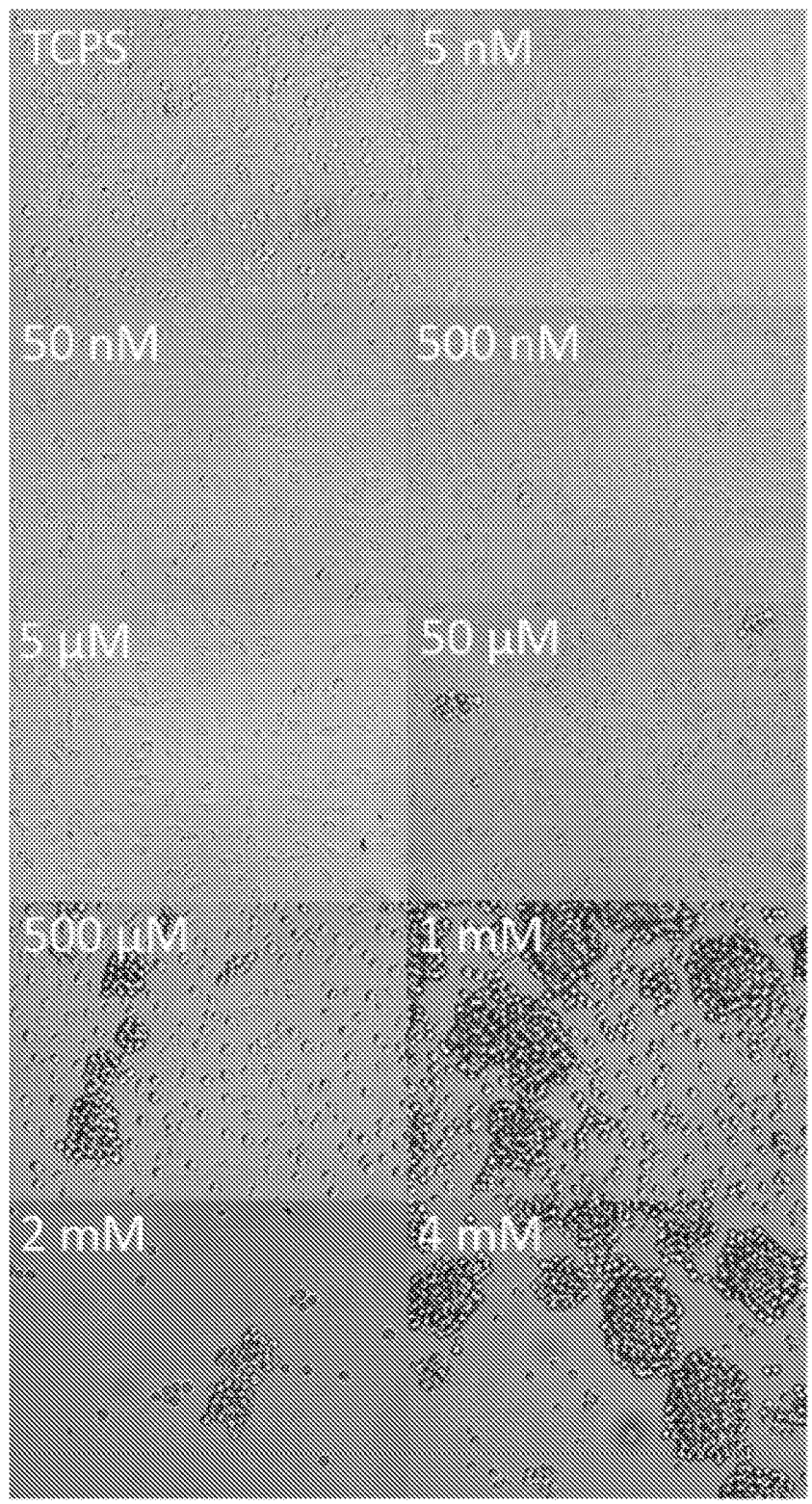
FIG. 4—L929 fibroblast cell attachment on PEGDAP surfaces (various concentrations) after 24 hours compared with attachment on a tissue culture polystyrene (TCPS) control surface.

A study with L929 fibroblasts was conducted to determine the lowest concentration of PEGDGE required to minimise cell attachment to demonstrate the low fouling property of the PEGDAP coatings. L929 fibroblasts were able to significantly adhere and expand onto the treated surfaces up to a PEGDGE concentration of 50 μM, whereby evidence of a small number of rounded cells could be observed (FIG. 4).

A summary of the results is presented below.

Evaluation of Protein Adsorption

The labelling of fibronectin with Europium and the subsequent protein adsorption assay were performed as previously described in Coad, B. R.; Lu, Y.; Meagher, L. *Acta Biomater.* 2012, 8, 608 (the contents of which are incorporated by reference), albeit fibronectin was used instead of human serum albumin. Briefly, 1 nmol fibronectin from human serum (Sigma-Aldrich) in 100 μL of 0.1 M bicarbonate buffer (pH 9.3) was treated with a 15-fold excess of Eu-labelling reagent (Delfia Eu-N1 ITC chelate, Perkin Elmer) at 4° C. for 18 hours. Labelled fibronectin was purified via dialysis. Protein adsorption assay was performed with 10% FBS (fetal bovine serum) in PBS (phosphate buffered saline) supplemented with 0.3 μg/mL Eu-labelled fibronectin (approximately 1/100 of the endogenous fibronectin component of FBS). Wells of 24 well ultra-low attachment (ULA) (Corning Costar, NY, USA) plates, TCPS plates and TCPS plates coated with a polymer coating of this inventions (for example $^2$PEGDAP$_{TCPS}$), were incubated with supplemented FBS solution (140 μL) at 20° C. for 20 hours then washed 5× with PBS and 3× with MilliQ water. Following the final wash, Eu(III)-liberating Enhancement Solution (Perkin Elmer) was added (150 μL) and allowed to incubate with the surfaces for 1 hour. Following incubation, 100 μL of the Eu-complex solution was removed from each well surface and transferred to a white 96-well plate for time-resolved fluorescence assay on a PHERAstar instrument with excitation and the emission measured at 337 and 620 nm, respectively, as per Perkin Elmer product instructions. Standard solutions were used to determine concentrations of Eu(III).

Introduction of Functional Groups onto a Substrate—Allylamine Plasma Treatment

Allylamine plasma coatings were obtained using a custom built reactor according to a previously established procedure published in Griesser H J., *Vacuum*, 39, 485, 1989, the contents of which are incorporated in their entirety by reference. Briefly, tissue culture polystyrene (TCPS) 48 well plates (Thermo-Scientific, Nunc, Roskilde, Denmark) were placed on the lower rectangular electrode of the plasma reactor in a glass chamber (height=350 mm, diameter=170 mm). The distance between the lower and upper electrodes was 150 mm. The allylamine monomer (Sigma-Aldrich, 98%) was degassed 5 times prior to deposition. The deposition was carried out twice for 25 seconds with an initial pressure of 0.2 mbar (200 kHz, 20 W).

Example 1: Making of Polymer Coatings from a First Component of a Polymer (PEG) and a Second Component (Diaminopropane) with Incorporation of a Bioactive Agent (Peptide or Melimine)

Polymer Coating Synthesis

Poly(ethylene glycol) diglycidyl ether (PEGDGE) (Sigma-Aldrich, 6,000 Da) and 1,3-diaminopropane (DAP) (Sigma-Aldrich, ≥99%) were dissolved in MilliQ water to produce a 4 mM PEGDGE-based crosslinking solution (PEGDAP) (PEGDGE:DAP molar ratio of 3:1). The 4 mM stock solution was then diluted to afford solutions of 2 mM, 1 mM, 0.5 mM, 0.05 mM and 0.005 mM of the PEGDAP solution. 175 μL of the stock solution and each dilution thereof were pipetted into 4 wells of a freshly allylamine plasma treated 48 well tissue culture polystyrene (TCPS) plate (the allylamine plasma treatment was carried out as outlined previously). The plate was then covered with a lid and placed in a 60° C. shaker oven overnight. After drying of the solution (18 hours), the plate was immersed in fresh MilliQ water and washed over 5 hours with 5 changes of fresh MilliQ water. Following washing, the now PEGDAP coated tissue culture polystyrene plate (hereafter abbreviated as $^X$PEGDAP$_{TCPS}$ where X denotes the concentration of PEGDAP coating solution in mM placed on the ALAPP coated TCPS) was placed in a laminar flow cabinet to dry and stored prior to use.

In this example, a solution containing poly(ethylene glycol) diglycidyl ether (PEGDGE) and diaminopropane (DAP) (with a PEGDGE:DAP ratio of 3:1) was placed on an allylamine functionalised TCPS surface (ALAPP). The epoxide groups of the PEGDGE react with the amines present on the allylamine coating as well as the DAP in solution, allowing for covalent surface immobilization and crosslinking to take place between the PEG polymers (FIG. 1) since each amine functionality can react with up to two epoxide groups (FIG. 2). The PEGDGE:DAP ratio of 3:1 allows for crosslinking and also provides unreacted epoxide groups resulting from the excess PEGDGE in the solution (FIG. 2). The unreacted epoxide groups are then able to provide conjugation points for amine containing bioactive molecules such as peptides.

Figure 3:
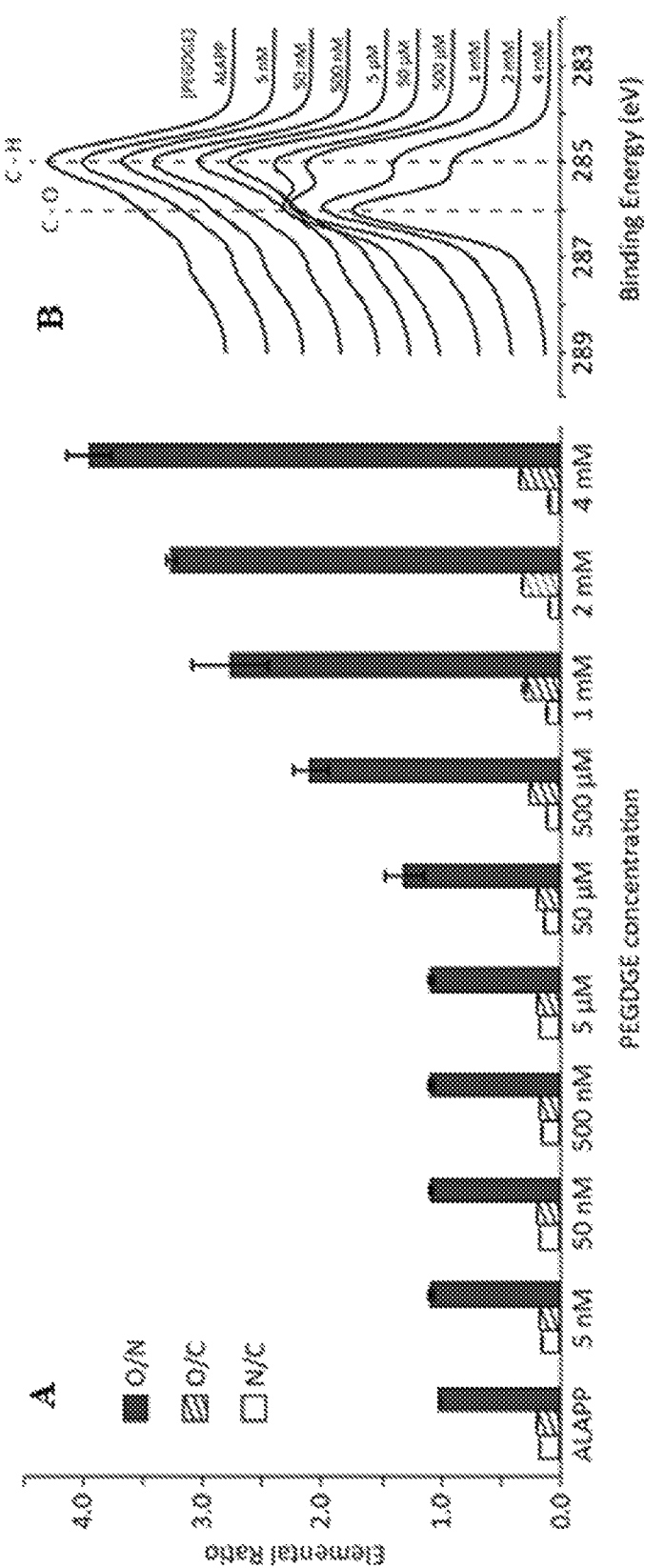
FIG. 3—Image A shows elemental ratios of PEGDAP coatings obtained from XPS analysis at increasing concentrations of PEGDGE; and image B shows XPS C1s high resolution spectra obtained on the same samples.

X-ray photoelectron spectroscopy (XPS) analysis was conducted to determine the effect of the PEGDGE concentration on the amount of PEG immobilised on the allylamine interlayer coating. As the PEGDGE concentration was increased, the O atomic concentration (%) also increased (Table 1), which was reflected on the elemental ratios, as a significant increase in the O/N ratios is observed (FIG. 3 image A). The increase in the O concentration clearly demonstrates the immobilization of PEG on these surfaces due to the high O content present in the PEG polymer.

TABLE 1

Elemental composition of surfaces used in this study as determined by XPS analysis (atomic concentrations in %).

| | ALAPP | 5 nM | 50 nM | 500 nM | 5 µM |
|---|---|---|---|---|---|
| O (%) | 13.6 ± 0.3 | 13.2 ± 0.4 | 13.9 ± 0.2 | 13.3 ± 0.3 | 13.9 ± 0.5 |
| N (%) | 13.4 ± 0.2 | 12.1 ± 0.4 | 12.9 ± 0.2 | 12.2 ± 0.2 | 12.8 ± 0.3 |
| C (%) | 72.9 ± 0.4 | 74.7 ± 0.6 | 73.2 ± 0.1 | 74.5 ± 0.2 | 73.1 ± 0.5 |

| | 50 µM | 500 µM | 1 mM | 2 mM | 4 mM |
|---|---|---|---|---|---|
| O (%) | 14.3 ± 0.7 | 18.8 ± 0.6 | 21.3 ± 1.4 | 22.4 ± 0.9 | 23.8 ± 0.5 |
| N (%) | 10.8 ± 1.7 | 8.9 ± 0.9 | 7.7 ± 1.3 | 6.9 ± 0.4 | 6.0 ± 0.5 |
| C (%) | 74.9 ± 1.0 | 72.3 ± 0.8 | 71.1 ± 0.5 | 70.7 ± 1.37 | 70.2 ± 0.3 |

C1s spectra also confirm the incorporation of PEG in the coating. As seen in FIG. 3, image B, the shoulder corresponding to the C—O bond increases in intensity as the PEGDGE concentration is increased, reaching a maximum at the highest concentration used, 4 mM ($^4$PEGDAP$_{TCPS}$). PEG contains C—O bonds in every repeat unit of the polymer hence the increase in C—O intensity in the C1s spectra correlates well with the effect of the increased PEGDGE concentration.

Use of Bioactive Compounds—Cyclic-Peptide and Melimine

500 µM solutions of the cyclic-peptides cyclo(Arg-Gly-Asp-D-Phe-Lys) (cRGDfK) and cyclo(Arg-Ala-Asp-D-Phe-Lys) (cRADfK) (Peptides International, KY, USA) were prepared in fresh MilliQ water. The 500 µM stock solutions were then twice and ten times diluted to afford 250, 100, 50, 10, 1 and 0.01 µM solutions. cRGDfK and cRADfK were incorporated into the $^2$PEGDAP$_{TCPS}$ coatings using a one-step ($^2$PEGDAP$_{TCPS}$-OS-cRGDfK/cRADfK) and a two-step incubation ($^2$PEGDAP$_{TCPS}$-TS-cRGDfK/cRADfK) procedure.

For $^2$PEGDAP$_{TCPS}$-OS-cRGDfK/cRADfK samples, 175 µL of 2 mM PEGDAP solution was added into the wells of a freshly allylamine plasma treated 48 well TCPS plate. Immediately after, 175 µL of the 500 µM stock solution and the dilutions of the cRGDfk or cRADfK solutions were added to the wells containing the PEGDAP solution. The plate was then placed into a 37° C. shaker oven for 36 hours to allow reaction and drying of the solution. The plate was then washed over 24 hours and used in cell attachment studies.

For $^2$PEGDAP$_{TCPS}$-TS-cRGDfK/cRADfK samples, 175 µL of 2 mM PEGDAP solution was added into the wells of a freshly allylamine plasma treated 48 well TCPS plate and placed in a 60° C. shaker oven overnight (18 hours). The plate was then washed over 5 hours and allowed to dry. 175 µL of the 500 µM cyclic-peptide solutions and the dilutions thereof were placed into the wells of the PEGDAP coated TCPS plate. The plate was then placed in a 37° C. shaker oven for 4 hours. Subsequently the solutions in the wells were aspirated and the wells were washed (5×) with fresh MilliQ water before being used in cell attachment studies.

Melimine (American Peptide Company, CA, USA)—an antimicrobial peptide derived from portions of melittin and protamine (which has the following amino acid sequence: TLISWIKNKRKQRPRVSRRRRRRGGRRRR), was separately incorporated into the PEGDAP coatings in a one-step ($^2$PEGDAP$_{TCPS}$-OS-Mel) and two-step incubation ($^2$PEGDAP$_{TCPS}$-TS-Mel) procedure. A 5 mg/mL solution of melimine was prepared in MilliQ water and incorporated into the PEGDAP coatings in the same manner as cRGDfK and cRADfK. Following washing (24 hours) and drying of the coated wells, the bottom sections of the wells were removed using a 12 mm drill punch. The coated cut-outs were subsequently used in *Staphylococcus aureus* (*S. aureus*) biofilm assays.

FIG. 4 shows the L929 fibroblast cell attachment on the PEGDAP surfaces (present in different concentrations) after 24 hours, compared with attachment on TCPS control surface. Up to a concentration of 50 µM, all L929 fibroblasts are able to adhere and spread on the surfaces. From 500 µM PEGDGE concentration, cells display a more rounded shape and non-adherent cells begin to form clusters. At 2 and 4 mM concentrations, no adherent cells are observed and all cells remain either non-adherent individuals or form non-adherent cell clusters. As the PEGDGE concentration was further increased, the number of clumped/rounded non-adherent cells increased significantly until no adherent cells could be seen for $^2$PEGDAP$_{TCPS}$ and $^4$PEGDAP$_{TCPS}$ surfaces.

The MTS assay was also carried out to confirm these observations (FIG. 5, image A), where a significant drop in cell attachment compared to the control (TCPS) and allylamine surfaces was observed for $^{0.5}$PEGDAP$_{TCPS}$ surfaces, which is then further reduced with increasing concentration up to 2 and 4 mM, whereby cell attachment is minimised. The results of the cell attachment assay correlate well with the results obtained from XPS analysis; higher PEG content in the coatings reduced the attachment of cells on the surfaces.

A summary of the results is also given below in Table 2.

TABLE 2

L929 cell attachment relative to TCPS at various PEGDGE concentrations.

| Surface | Cell attachment relative to TCPS (%) |
|---|---|
| TCPS | 100 ± 0.9 |
| PEGDAP 5 nM | 88.31 ± 1.2 |
| PEGDAP 50 nM | 53.74 ± 0.9 |
| PEGDAP 500 nM | 67.4 ± 7.5 |
| PEGDAP 5 µM | 50.04 ± 0.9 |
| PEGDAP 50 µM | 66.02 ± 8.0 |
| PEGDAP 500 µM | 18.76 ± 4.6 |
| PEGDAP 1 mM | 7.91 ± 2.8 |
| PEGDAP 2 mM | 3.87 ± 0.2 |
| PEGDAP 4 mM | 3.11 ± 0.3 |

The ability of PEG to resist protein adsorption is a significant factor in minimising fouling. The prevention of protein adsorption on surfaces also indicates resistance to the attachment of cells since proteins are not available to be recognized and used by the cells for adherence. To confirm the resistance of protein adsorption by the PEGDAP coating, an assay using europium-labelled fibronectin was conducted on $^2$PEGDAP$_{TCPS}$ surfaces.

Figure 5:
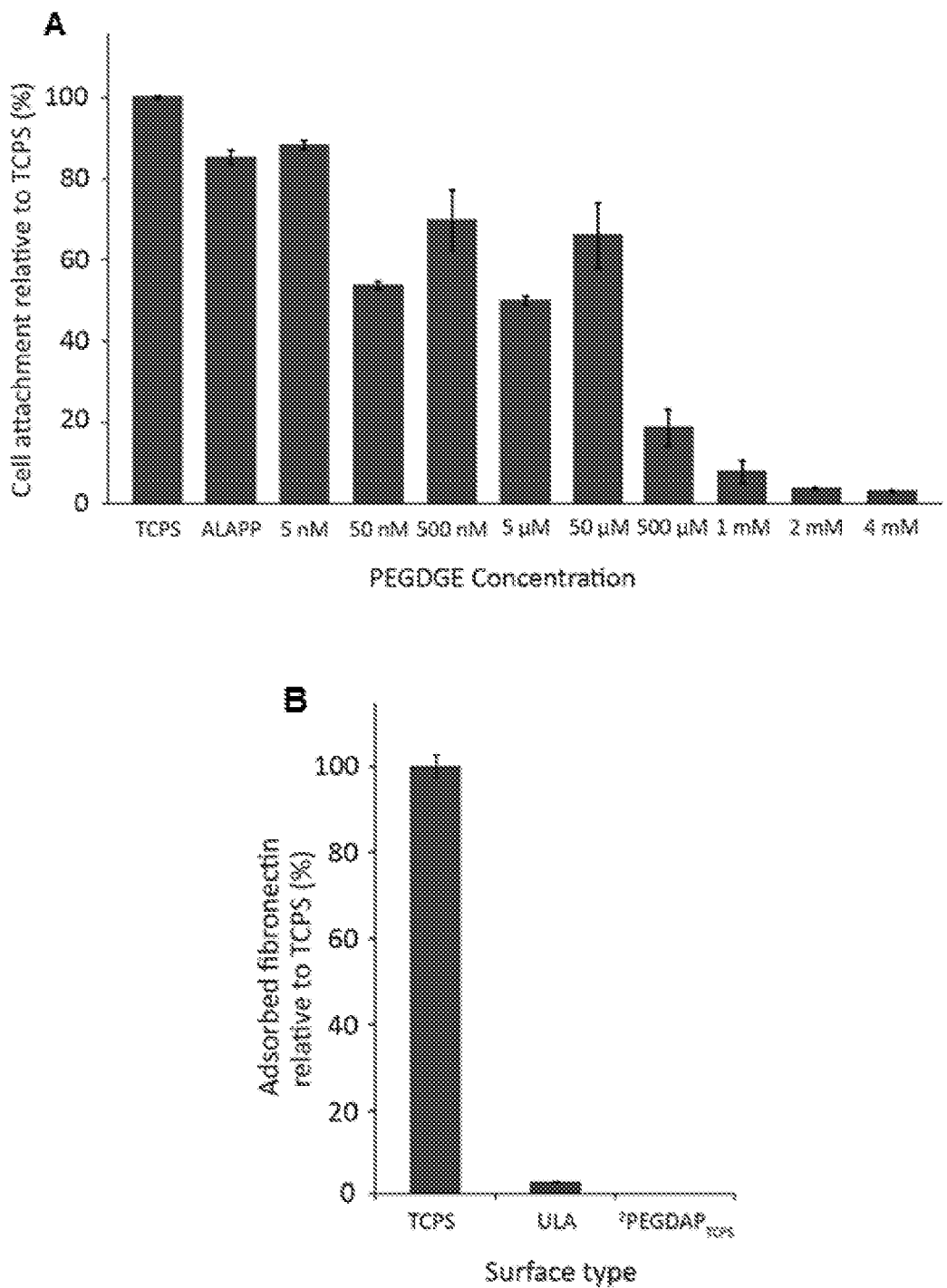
FIG. 5—Image A shows L929 mouse fibroblast attachment after 24 hours relative to TCPS in % obtained via a MTS assay; and image B shows adsorbed fibronectin on test surfaces relative to commercial TCPS and ultra-low attachment (ULA) surfaces as determined by incubation in 10% FBS in PBS, supplemented with Eu-labelled fibronectin, after 20 hours.

Test surfaces were incubated in 10% FBS in PBS supplemented with Eu-labelled fibronectin (c.a. 1% relative to the endogenous fibronectin present in FBS) for 20 hours, washed, and Eu(III) was liberated from the labelled fibronectin. Total fibronectin adsorbed to the test surfaces was calculated based on 620 nm wavelength emission of the liberated Eu(III) from the time-resolved fluorescence measurement. Relative to the TCPS surface, as expected the ULA surface showed a significantly lower fibronectin adsorption, only 3.1%, while an even further reduction was observed for $^2$PEGDAP$_{TCPS}$ with greater than 99.8% lower fibronectin adsorption. This demonstrates that the $^2$PEGDAP$_{TCPS}$ coating is extremely resistant to protein adherence; where the adsorbed protein is at negligible levels (FIG. 5, image B).

The PEGDAP coatings are resistant to non-specific protein adsorption and are able to minimise cell attachment as confirmed by the conducted assays.

A summary of the results is given in Table 3 below.

TABLE 3

Europium labelled fibronectin absorption on surfaces after 20 hours at 20° C.

| Surface | Fibronectin concentration (ng/cm$^2$) | Fibronectin concentration relative to TCPS (%) |
|---|---|---|
| TCPS | 274.1 ± 6.8 | 100 ± 2.5 |
| Corning Costar Ultra-Low Attachment Plate (ULA) | 8.4 ± 0.3 | 3.1 ± 0.1 |
| $^2$PEGDAP$_{TCPS}$ | 0.07 ± 0.1 | 0.03 ± 0.03 |

The reduction of non-specific interactions and the provision of low protein fouling surfaces is also a desired feature in antimicrobial coatings due to the fact that such surfaces can act as a first layer of defence by resisting bacterial attachment. The PEGDAP coating is designed as a low protein fouling platform coating; however this platform also allows the introduction of further layers of defence. The ability to covalently immobilise and display bioactive molecules such as AMPs allows an enhanced resistance towards biofilm formation. Melimine is a synthetic peptide derived from parts of melittin and protamine, which can show excellent bactericidal effects when immobilised onto surfaces. Here, melimine was incorporated into the PEGDAP coating in either a one or a two-step manner, in the same fashion as cRGDfK and cRADfK. The incorporation of the peptide was confirmed via XPS analysis (Table 4, Table 5 and FIG. 7).

Table 4 and Table 5 show the elemental composition and elemental ratios of melimine incorporated surfaces, respectively. A significant increase in the nitrogen and carbon content is observed for $^2$PEGDAP$_{TCPS}$-OS-Mel coatings, compared to the $^2$PEGDAP$_{TCPS}$ coating, as expected from the incorporation of melimine. This is also supported by the reduction in the O/N ratio. For the $^2$PEGDAP$_{TCPS}$-TS-Mel surfaces, even though a significant difference is not observed for the nitrogen content relative to the $^2$PEGDAP$_{TCPS}$, there is an overall increase in the carbon concentration. A larger change in the coating composition is observed for the one-step incorporated $^2$PEGDAP$_{TCPS}$-OS-Mel samples compared to the two-step $^2$PEGDAP$_{TCPS}$-TS-Mel surfaces, since in the one-step samples, the melimine is being incorporated to the bulk of the coating, while the incubation two-step method interacts with the outermost layer of the PEGDAP coating. Allylamine plasma treated interlayer surface (ALAPP) is shown as a reference.

TABLE 4

Elemental composition and elemental ratios of melimine incorporated surfaces.

| | Element (Atomic Concentration %) | | |
|---|---|---|---|
| Surface | O | N | C |
| ALAPP | 13.80 ± 0.09 | 13.40 ± 0.06 | 72.81 ± 0.03 |
| $^2$PEGDAP$_{TCPS}$ | 22.49 ± 0.12 | 6.60 ± 0.09 | 70.86 ± 0.04 |
| $^2$PEGDAP$_{TCPS}$-OS-Mel | 18.48 ± 1.27 | 8.56 ± 0.30 | 72.93 ± 1.00 |
| $^{2S}$PEGDAP$_{TCPS}$-TS-Mel | 19.42 ± 0.03 | 5.71 ± 0.07 | 74.79 ± 0.20 |

TABLE 5

Elemental ratios of melimine incorporated surfaces.

| | Elemental Ratio | | |
|---|---|---|---|
| Surface | O/N | O/C | N/C |
| ALAPP | 1.03 | 0.19 | 0.18 |
| $^2$PEGDAP$_{TCPS}$ | 3.41 | 0.31 | 0.09 |
| $^2$PEGDAP$_{TCPS}$-OS-Mel | 2.15 | 0.25 | 0.11 |
| $^{2S}$PEGDAP$_{TCPS}$-TS-Mel | 3.40 | 0.26 | 0.08 |

Figure 7:
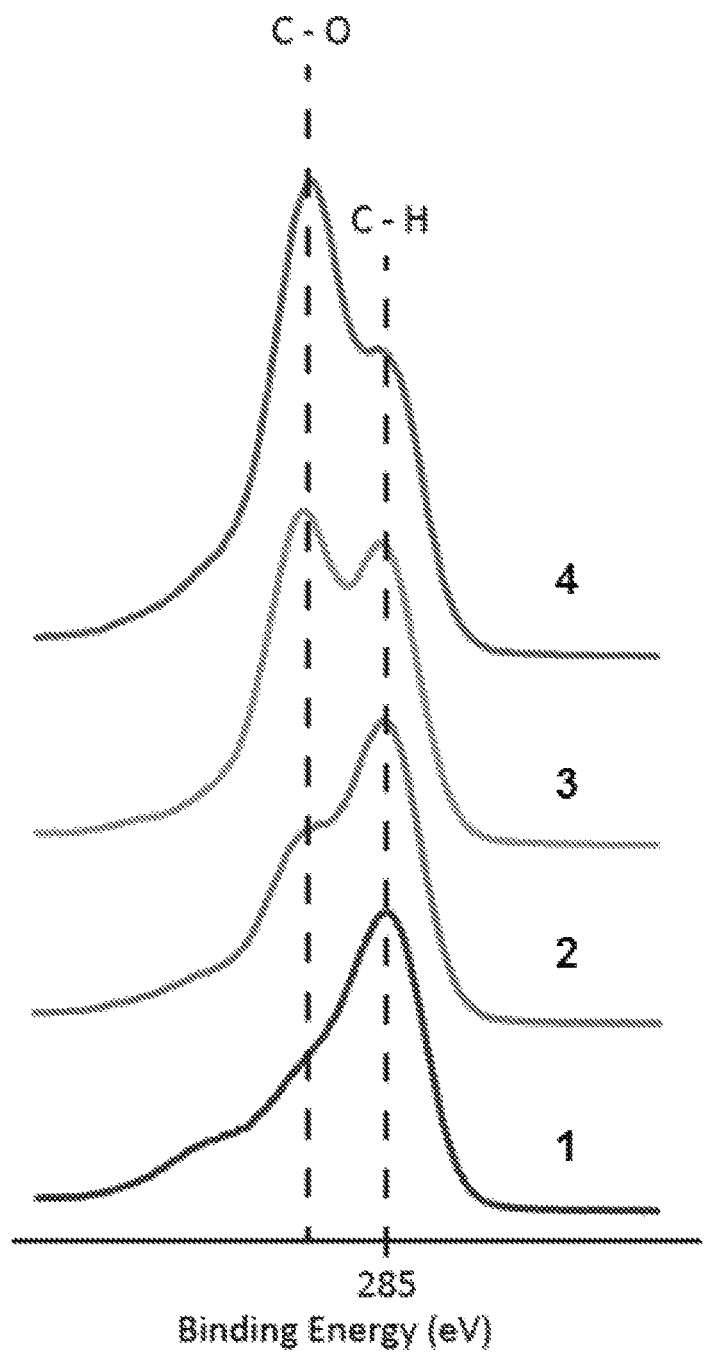
FIG. 7—C1s high resolution spectra demonstrating the effect of melimine incorporation into PEGDAP coatings, wherein: 1 relates to ALAPP; 2 relates to $^2$PEGDAP$_{TCPS}$-OS-Mel; 3 refers to $^2$PEGDAP$_{TCPS}$-TS-Mel; and 4 refers to $^2$PEGDAP$_{TCPS}$.

FIG. 7 shows the C1s high resolution spectra results, demonstrating the effect of melimine incorporation into the PEGDAP coating. A significant increase in the C—H bond intensity is observed relative to the $^2$PEGDAP$_{TCPS}$ surface, when melimine is incorporated, especially with the one-step incorporation ($^2$PEGDAP$_{TCPS}$-OS-Mel). This indicates the conjugation of melimine to the PEGDAP coating. allylamine plasma treated interlayer coating (ALAPP) is shown as a reference.

In order to demonstrate the synergistic effect of the non-adhesive PEGDAP coating and the immobilised melimine, a preliminary biofilm assay using S. aureus was conducted on TCPS control, $^2$PEGDAP$_{TCPS}$, $^2$PEGDAP$_{TCPS}$-OP-Mel and $^2$PEGDAP$_{TCPS}$-TS-Mel surfaces (Table 6). Bacterial strain *Staphylococcus aureus* (S. aureus clinical strain 38) (SA38) was streaked onto chocolate agar (Oxoid, UK) and incubated overnight at 37° C. A single colony was cultured in 10 mL of tryptic soy broth (TSB) (Oxoid, UK) overnight to log phase at 37° C. Optical density of the resulting culture was adjusted to $OD_{660}$ of 0.1 (corresponding to $1 \times 10^8$ cfu/mL) in TSB media (with 0.25% w/v glucose). Bacterial numbers were confirmed by a retrospective viable count. Previously prepared TCPS, $^2PEGDAP_{TCPS}$ and melimine coated ($^2PEGDAP_{TCPS}$-OS-Mel and $^2PEGDAP_{TCPS}$-TS-Mel) cutouts were sterilised with 70% w/v ethanol for at least 1 hour beforehand. For 48 hours adhesion experiments, samples were placed in 2 mL of $1 \times 10^8$ cfu/mL TSB culture containing 0.25% w/v glucose and incubated at 37° C. with shaking for 24 hours, then the media was replaced with fresh TSB (2 mL) and incubated for a further 24 hours (total of 48 hours). The samples were then washed with PBS before examination by fluorescent staining.

Samples used in the *S. aureus* biofilm assay were stained with LIVE/DEAD BacLight Bacterial Viability Kit (Molecular Probes, Inc., OR, USA) as described in the following previous studies: Chen, R., Cole, N., Willcox, M. D. P., Park, J., Rasul, R., Carter, E., Kumar, N. *Biofouling*, 2009, 25, 517; Kirov, S. M., Webb, J. S., O'May, C. Y., Reid, D. W., Woo, J. K. K., Rice, S. A., Kjelleberg, S., *Microbiology*, 2007, 153, 3264; Barraud, N., Hassett, S. A., Hwang, S.-H., Rice, S. A., Kjelleberg, S., Webb, J. S. *J. Bacteriol.*, 2006, 188, 7344; and Chen, R., Willcox, M. D. P., Cole, N., Ho, K. K., Rasul, R., Denman, J. A., Kumar, N. *Acta Biomater.*, 2012, 8, 4371.

Briefly, microscopic observation and image acquisition was performed with Olympus FV1200 Confocal Inverted Microscope. Images obtained from 10 areas on each of duplicate samples for each surface were analysed using ImageJ software. The image analysis results were measured as the average area of cells per field of view and are reported as the average percentage coverage. Prior to comparing the groups, equality of variances was tested using Levene's test. Unequal variances were adjusted by transforming the data using square root transformation. Differences between the groups were analysed using linear mixed model ANOVA, which adjusts the correlation due to repeated observations. Post hoc multiple comparisons were performed using Dunnett T3 comparison for the 48 hour adhesion experiment.

For $^2PEGDAP_{TCPS}$ coated surfaces, a significant reduction of 96.3% in *S. aureus* coverage was observed. A single strategy against biofilm formation can be effective, as is the case for the $^2PEGDAP_{TCPS}$ coating alone, however, in order to maximise the prevention of biofilm formation, the employment of multifunctional strategies can be used. As in the case for $^2PEGDAP_{TCPS}$-OS-Mel surfaces, a further significant reduction in *S. aureus* (99.4%) attachment is observed when melimine was incorporated in a one-step manner. Even though $^2PEGDAP_{TCPS}$-TS-Mel also showed low attachment of *S. aureus* (98.8%), there was no statistical difference in comparison to the $^2PEGDAP_{TCPS}$ coating alone.

TABLE 6

Total surface coverage (%) by *S. aureus* (SA38) on test surfaces following the 48 hour biofilm formation assay.

| TCPS | $^2PEGDAP_{TCPS}$ | $^2PEGDAP_{TCPS}$-OS-Mel | $^2PEGDAP_{TCPS}$-TS-Mel |
|---|---|---|---|
| 14.05 ± 0.92 | 0.52 ± 0.24 | 0.08 ± 0.03 | 0.17 ± 0.02 |

Figure 8:
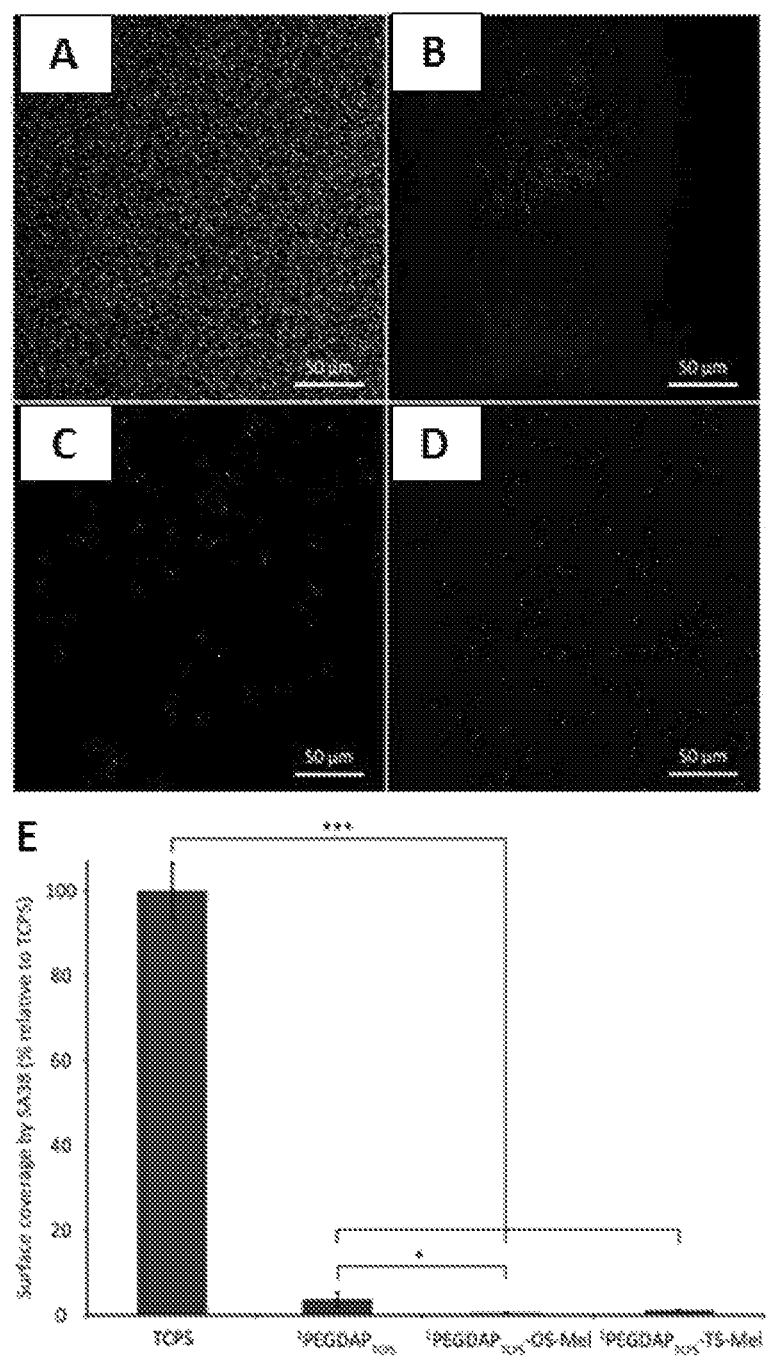
FIG. 8 shows the confocal images of live/dead stained *S. aureus* (SA38) on: A: TCPS; B: $^2$PEGDAP$_{TCPS}$; C: $^2$PEGDAP$_{TCPS}$-OP-Mel; and D: $^2$PEGDAP$_{TCPS}$-TS-Mel. Image E shows the surface coverage of *S. aureus* (SA38) observed on PEGDAP and melimine modified PEGDAP coatings relative to TCPS.

FIG. 8 shows the confocal images of live/dead stained *S. aureus* (SA38) on: A—TCPS; B—$^2PEGDAP_{TCPS}$; C—$^2PEGDAP_{TCPS}$-OP-Mel; D—$^2PEGDAP_{TCPS}$-TS-Mel. Image E Graph shows the surface coverage of *S. aureus* (SA38) observed on PEGDAP and melimine modified PEGDAP coatings relative to TCPS (*=p≤0.05, =p≤0.01, *=p≤0.001, n≥3, error bars represent standard error of the mean).

A summary of these results is given below in Table 7.

TABLE 7

*S. aureus* (SA38) surface coverage relative to TCPS.

| Surface | SA38 surface coverage relative to TCPS (%) |
|---|---|
| TCPS | 100 ± 6.5 |
| $^2PEGDAP_{TCPS}$ | 3.7 ± 1.7 |
| $^2PEGDAP_{TCPS}$-OS-Mel | 0.6 ± 0.2 |
| $^2PEGDAP_{TCPS}$-TS-Mel | 1.2 ± 0.1 |

Functionalization of PEGDAP Coating with Cyclic Peptides

Coatings to control biointerfacial responses, including prevention of bacterial attachment, are designed to present multiple strategies to achieve this control. PEGDAP coating can possess low-fouling capabilities as demonstrated by the cell attachment and protein adsorption assays, but additionally, the coating can be designed to allow facile incorporation of peptides and other amine containing bioactive molecules.

PEGDAP coatings can be prepared with excess PEGDGE to DAP which would allow for free epoxide functional groups to be available (FIG. 2). To demonstrate this, the functional cRGDfK and non-functional cRADfK peptides were incorporated into the PEGDAP coatings in a one-step procedure ($^2PEGDAP_{TCPS}$-OS-cRGDfK/cRADfK) and a two-step incubation ($^2PEGDAP_{TCPS}$-TS-cRGDfK/cRADfK) procedure. Cell attachment studies using L929 cells and subsequent analysis via a MTS assay demonstrated the successful incorporation of the cyclic peptides. The attachment of cells onto $^2PEGDAP_{TCPS}$-OS-cRGDfK and $^2PEGDAP_{TCPS}$-TS-cRGDfK coated surfaces could be observed easily while no significant cell attachment was seen on the cRADfK incorporated surfaces (FIG. 9).

Figure 9:
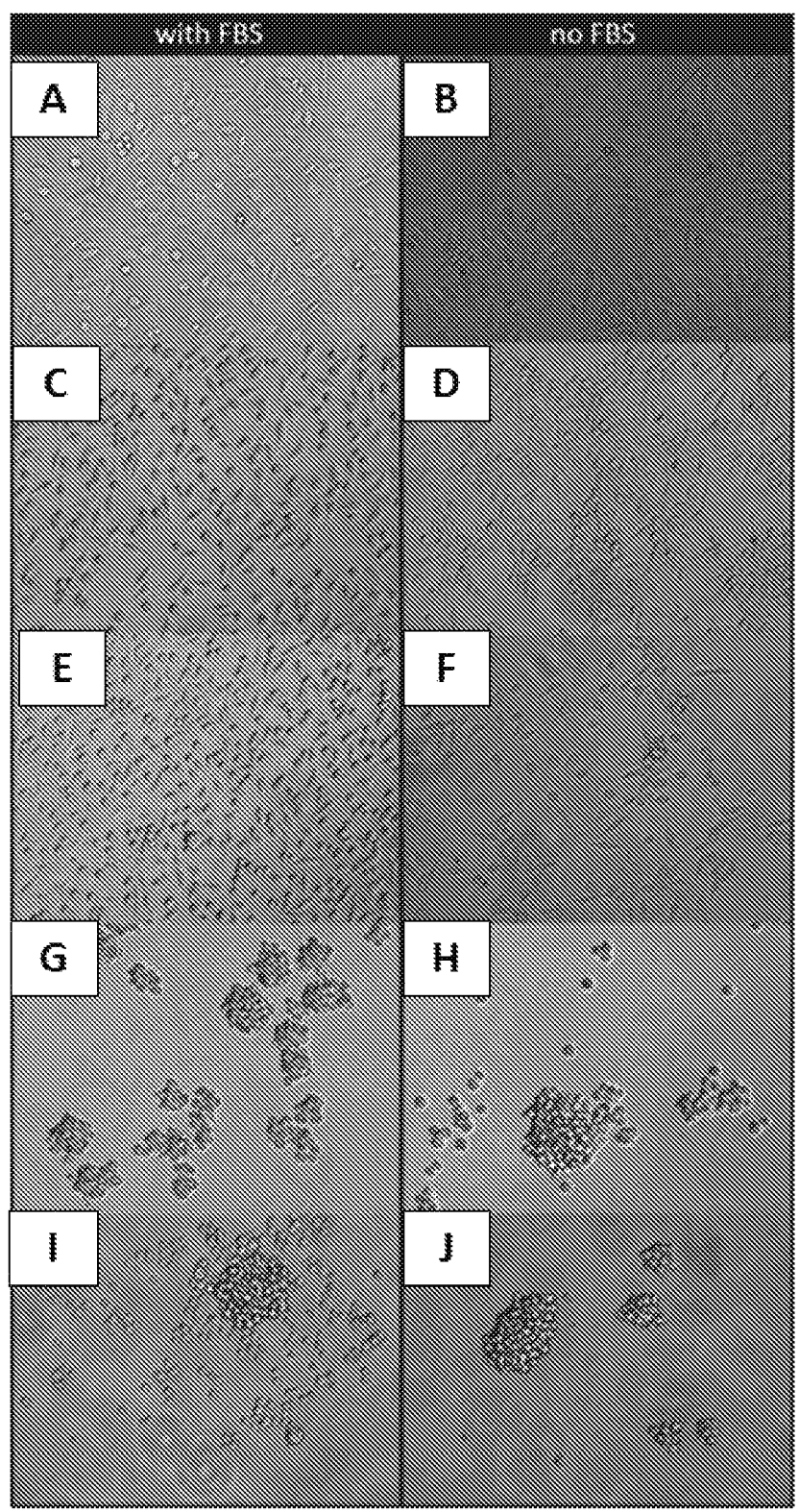
FIG. 9—Cell attachment assay on: images A and B a TCPS surface; images C and D a $^2$PEGDAP$_{TCPS}$-OS-cRGDfK surface; images E and F a $^2$PEGDAP$_{TCPS}$-TS-cRGDfK surface; images G and H a $^2$PEGDAP$_{TCPS}$-OS-cRADfK surface; images I and J a $^2$PEGDAP$_{TCPS}$-TS-cRADfK surface. Cell attachment assays were conducted both in the presence (A, C, E, G, I) and absence (B, D, F, H, J) of fetal bovine serum (FBS).

FIG. 9 shows a cell attachment assay on: images A and B a TCPS surface; images C and D a $^2PEGDAP_{TCPS}$-OS-cRGDfK surface; images E and F a $^2PEGDAP_{TCPS}$-TS-cRGDfK surface; images G and H a $^2PEGDAP_{TCPS}$-OS-cRADfK surface; images I and J a $^2PEGDAP_{TCPS}$-TS-cRADfK surface. Cell attachment assays were conducted both in the presence (A, C, E, G, I) and absence (B, D, F, H, J) of FBS (cyclic-peptide concentration of 500 μM shown). Attachment and spreading of L929 fibroblasts was observed on all cRGDfK containing surfaces while cells remained non-adherent on cRADfK modified surfaces.

Figure 10:
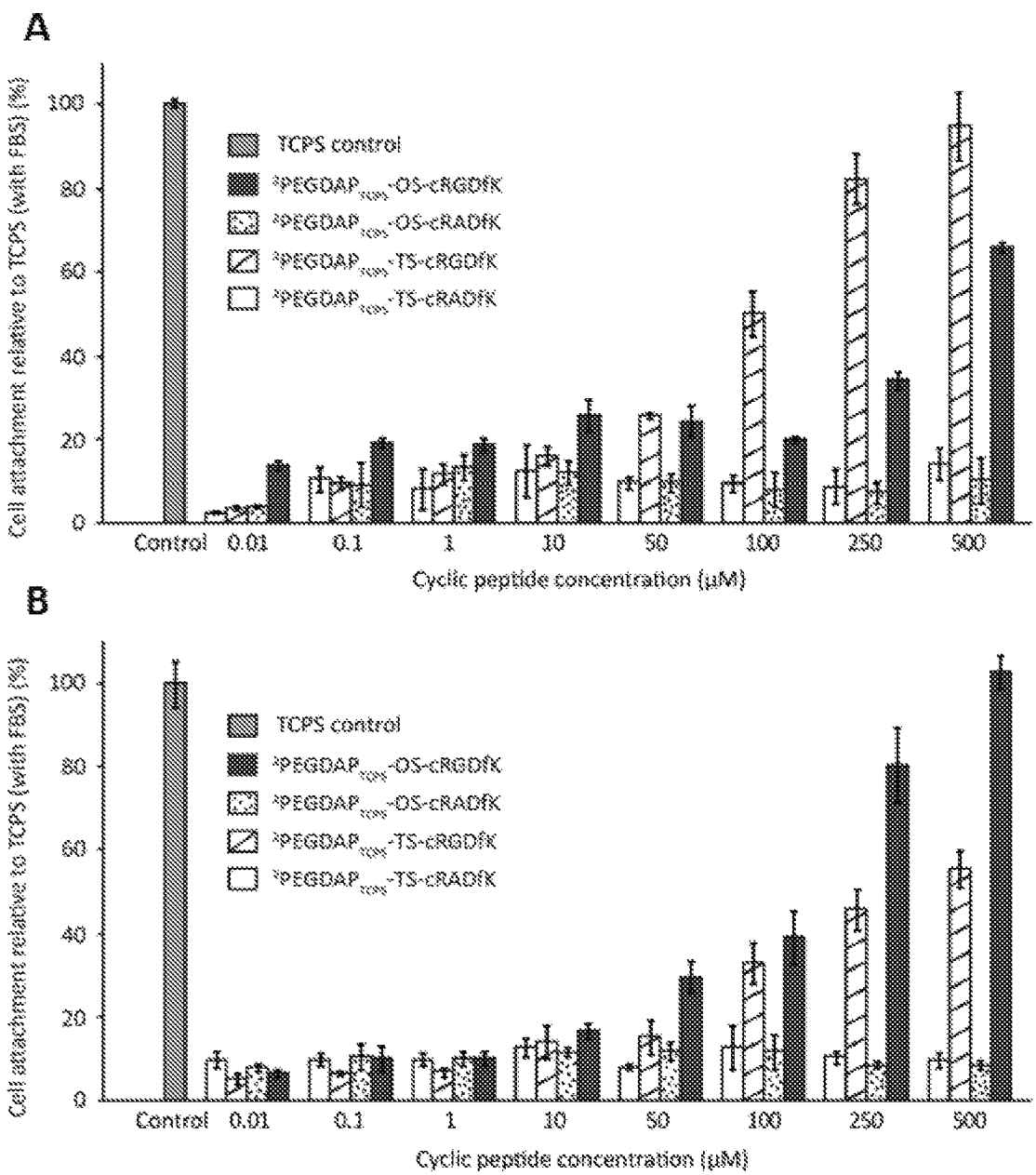
FIG. 10—L929 cell attachment assay for $^2$PEGDAP$_{TCPS}$-OS-cRGDfK/cRADfK and $^2$PEGDAP$_{TCPS}$-TS-cRGDfK/cRADfK surfaces with and without FBS at increasing concentrations of cyclic peptides (images A and B, respectively), relative to TCPS control surface analysed via MTS.

FIG. 10 shows L929 cell attachment assay for $^2PEGDAP_{TCPS}$-OS-cRGDfK/cRADfK and $^2PEGDAP_{TCPS}$-TS-cRGDfK/cRADfK surfaces with and without FBS at increasing concentrations of cyclic peptides (images A and B, respectively), relative to TCPS control surface analysed via MTS (n≥3, error bars represent standard error of the mean).

From the MTS assay (FIG. 10), a concentration dependant cell attachment response was observed for $^2PEGDAP_{TCPS}$-OS-cRGDfK and $^2PEGDAP_{TCPS}$-TS-cRGDfK surfaces in both serum-containing and serum-free media regardless of the incorporation method, whereby with increasing concentration, the number of adherent cells also increased. On the other hand, there were a small number of cells attached on the $^2$PEGDAP$_{TCPS}$-OS-cRADfK and $^2$PEGDAP$_{TCPS}$-TS-cRADfK surfaces at all concentrations of the peptide, but this number was not affected by the incorporation method or the presence of serum. Integrins present in mammalian cell membranes interact specifically with RGD, hence significant L929 attachment was only observed on the cRGDfK incorporated coatings and not the non-biologically active cRADfK counterpart. Based on this, it is possible to see that the cellular interaction with the peptide is specific and that with both the one-step and two-step peptide immobilization methods; the conjugated cRGDfK is biologically active and can be recognized by the cell transmembrane proteins. In the study, both serum-containing and serum-free media were also utilised to demonstrate that the L929 cells were specifically interacting with the conjugated peptide and it was not the result of the proteins present in the FBS containing media.

The facile incorporation of the cRGDfK demonstrates the versatility of the PEGDAP coating to allow for multifunctional properties. In this case cRGDfK was used as a model bioactive to demonstrate the PEGDAP coating's capability for multi-functionality.

Cytotoxicity Studies

Cytotoxicity assessment of materials was performed according to the International Standard ISO10993-5/12, the contents of which are incorporated by reference. Tested surfaces were in the 48 well plate format. Untreated TCPS control surfaces, $^2$PEGDAP$_{TCPS}$ and $^4$PEGDAP$_{TCPS}$ surfaces were incubated with 300 μL per well with complete minimum essential medium (MEM, containing 10% (v/v) FBS and 1% (v/v) non-essential amino acids for 66 hours in a sealed humidified chamber placed on a rocker (Seoulin Mylab™) at 20 rpm at 37° C. in a 5% $CO_2$ incubator.

Media from test wells were removed and serially diluted at 1 in 2 with cell culture medium to afford 50, 25 and 12.5% dilutions. 100 μL aliquots of neat incubated medium and its dilutions were added in quadruplicate to wells previously seeded with L929 cells (18,000 cells per well, 16 hours) in a 96 well plate format. The additional controls added to wells containing pre-seeded cells consisted of medium alone, 5%, and 10% (v/v) dimethylsulfoxide (DMSO, Sigma) in medium. The plate was subsequently incubated for 21 hours (37° C., 5% $CO_2$). An MTS assay was performed to assess cell viability as previously described for cell adhesion studies.

As a coating designed for implantable medical devices, the PEGDAP coating must not be releasing any toxic compounds in a biological environment. In order to determine if any compounds were leaching from the PEGDAP coatings a cytotoxicity study with L929 cells was conducted. In the cytotoxicity study only surfaces with $^2$PEGDAP$_{TCPS}$ and $^4$PEGDAP$_{TCPS}$ coatings were used since these coatings showed the best performance in resisting cell attachment. Initially the test surfaces were incubated in medium for 66 hours at 37° C. Subsequently, previously seeded L929 cells were grown in the presence of the PEGDAP incubated media and their dilutions (50, 25 and 12.5%) for 21 hours. L929 cells were also grown in fresh medium, medium incubated with TCPS and 5 and 10% (v/v) DMSO (in medium) as controls respectively. Following 21 hours incubation, a MTS assay was employed to determine cell viability. All cytotoxicity studies were performed according to the International Standard ISO10993-5/12 (the contents of which are incorporated herein by reference), and cell viability below 70% was considered cytotoxic.

Figure 6:
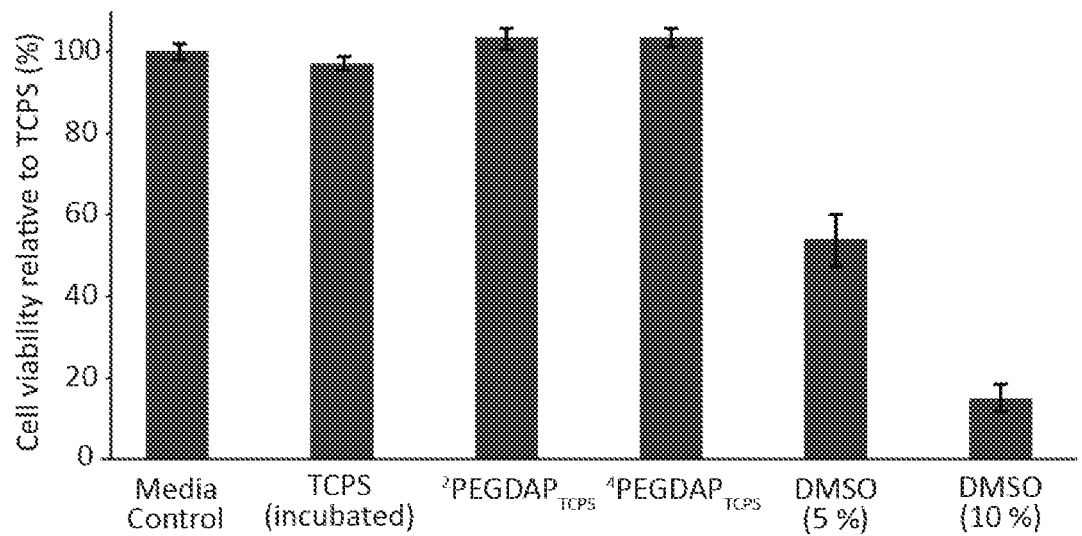
FIG. 6—In vitro cell toxicity assessment in PEGDAP incubated media.

For TCPS incubated medium and the fresh medium controls there was no reduction in cell viability. Conversely, a significant reduction was observed in the case of 5 and 10% DMSO in medium (below 60 and 20%, respectively) as expected (FIG. 6). There was no reduction in cell viability for any of the PEGDAP incubated surfaces regardless of the concentration of the incubated medium. This result follows many other studies demonstrating the non-toxic properties of PEG-based polymer systems both in vitro and in vivo (for example: Ozcelik, B., Brown, K. D., Blencowe, A., Ladewig, K., Stevens, G. W., Scheerlinck, J.-P. Y., Abberton, K., Daniell, M., Qiao, G. G., *Adv Healthc Mater.,* 2014, 3, 1496; Li, B., dong, X., Fang, S., Gao, J., Yang, G., Zhao, H., *Drug Chem Toxicol,* 2011, 34, 208; and Gong, C. Y., Shi, S., Dong, P. W., Yang, B., Qi, X. R., Guo, G., Gu, Y. C., Zhao, X., Wei, Y. Q., Qian, Z. Y., *J Pharm Sci.,* 2009, 98, 4684). Similarly, in the case of PEGDAP coatings no in vitro toxicity was observed.

FIG. 6 shows the results for the in vitro cell toxicity assessment in PEGDAP incubated media. The viability results for neat incubated solutions of $^2$PEGDAP$_{TCPS}$ and $^4$PEGDAP$_{TCPS}$ are shown only, since even at the highest concentration no reduction in cell viability was observed, indicating that the surfaces were substantially non-cytotoxic.

Example 2—Making of Polymer Coatings Utilising a First Component (PEG) and a Second Component (DAP), with Incorporation of a Bioactive Agent (Bioactive Quorum Sensing Inhibitor DHP)

Synthesis of 5-methylene-1-(prop-2-enoyl)-4-(2-fluorophenyl)-dihydropyrrol-2-one (DHP)

DHP was synthesised according to a previously established method (WO 2007085042 and Ho, K. K. K., et al., *Biofouling* 2010, 26, 913, the contents of which are incorporated by reference.

Briefly, 5-hydroxy-5-methyl-4-(2-fluorophenyl)-dihydropyrrol-2-one (0.23 g; 1.11 mmol) was first dissolved in dry dichloromethane (DCM) (10 mL) and dry tetrahydrofuran (THF) (1 mL), followed by addition of triethylamine (1.5 mL; 10.76 mmol) and a few crystals of hydroquinone while stirring and cooling in an ice bath. A solution of acryloyl chloride (1 mL; 9.56 mmol) in DCM (3 mL) was added dropwise over 10 min. The mixture was stirred further for 3 hours and the solvent was removed under vacuum. The residue was chromatographed on silica gel using DCM to yield the di-acrylate product as a pale yellow solid (0.18 g; 50%).

The di-acrylate product was then dissolved in dry DCM (4.5 mL), followed by the addition of trifluoroacetic acid (0.5 mL). This mixture was stirred at room temperature for 2 hours and the resultant solution was washed twice with saturated sodium bicarbonate solution. The product was then purified by chromatography using DCM as the eluent to yield 5-methylene-1-(prop-2-enoyl)-4-(2-fluorophenyl)-dihydropyrrol-2-one (DHP) as an off-white solid. (74 mg; 55%)

Melting point: 121-122° C.

$^1$H NMR δ ($CDCl_3$): 7.18-7.55 (m, 4H, ArH), 6.66 (d, 1H, =CH—), 6.54-6.61 (dd, 1H, =$CH_2$), 6.24 (s, 1H, H3), 5.91-5.95 (d, 1H, =$CH_2$), 5.25 (d, 2H, =$CH_2$).

PEGDAP Coating and Incorporation of DHP

Poly(ethylene glycol) diglycidyl ether (PEGDGE) (Sigma-Aldrich, 6,000 Da) and 1,3-diaminopropane (DAP) (Sigma-Aldrich, ≥99%) were dissolved in MilliQ water to produce a 2 mM PEGDGE-based crosslinking solution (PEGDAP) (PEGDGE:DAP molar ratio of 2:1 or 1:1). DHP was dissolved in ethanol to afford a 3 mg/mL solution; this solution was also diluted to 1.5 mg/mL concentration. DHP was incorporated into the PEGDAP coatings in a one-step or two-step procedure.

For the one-step incorporation 175 µL of the 2 mM PEGDAP (both 2:1 and 1:1) solutions were pipetted into the wells of a freshly allylamine plasma treated 48 well TCPS plate (the allylamine plasma treatment was carried out as outlined previously). Subsequently 175 µL of the 3 mg/mL and 1.5 mg/mL DHP solutions were respectively added to the to the PEGDAP solution containing wells. The lids of the containers were covered and the plates were placed in a 60° C. shaker oven overnight for the drying of the solutions (18 hours). The plates were then immersed in fresh MilliQ water and washed over 5 hours with 5 changes of fresh MilliQ water, followed by ethanol washing over 3 hours with 5 changes of fresh ethanol.

DHP was also incorporated into the PEGDAP coatings via a two two-step procedure, using incubation and drying methods. Initially PEGDAP background coatings were prepared via the placement of 175 µL of the 2 mM PEGDAP solutions (both 2:1 and 1:1) into the wells of a freshly allylamine plasma treated 48 well TCPS plate. The lids of the plates were covered and the solution was allowed to evaporate overnight (18 hours). Once dry, the plates were washed in fresh MilliQ water over 5 hours with 5 changes of fresh MilliQ water, and then allowed to dry in air. Subsequently, 175 µL of 3 mg/mL DHP solution were pipetted into the wells of the PEGDAP coated plates. For the drying method, the plate was placed into a shaker oven at 60° C. until dry for 6 hours. For the incubation method, the plate was covered, sealed and placed on an orbital shaker for 24 hours. Subsequently both the plates were washed with fresh MilliQ water over 5 hours with 5 changes of fresh MilliQ water followed by ethanol washing over 3 hours with 5 changes of fresh ethanol. The plates were then allowed to dry in air in a laminar flow cabinet.

The prepared surfaces were labelled as follows: $^X$PEGDAP-DHP-$Y_Z$- where X denotes the PEGDGE:DAP ratio, Y denotes the coating preparation procedure (OS: one-step, ITS: incubated two-step, and DTS: dried two-step) and Z denotes the DHP concentration in mg/mL.

For L929 cell attachment assays, the plates were used as prepared. For 48 hours *Staphylococcus aureus* and *Pseudomonas aeruginosa* bacterial adhesion assays, the bottom sections of the wells were removed using a 12 mm drill punch and the cut-out disks were used in the assays.

In this study, allylamine monomer was used in the plasma treatment of tissue culture polystyrene surfaces to introduce amine functional groups. Subsequently, solutions containing poly(ethylene glycol) diglycidyl ether (PEGDGE) and diaminopropane (DAP) (with a PEGDGE:DAP ratio of 2:1 or 1:1) was dispensed onto the allylamine plasma coated (ALAPP) tissue culture polystyrene (TCPS) surfaces. The epoxide groups of the PEGDGE is able to react with the amines present on the allylamine coating as well as the DAP in solution, allowing for covalent surface immobilisation and crosslinking to take place between the PEG polymers (FIG. 11) since each amine functionality can react with up to two epoxide groups. In addition, the use of epoxy-amine chemistry provides the advantages of not relying on initiators, catalysts or an inert atmosphere. The PEGDGE:DAP ratio of 2:1 and 1:1 allows for crosslinking and also provides secondary and/or unreacted amine groups. These amine species are then able to provide conjugation points for amine reactive molecules such as acrylates or epoxides.

The 5-methylene-1-(prop-2-enoyl)-4-(2-fluorophenyl)-dihydropyrrol-2-one (DHP) was modified to introduce an acrylate functional groups. Using this acrylate group and a Michael Addition, the compound can be attached to an amine functionalised surfaces. The acrylate functional group of the DHP allows for Michael addition reactions to take place with primary as well as secondary amine functional groups.

When the PEGDAP coating was prepared via the crosslinking of PEGDGE and DAP, primary and secondary amines are available for the acrylate group of the DHP to react with. According to the incorporation procedure utilised, DHP can be immobilised during or after the coating preparation. The DHP can be incorporated into the coating. This demonstrates how the methods disclosed herein are versatile, and allow the incorporation of a bioactive compound, such as the antimicrobial DHP, into a low fouling coating while retaining the bioactivity of the bioactive compound.

FIG. 11 shows the preparation of the PEGDAP coating and the incorporation of DHP using one or two-step methods. As shown, a TCPS substrate was treated by allylamine plasma polymer (ALAPP) deposition to provide an amine functionalised surface. The ALAPP interlayer was then exposed to PEGDGE and diaminopropane, and DHP in either a one-step or two-step process.

X-ray photoelectron spectroscopy (XPS) analysis was conducted to determine the successful PEG coating of the ALAPP coated TCPS substrates and the incorporation of DHP into the coating. As seen in Table 8, the incorporation of the PEGDAP coating onto the ALAPP interlayer led to a significant increase in the oxygen (O) content of the surfaces, since every PEG repeat unit contains an oxygen atom. DHP utilised in this study possesses a single fluorine atom in its structure, hence identification of its presence in the coating is made convenient since no other coating precursor contains fluorine atoms. From the XPS survey analysis it was possible to determine that in all DHP treated surfaces, a significant amount of fluorine is present. In addition, the effect of different incorporation methods on the fluorine content, hence directly the DHP content of the coatings can be observed. As shown in Table 8, the highest F concentration was observed for $^{1:1}$PEGDAP-DHP-OS$_3$ and $^{1:1}$PEGDAP-DHP-OS$_{1.5}$ surfaces. This is quite well expected since the DHP is being immobilised during the crosslinking of the coating allowing the DHP to be incorporated uniformly throughout the coating. For the two-step incorporation methods, a significant, yet smaller F content for the coatings is shown. Since in the two-step methods, the PEGDAP coating is pre-formed, the DHP interacts with the free amine functionalities available near the surface of the coating.

The coatings were prepared with PEGDGE:DAP ratios of 1:1 and 2:1 to determine if the amount of diamine crosslinker impacted upon the extent of DHP incorporation. As seen in Table 8, for both $^{1:1}$PEGDAP-DHP-OS$_3$ and $^{1:1}$PEGDAP-DHP-OS$_{1.5}$ surfaces, a significantly larger F content was observed compared to their 2:1 counterparts. In the $^{1:1}$PEGDAP coatings, the amount of diamine crosslinker was doubled. This allows for more conjugation points for DHP especially for the one-step coatings, where the amine functionalities are available directly during the coating process. However, this trend was not observed for the two-step coatings, as the availability of free amine functional groups is reduced once the crosslinking has already taken place and the coating is washed.

Figure 12:
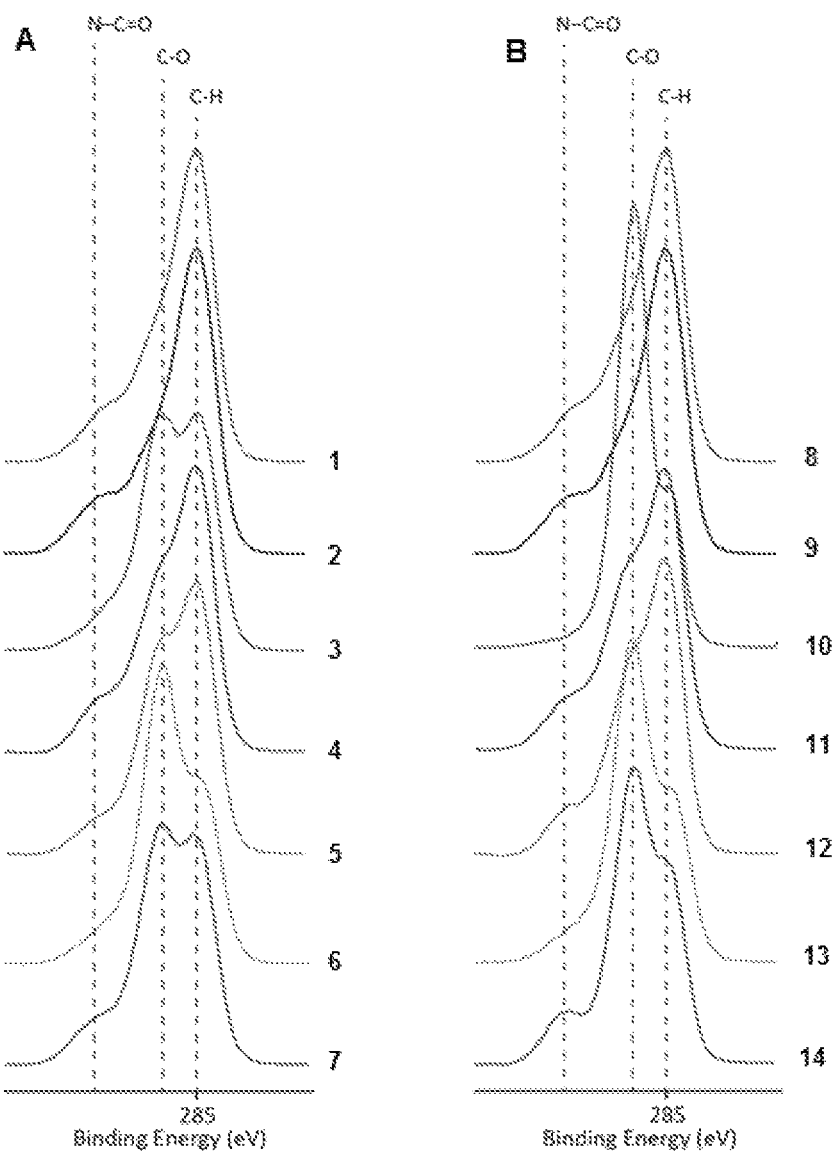
FIG. 12—A comparison of C1s high resolution spectra for $^{1:1}$PEGDAP (image A) and $^{2:1}$PEGDAP (image B) coatings, and the respective DHP incorporated coatings.

Analysis of the C1s high resolution spectra also supports the incorporation of the DHP into the coatings. FIG. 12 shows the comparison of ALAPP, 1:1PEGDAP and $^{2:1}$PEGDAP, C1s high resolution spectra to their respective DHP incorporated counterparts. For the ALAPP-DHP surface, an increase in the N—C=O shoulder of the C1s spectra can be observed, which corresponds to the acrylate group of the DHP. An increase in the C—H peak for all of the one-step incorporated PEGDAP samples can be observed compared to the control PEGDAP coating following DHP incorporation. However, the C—O region corresponding to PEG remains, which was not observed in the ALAPP surfaces. In addition, the N—C=O shoulder becomes more prominent especially for the OS and DTS surfaces where the DHP concentration is high.

XPS analysis of the PEGDAP-DHP coatings successfully demonstrate that DHP can be incorporated into the coatings and the incorporated amount can be controlled using one or two-step methods. This in turn demonstrates that other bioactive compounds may be incorporated using any of the incorporation methods disclosed herein, dependant on compound properties such as solubility and molecular weight.

TABLE 8

Elemental composition of surfaces as determined by XPS (atomic concentrations in %) (n ≥ 3). The surfaces are labelled as follows: $^X$PEGDAP-DHP-Y$_Z$ - where X denotes the PEGDGE:DAP ratio, Y denotes the coating preparation procedure; (OS: one-step, ITS: incubated two-step, and DTS: dried two-step) and Z denotes the DHP concentration in mg/mL.

| Surface | O (%) | N (%) | C (%) | F (%) |
|---|---|---|---|---|
| ALAPP | 13.4 ± 0.1 | 12.5 ± 0.1 | 74.0 ± 0.1 | 0.1 ± 0.0 |
| ALAPP + DHP | 14.8 ± 0.2 | 10.6 ± 0.4 | 73.6 ± 0.2 | 1.1 ± 0.1 |
| $^{1:1}$PEGDAP | 22.8 ± 2.6 | 4.5 ± 2.1 | 72.6 ± 0.5 | 0.0 ± 0.0 |
| $^{2:1}$PEGDAP | 19.6 ± 0.1 | 8.3 ± 0.0 | 72.1 ± 0.2 | 0.0 ± 0.0 |
| $^{1:1}$PEGDAP-DHP-OS$_3$ | 17.2 ± 0.2 | 5.0 ± 0.1 | 73.9 ± 0.2 | 3.9 ± 0.1 |
| $^{2:1}$PEGDAP-DHP-OS$_3$ | 18.5 ± 0.4 | 6.5 ± 0.3 | 72.9 ± 0.3 | 2.2 ± 0.3 |
| $^{1:1}$PEGDAP-DHP-OS$_{1.5}$ | 16.9 ± 0.1 | 5.0 ± 0.2 | 74.4 ± 0.2 | 3.7 ± 0.1 |
| $^{2:1}$PEGDAP-DHP-OS$_{1.5}$ | 16.0 ± 0.4 | 7.5 ± 0.3 | 74.8 ± 0.2 | 1.8 ± 0.0 |
| $^{1:1}$PEGDAP-DHP-ITS$_3$ | 30.1 ± 2.5 | 3.0 ± 1.2 | 66.2 ± 1.1 | 0.7 ± 0.2 |
| $^{2:1}$PEGDAP-DHP-ITS$_3$ | 24.2 ± 1.4 | 6.3 ± 0.5 | 68.8 ± 0.9 | 0.7 ± 0.1 |
| $^{1:1}$PEGDAP-DHP-DTS$_3$ | 26.4 ± 2.0 | 3.3 ± 0.9 | 68.7 ± 0.9 | 1.5 ± 0.2 |
| $^{2:1}$PEGDAP-DHP-DTS$_3$ | 23.8 ± 0.7 | 3.8 ± 0.3 | 69.6 ± 0.2 | 2.8 ± 0.2 |

Cell Attachment Studies

L929 mouse fibroblasts (cell line ATCC-CCL-1, Rockville, Md.) were used to investigate cell attachment and spreading on samples.

PEG can be utilised for many biomedical applications including drug delivery and tissue engineering; all of them relying on the ability of PEG to resist non-specific protein adsorption. The reduction of non-specific biointerfacial interactions is also a desired feature in the context of antimicrobial coatings, since this property can provide a first layer of defence by resisting bacterial attachment. In this example the composition of the coating was altered by the incorporation of DHP. In order for the PEGDAP-DHP coatings to perform as a multifunctional coating, neither the low-fouling, nor the QS inhibiting property of the coating should be hindered. To determine if the incorporation of DHP negatively impacts upon the low-biofouling properties of the PEGDAP-DHP coatings, a cell attachment assay with L929 fibroblasts was conducted.

Figure 13:
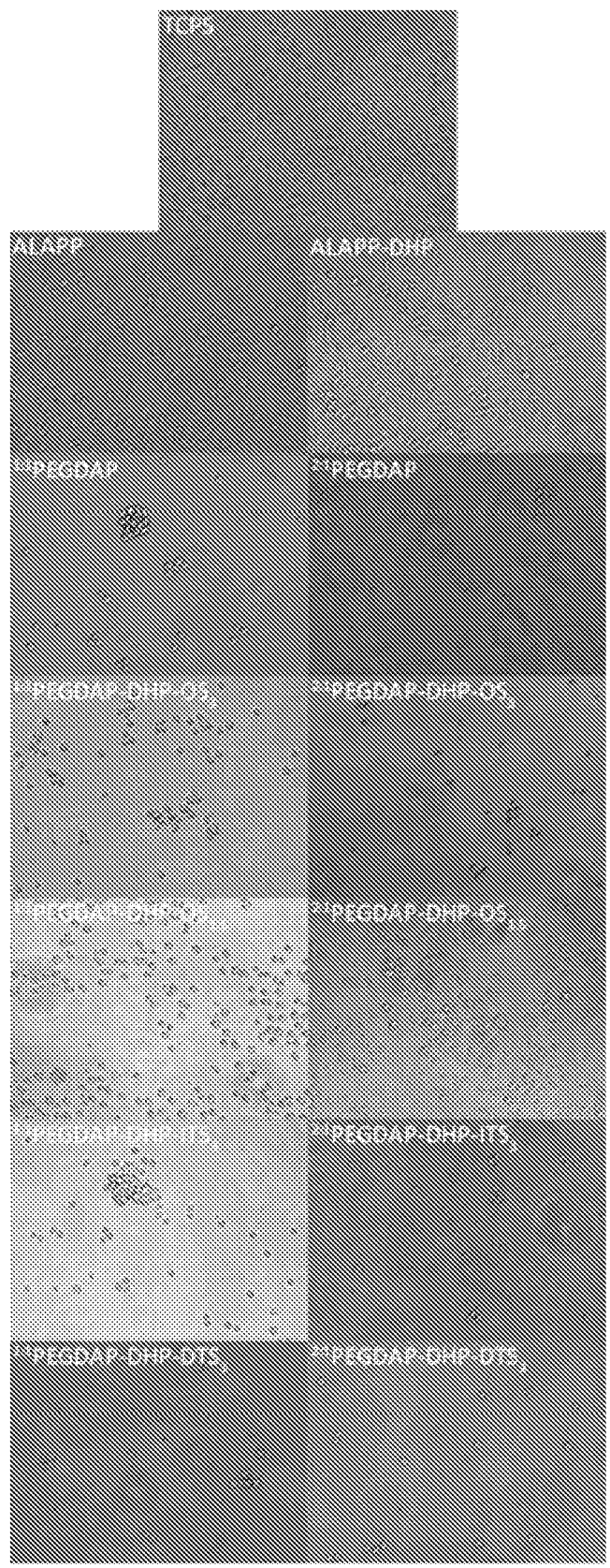
FIG. 13—L929 fibroblast cell attachment on PEGDAP-DHP surfaces observed after 24 hours by phase contrast microscopy compared with attachment on TCPS control surface.

FIG. 13 shows L929 fibroblast cell attachment on PEGDAP-DHP surfaces observed after 24 hours by phase contrast microscopy compared with attachment on a TCPS control surface. Cell spreading was not observed on any of the PEGDAP and PEGDAP-DHP surfaces, indicating that DHP incorporation does not interfere with the low biofouling properties of the PEGDAP coating. While L929 fibroblasts were able to significantly adhere and expand on the TCPS and ALAPP treated surfaces, the cells remained non-adherent and aggregated together on the control PEGDAP surfaces. With the incorporation of DHP, regardless of the incorporation procedure, the cells remained rounded non-adherent (FIG. 13).

Figure 14:
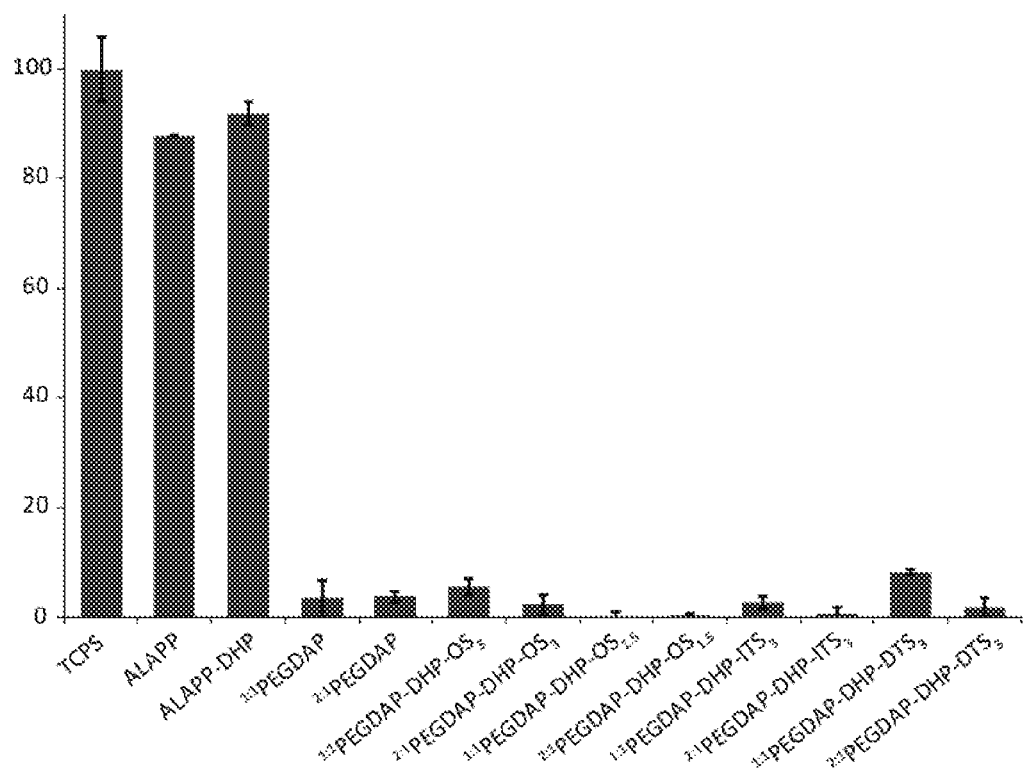
FIG. 14 shows the L929 mouse fibroblast attachment on surfaces after 24 hours relative to TCPS in % obtained via a MTS assay.

FIG. 14 shows the L929 mouse fibroblast attachment on surfaces after 24 hours relative to TCPS in % obtained via a MTS assay. All of the PEGDAP-based coatings displayed low cell attachment, including after DHP incorporation. The MTS assay further confirms the microscopic observations also, whereby a greater than 97% reduction in cell attachment was observed for all the PEGDAP samples with/without DHP. Overall, the cell attachment study demonstrates that immobilisation of DHP within and on the PEGDAP coatings does not hinder the low-biofouling and cell attachment resistant capabilities of the coating.

Cytotoxicity Studies

Cytotoxicity assessment of materials was performed according to the International Standard ISO10993-5/12, the contents of which are incorporated by reference. Tested surfaces were in a 48 well plate format. Untreated TCPS control surfaces and PEGDAP-DHP coated surfaces were incubated with 300 μL per well with complete minimum essential medium (MEM, containing 10% (v/v) FBS and 1% (v/v) non-essential amino acids for 66 hours in a sealed humidified chamber placed on a rocker (Seoulin Mylab™) at 20 rpm at 37° C. in a 5% $CO_2$ incubator.

Media from test wells was removed and serially diluted at 1 in 2 with cell culture medium from neat to afford 50, 25 and 12.5% dilutions. 100 μL aliquots of neat incubated medium and its dilutions were added in quadruplicate to wells previously seeded with L929 cells (18,000 cells per well, 16 hours) in a 96 well plate format. Additional controls were added to wells containing pre-seeded cells; medium alone, 5%, and 10% (v/v) dimethylsulfoxide (DMSO, Sigma) in medium. The plate was subsequently incubated for 21 hours (37° C., 5% $CO_2$). An MTS assay was performed to assess cell viability as previously described for cell adhesion studies.

Any medical device that is to be implanted in patients must not be releasing any toxic compounds towards mammalian cells. The same applies to the coatings that prepared onto these medical devices. The PEGDAP-DHP coatings are designed for such applications and hence they need to conform to the same standards.

In order to determine if any adverse compound was leaching from the PEGDAP-DHP coatings, a cytotoxicity study with L929 cells was conducted. In the cytotoxicity study, all of the PEGDAP and PEGDAP-DHP coatings were tested. Initially the test surfaces were incubated in complete medium for 66 hours at 37° C. Subsequently, the incubated media and its dilutions (50, 25 and 12.5%) were placed on previously seeded L929 cells and the cells were incubated for 21 hours. L929 cells were also grown in fresh medium, medium incubated with TCPS and 5 and 10% (v/v) DMSO (in medium) as controls respectively. Following 24 hours incubation, a MTS assay was employed to determine cell viability. Cell viability below 70% was considered cytotoxic.

Figure 15:
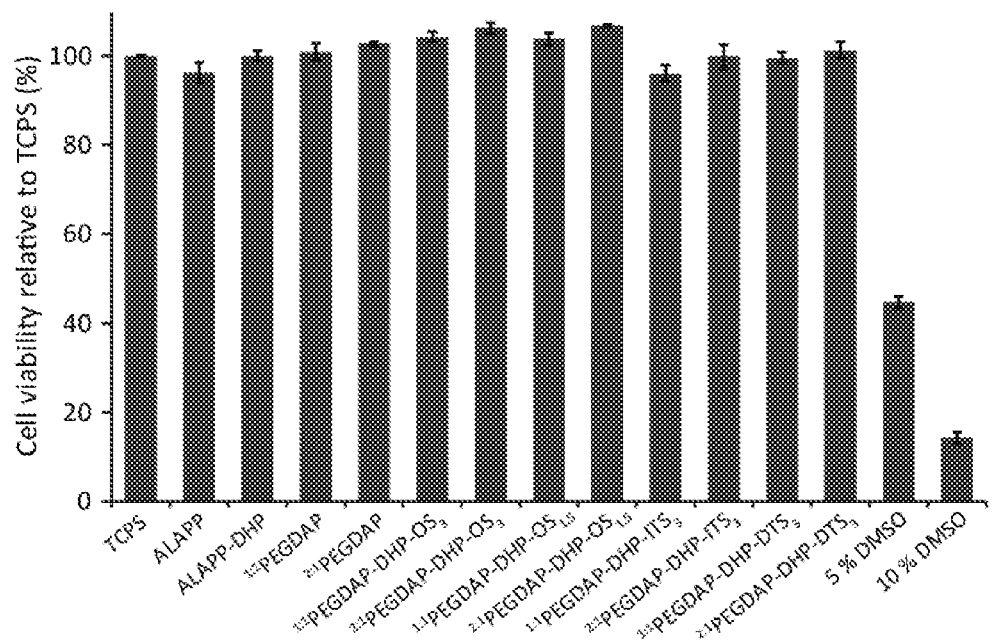
FIG. 15 shows the in vitro cell viability assessment of PEGDAP incubated medium samples in a cytotoxicity study.

FIG. 15 shows the in vitro cell viability assessment of PEGDAP incubated medium samples. No reduction in cell viability was observed for any of the PEGDAP and PEGDAP-DHP coatings. For TCPS incubated media and the fresh medium controls no reduction in cell viability was observed. On the other hand, a significant reduction was observed in the case of 5 and 10% DMSO in medium (below 45 and 15%, respectively) as expected. There was no reduction in cell viability for any of the PEGDAP and PEGDAP-DHP incubated surfaces regardless of the PEGDGE:DAP ratio and the DHP incorporation method, indicating that these surfaces were substantially non-cytotoxic.

Overall this demonstrates that the non-cytotoxic properties of the PEGDAP coatings and the DHP are retained when combined into a single coating.

*Staphylococcus aureus* and *Pseudomonas aeruginosa* Biofilm Assays and Detection of Quorum Sensing The strains of bacteria used for this study were *Staphylococcus aureus* (*S. aureus* strain 38) and *Pseudomonas aeruginosa* (*P. aeruginosa* MH602 harbouring the lasB-gfp (ASV) fusion plasmid (outlined in Ho, K. K. K., et al., *Biomaterials* 2014, 35, 2336). These strains were streaked onto Luriae Bertani (LB) agar and incubated overnight at 37° C. A single colony was cultured overnight in 10 mL of tryptone soya broth (TSB; Oxoid, UK) medium at 37° C. The resulting bacteria were collected by centrifugation and re-suspended in the same volume of TSB twice. Optical density of the resulting culture was adjusted to $OD_{660}$=0.1 ($10^8$ CFU/mL) in TSB. For *P. aeruginosa* MH602, gentamicin was added to the adjusted culture to a final concentration of 40 µg/mL. Previously prepared sample cutouts, were disinfected with 70% w/v ethanol/water and air-dried before being placed individually in 12-well plates, followed by addition of 3 mL of the bacterial suspension. The plates were incubated at 37° C. with shaking at 120 rpm for 24 hours. The surfaces were then gently rinsed twice with phosphate buffered saline (PBS) to remove non-adherent bacteria before examination by fluorescent microscopy.

For *S. aureus*, 38 samples with adherent bacteria prepared as described above were stained with Live/Dead BacLight Bacterial Viability Kits L-7007 (Molecular Probes, Inc, Eugene, Oreg.) according to the manufacturer's procedure. Briefly, 2 µL of the two components were mixed thoroughly in 1 mL of PBS. 10 µL of the solution were then trapped between the sample and the glass microscopy slide and allowed to incubate at room temperature in the dark for 15 min. For the *P. aeruginosa* MH602 QS reporter assays, samples were immersed in 1 mL of PBS containing 2 mL/mL Hoechst 33342 dye for 1 hour. The samples were observed and imaged with an Olympus FV1200 Confocal Inverted Microscope. The laser intensity was adjusted and thereafter kept constant throughout the duration of the experiment. Images from 10 representative areas on each of duplicate samples for each surface were taken.

All confocal images were analysed using ImageJ software, which measured the area fraction covered by green (live) or red (dead) cells (for *S. aureus*) or by blue (Hoechst positive, total cells) or green (Gfp expressing) cells (for *P. aeruginosa*) in the field of view. The results are mean values of three independent experiments.

Data were analysed by the one-way analysis of variance (ANOVA) using IBM SPSS Statistics software (version 22). Differences between the groups were analysed using post hoc Dunnett's T3 test, and results with $p<0.05$ were considered significant.

The PEGDAP-DHP coatings are designed to resist biofilm formation on surfaces by combining low-fouling and QS inhibiting properties of PEG and DHP. Even though L929 cell attachment studies demonstrated the excellent low fouling capability of the PEGDAP-DHP coatings, the ultimate test lies in bacterial biofilm assays. Hence, 24 hour biofilm assays with *S. aureus* and *P. aeruginosa* were conducted on the PEGDAP-DHP coated TCPS cutouts. Subsequently fluorescent microscopy was utilised to determine bacterial coverage and biofilm formation on the test surfaces.

Figure 16:
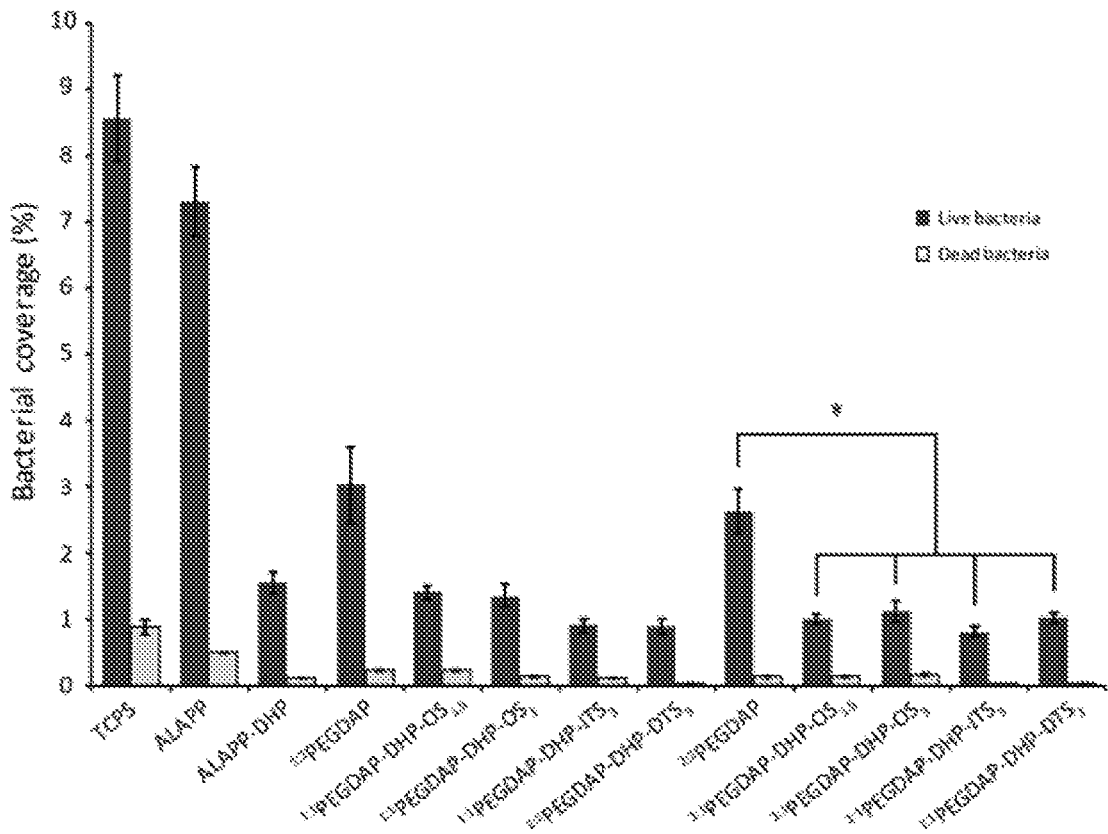
FIG. 16—Bacterial surface coverage on PEGDAP and PEGDAP-DHP surfaces using with *S. aureus* SA38 (*=p≤0.05).

Extensive bacterial colonisation was observed on the surfaces of control TCPS, and ALAPP by both *S. aureus* and *P. aeruginosa* (FIG. 16). There was no significant difference between the blank TCPS control and the ALAPP samples for either bacterium ($p>0.05$). The treatment with DHP and PEGDAP significantly reduced the adhesion of both *S. aureus* and *P. aeruginosa* (FIG. 16). Direct immobilisation of DHP on the ALAPP (ALAPP-DHP) surfaces alone, demonstrated that DHP remained active after immobilisation with a reduction of bacterial adhesion of 80 and 82% for *S. aureus* and *P. aeruginosa*, respectively.

For *S. aureus*, control TCPS and ALAPP cutouts exhibited high bacterial coverage (FIG. 16) with extensive biofilm formation across the sample surfaces. Both the control PEGDAP coatings (2:1 and 1:1 PEGDGE:DAP ratio) and all of the DHP incorporated surfaces showed a significant reduction in bacterial adhesion and biofilm formation compared to TCPS and ALAPP coated surfaces (FIG. 16). For the $^{1:1}$PEGDAP-DHP surfaces, no significant difference ($p>0.05$) was observed compared to the control $^{1:1}$PEGDAP surfaces with an average of 81% decrease in surface coverage in comparison to TCPS and ALAPP. All of $^{2:1}$PEGDAP-DHP surfaces showed an excellent reduction in biofilm coverage with an average of 88% decrease compared to TCPS and ALAPP. Furthermore, an additional 38% reduction in bacterial coverage, compared to the $^{2:1}$PEGDAP control surface was observed, indicating that the incorporation of DHP into the $^{2:1}$PEGDAP coatings further enhanced resistance to *S. aureus* adhesion and biofilm formation. Importantly, there was no significant increase in the proportion of dead bacteria for any of the modified surfaces, indicating that the coating does not induce killing of the bacteria. Such non-bactericidal approach is advantageous as it does not impose strong selective pressure on bacteria that is observed for many antibiotics and therefore it is less likely that resistance will develop to these coatings.

Figure 17:
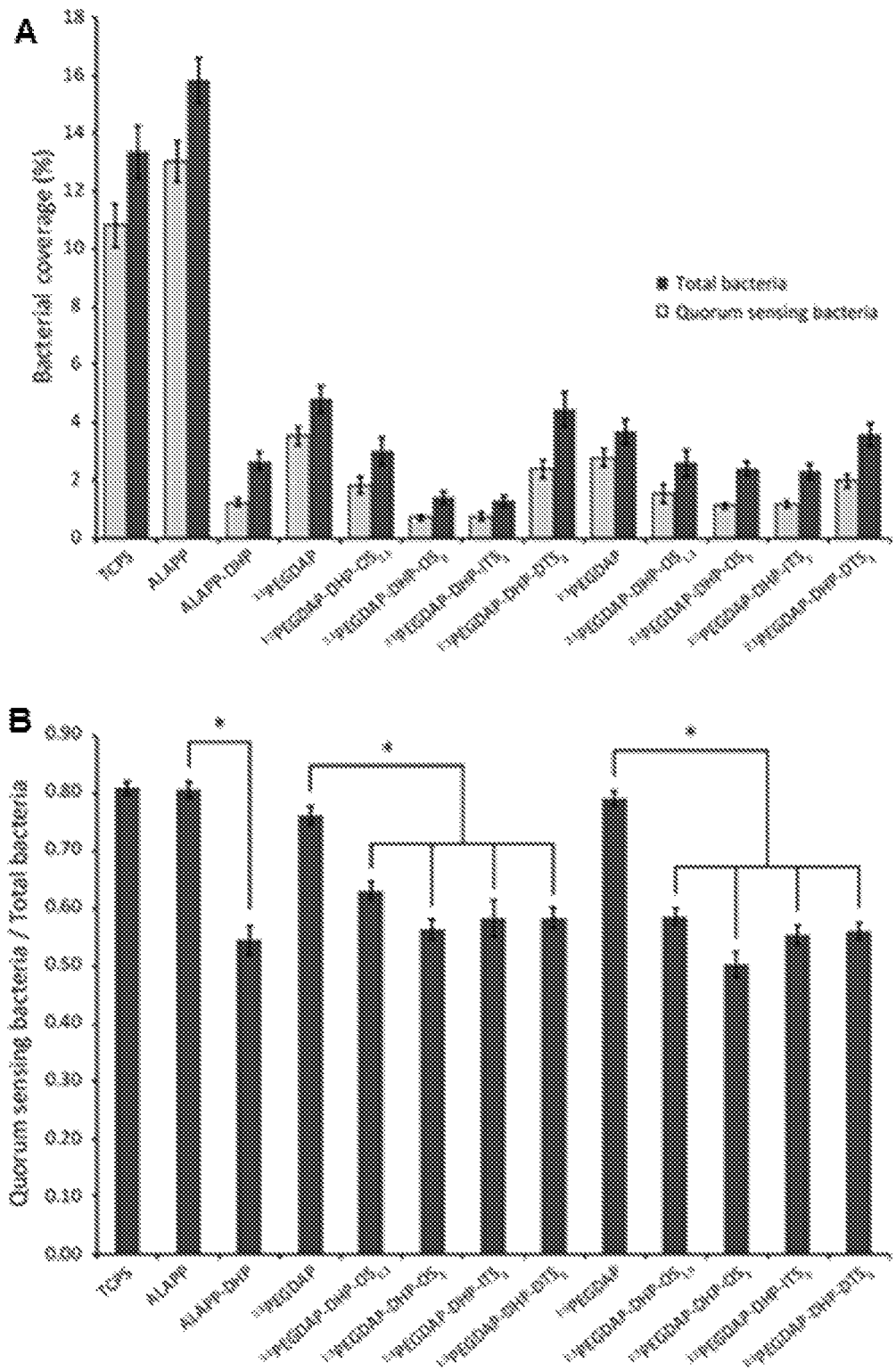
FIG. 17—Bacterial surface coverage on PEGDAP and PEGDAP-DHP surfaces with *P. aeruginosa* MH602 (image A) and ratio of quorum sensing bacteria to total bacterial coverage for *P. aeruginosa* MH602 (*=p≤0.05) (image B).
Figure 18:
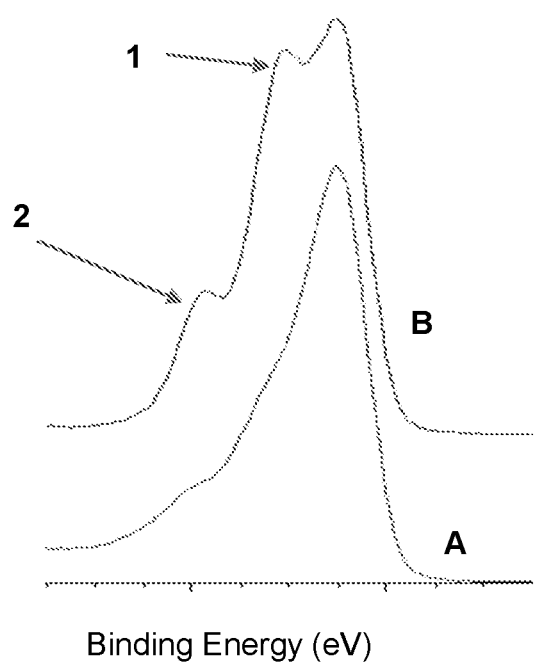
FIG. 18—C1s High resolution XPS Spectra of: an ALAPP surface (line A); and PEG-HPA coating following immobilisation and crosslinking on ALAPP surface (line B). Peak 1 shows the PEGDGE component and Peak 2 shows the HPA component.

For *P. aeruginosa* MH602, lasB-gfp(ASV) fusion plasmid provides resistance to gentamicin, hence gentamicin was added to the adjusted culture to a final concentration of 40 µg/mL to eliminate any cells that are not harbouring the fusion plasmid. For *P. aeruginosa*, significant bacterial coverage was observed on both TCPS and ALAPP coated cutouts. All of the PEGDAP and PEGDAP-DHP surfaces showed a reduction (80%) in bacterial coverage compared to the TCPS and ALAPP surfaces (FIG. 17, image A). For the DHP incorporated surfaces, a significant difference in the total number of bacteria was not observed in comparison to the control PEGDAP surfaces, indicating that the incorporation of DHP did not further enhance the resistance to *P. aeruginosa* attachment on the PEGDAP-DHP surfaces. The *P. aeruginosa* strain MH602 used in this study harbours the lasB-gfp(ASV) fusion plasmid, which allows for the identification of QS. Although, the total number of bacteria on the PEGDAP-DHP surfaces was not statistically different from the control PEGDAP surfaces, a significant reduction in the number of QS bacteria was observed for all of the DHP incorporated surfaces (FIG. 17, image B). The ratio of QS cells to the total cell number in FIG. 17, image B, demonstrates this reduction clearly. Such a reduction indicates the combination with PEGDAP did not hinder the QS activity of the DHP.

Overall, the immobilisation of the DHP within the PEGDAP coatings regardless of the incorporation method did not hinder the biological activity of DHP. While a further reduction in the number of bacteria was observed for S. aureus with the $^{2:1}$PEGDAP-DHP surfaces, the QS inhibiting property of the DHP was demonstrated via the P. aeruginosa QS reporter assay for all DHP incorporated surfaces, demonstrating both the low fouling, and QS inhibiting property of the coatings.

Similar studies were performed with other bacterial on other coatings using the same methodology as above. The results of these are summarised in Table 9.

TABLE 9

Biofilm formation on surfaces relative to TCPS (100%).

| Bacterial strain | HPA | $^2$PEGDAP$_{TCPS}$ |
|---|---|---|
| S. aureus (ATCC 25923) | 0.0 ± 0.2 | 0.0 ± 0.6 |
| S. epidermidis (RP62a) | 0.0 ± 0.03 | 0.4 ± 0.2 |
| E. faecalis (ATCC 29212) | 0.0 ± 0.1 | 4.0 ± 0.1 |
| P. aeruginosa (ATCC 27853) | 3.27 ± 0.1 | 3.9 ± 0.3 |

Example 3: Making of Polymer Coatings from a First Component (PEG) and a Second Component (polyHPA) with Incorporation of a Bioactive Agent which is a Model Compound (TFEA) Representing a Bioactive Synthesis of Poly(N-Hydroxypropyl Acrylamide) Via Reversible Addition Fragmentation Chain Transfer (RAFT) Polymerisation and Chain End Functionalization N-hydroxypropyl acrylamide was polymerised using the RAFT polymerisation technique to produce poly(N-hydroxypropyl acrylamide) (polyHPA). The chain ends of the polyHPA were then modified using methods known in the art to produce polyHPA-NH$_2$.

Synthesis of a Coating

The polyHPA-NH$_2$ was combined with a poly(ethylene glycol) diglycidyl ether (PEGDGE) of g PEGDGE (500 Da) and polyHPA-NH$_2$ (synthesised via RAFT, 13.5 kDa) solution (1:1 molar ratio) (in H$_2$O) is then allowed to evaporate on a treated TCPS substrate at 60° C. for 18 hours.

The surface was then thoroughly washed for further characterisation.

Analysis of PolyHPA-NH$_2$ and PEGDGE Coating

Figure 19:
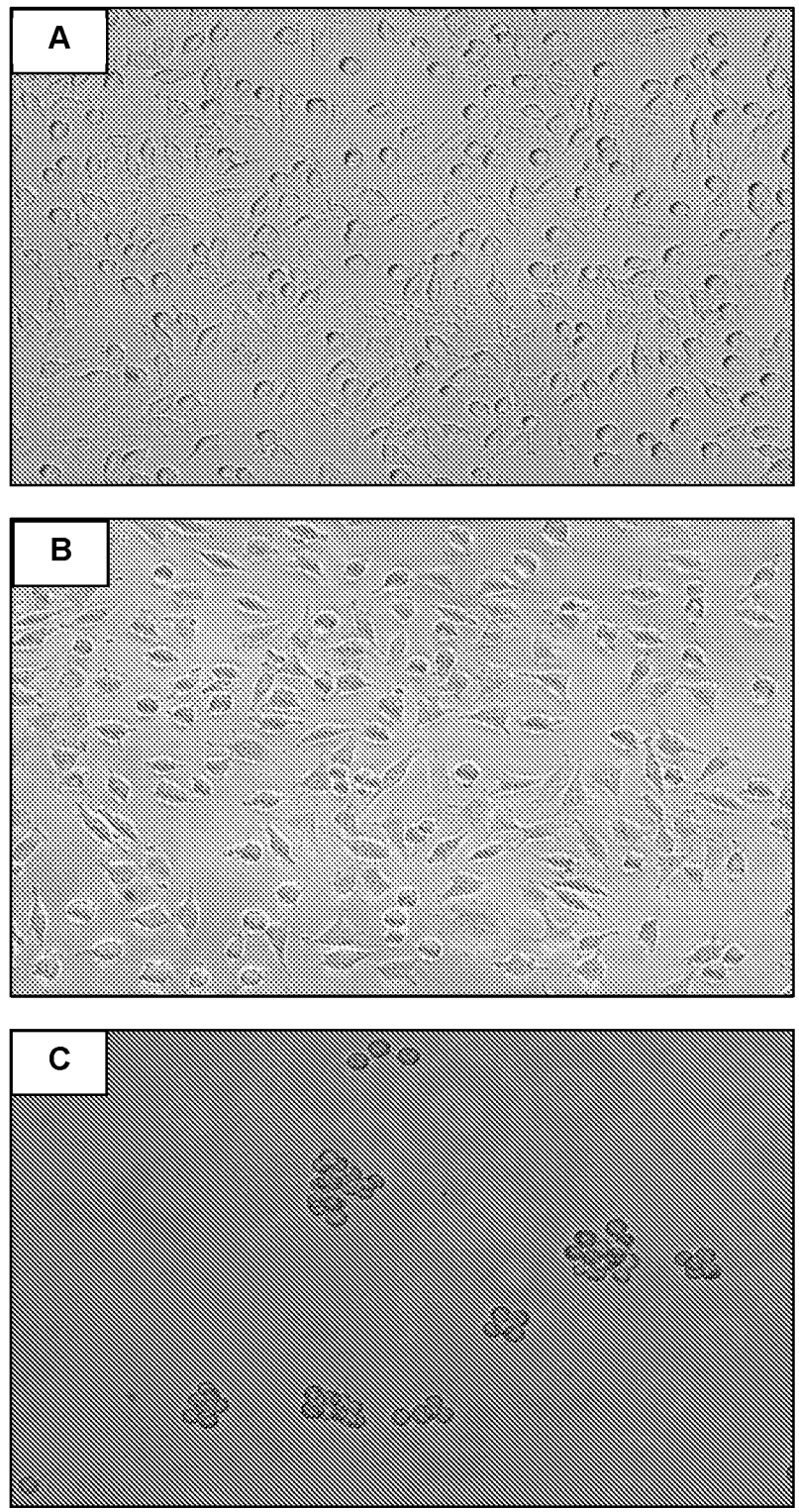
FIG. 19—Bright field microscopy images of a 24 hours cell attachment studies comparing TCPS (image A), allylamine treated (image B) and PEGDGE-polyHPA-NH$_2$ surface (image C).

A cell attachment study was conducted on the PEGDGE-PolyHPA-NH$_2$ surfaces. The results are shown in FIG. 19. In contrast to the TCPS and allylamine surfaces, the no adherent cells are observed and all cells remain either non-adherent individuals or form non-adherent cell clusters.

Figure 20:
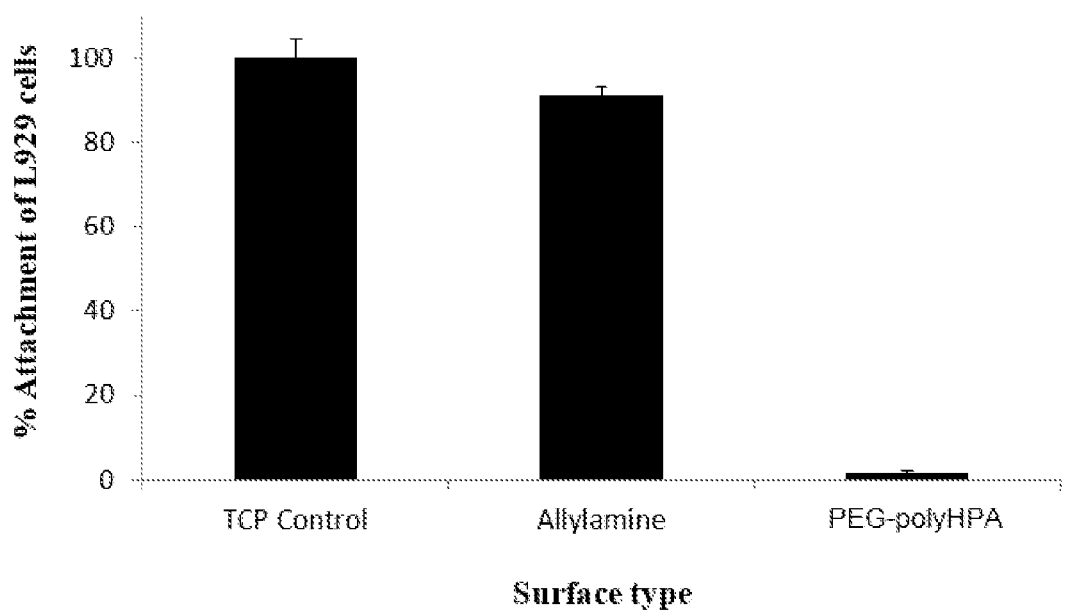
FIG. 20—Results of a MTS assay analysis of polyHPA-NH$_2$ and PEGDGE surfaces following 24 hours incubation with L929 fibroblasts showing the significantly low attachment properties of the coating.

A MTS assay (in accordance with the previously recited conditions) was used to determine cell attachment (FIG. 20). A comparison between the control, the allylamine surface following initial treatment of the TCPS and the coated substrate shows a significant decrease in cell attachment.

A preliminary biofilm assay using S. epidermidis was also conducted. The results are shown in Table 10.

TABLE 10

Preliminary biofilm assay using S. epidermidis.

| Test surface | Crystal Violet OD (S. epidermidis) |
|---|---|
| Negative Control (Tryptic Soy Broth - TSB) | 0.116 ± 0.01 |
| Positive Control (TCPS) | 1.480 ± 0.15 |
| PHA-PEG | 0.109 ± 0.01 |

Incorporation of a Model Compound.

In order to demonstrate how the present process could be utilised for incorporating compounds, such as bioactive molecules, a coating comprising PEG and polyHPA was produced wherein 2,2,2-trifluoroethylamine (TFEA) was incorporated.

Figure 21:
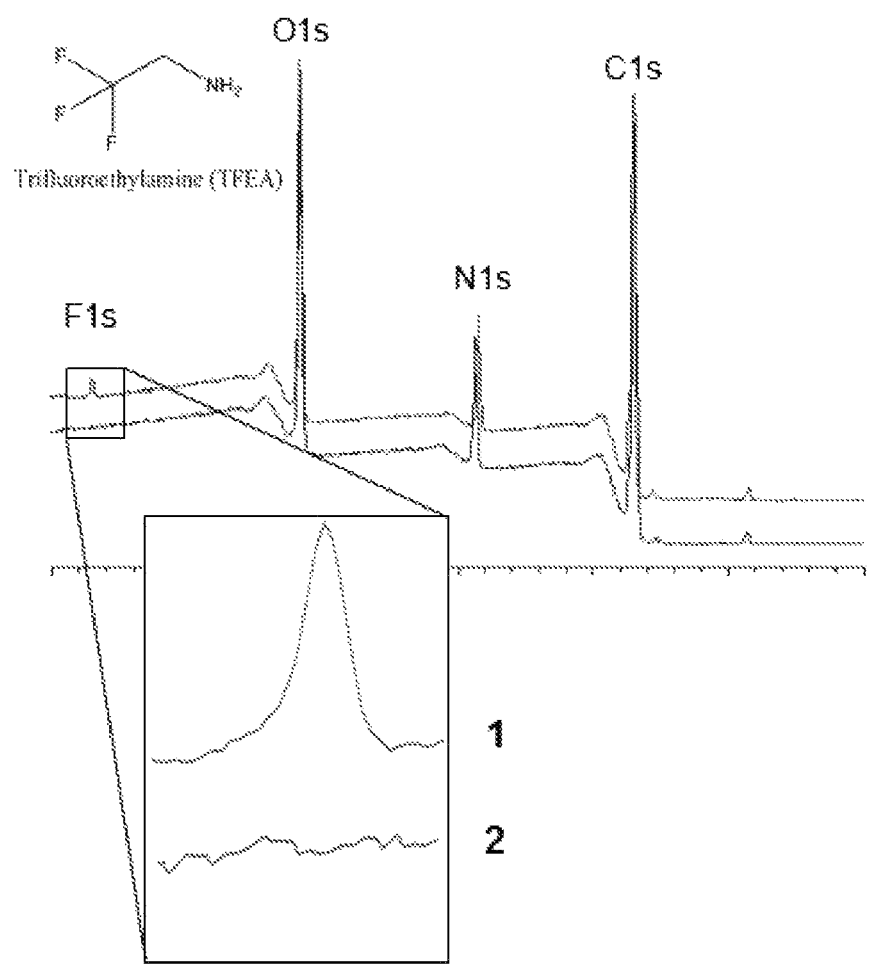
FIG. 21—XPS analysis of PEGDGE and PolyHPA-NH$_2$ coating following the incorporation of trifluoroethylamine (line 1) compared to untreated coating (TFEA) (line 2).

Due to the trifluoro group present on the TFEA molecule, the incorporation of this compound could be determined via XPS analysis. A comparison between the untreated and TFEA samples showed the incorporation the TFEA molecule into the coating (FIG. 21).

Example 4—Making of Polymeric Coatings Utilising a First Component and a Second Component (According to Examples 1-3), with Incorporation of a Complexed Bioactive Metal Ion In this example, the bioactive is a complex containing a metal ion, which is covalently bound to the crosslinked polymer architecture of the coating described in the present invention. The incorporation of metal ions such as Ag($^+$), Cu($^{2+}$), Bi($^{3+}$) etc., may be achieved by a complexation agent known to those familiar with the art. The complex comprises at least one suitable reactive group for covalent incorporation into the covalently crosslinked polymeric coating.

These complexes can be used advantageously particularly in antimicrobial applications. The use of metals, with metal ions being the active species, was commonplace until the discovery of antibiotics in the 1920s. At this point in time though the interest in metal ion based antimicrobial agents has been renewed due to the rapid rise in antibiotic resistance.

Example 5—Making of Polymeric Coatings Utilising a First Component and a Second Component (According to Examples 1-3), with Incorporation of Peptidomimetic In this example, the small molecule peptidomimetic provides highly specific binding to αvβ3 integrins (cell transmembrane receptors). After synthesis of this peptidomimetic according to A. G. Riches et al. (A. G. Riches, T. Cablewski, V. Glattauer, H. Thissen, L. Meagher, "Scalable Synthesis of an Integrin-Binding Peptide Mimetic for Biomedical Applications", Tetrahedron 68(46), 9448-9455, 2012) and the installation of an amine functional group, this small molecule was then used as the bioactive, comprising a suitable reactive group for covalent incorporation into the covalently crosslinked polymeric coating. The results demonstrate that human mesenchymal stem cells (hMSCs) bind specifically to spots printed using a microarray robot. In this example, a non-cell adhesive background was deposited first using a 2:1 PEG:DAP ratio followed by drying and incubation at 60° C. overnight. Subsequently, a microarray robot was used to deposit dots containing a 1:5 PEG:DAP ratio as well as the peptitomimetic at a concentration of 250 μM. The results as shown in FIG. 22, demonstrate the low cell attachment on the 2:1 PEG:DAP ratio used as a background coating and at the same time demonstrate the highly specific binding to the peptidomimetic incorporated into the polymer dots.

Figure 22:
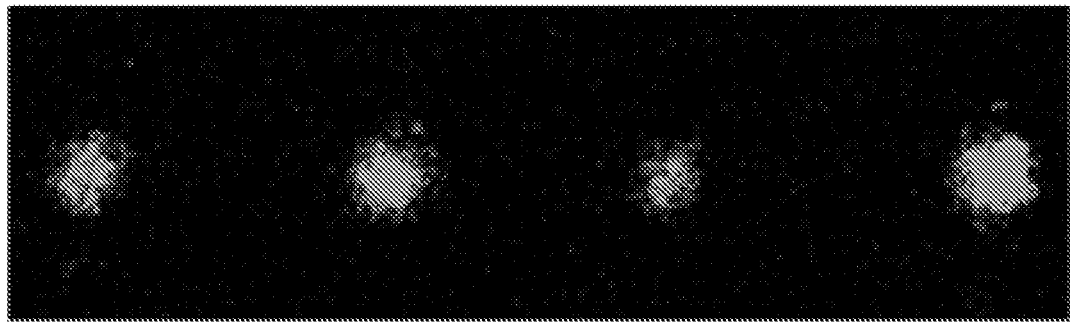
FIG. 22—Binding of human mesenchymal stem cells (stained with live/dead stain, Thermo Fisher) on PEGDAP spots containing a peptitomimetic deposited by a microarray.

FIG. 22 shows the binding of human mesenchymal stem cells (stained with live/dead stain, Thermo Fisher) on PEGDAP spots containing a peptitomimetic deposited by a microarray printer. The distance between the centre of spots was 750 μm, spot size was approximately 250 μm) on a low cell adhesive PEGDAP coating. A Nikon A1si confocal spectra system was used to capture this image.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for coating a substrate on at least one surface of the substrate, the method comprising:
    a) providing:
        the substrate, wherein the at least one surface of the substrate comprises a functional group selected from the group consisting of: amino groups, carboxylic groups, epoxide groups, vinyl groups, allyl groups, acrylate groups, acrylamide groups, siloxane groups, aldehyde groups, azide groups, alkyne groups, thiol groups, isocyanate groups, N-hydroxysuccinimide groups and maleimido groups;
        a First Component comprising at least two epoxide groups or at least two alkenyl groups;
        a Second Component comprising at least one amine group; and
    b) forming a covalently crosslinked polymer coating with the First Component and the Second Component, the polymer coating being covalently bound to the substrate,
wherein at least one bioactive agent comprising at least one suitable reactive group for incorporation into the covalently crosslinked polymer coating is introduced in step a), and wherein the at least one bioactive agent is covalently bound to: the substrate; or the First Component or the Second Component in the covalently crosslinked polymer coating.

2. The method according to claim 1, wherein the alkenyl groups are selected from the group consisting of: vinyl groups, allyl groups, acrylamide groups, acrylate groups, and mixtures thereof.

3. The method according to claim 1, wherein the First Component is a non-polymer compound selected from the group consisting of: glycerol diglycidyl ether, neopentyl glycol diglycidyl ether, glycerol triglycidyl ether, trimethylolpropane triglycidyl ether, trimethylolethane triglycidyl ether, and mixtures thereof.

4. The method according to claim 1, wherein the First Component is a polymer comprising at least two epoxide groups or at least two alkenyl groups, the polymer being selected from the group consisting of: a polyacrylamide, polyethylene glycols, polypropylene glycols, poly(dimethyl siloxanes), poly(vinyl alcohols), poly(acrylamides), poly(acrylates), poly(methacrylates), poly(methacrylamides), poly(vinyl pyrrolidone), poly(tetrahydrofurans), polylactic acid, polyglycolic acid, poly(L-lactide), poly(D,L-lactide) polyglycolic acid[polyglycolide], poly(L-lactide-co-D,L-lactide), poly(L-lactide-co-glycolide), poly(D, L-lactide-2-co-glycolide), co-glycolide), poly(glycolide-co-trimethylene carbonate), poly(D,L-lactide-co-caprolactone), poly(glycolide-co-caprolactone), polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, copolymers of polyhydroxybutyrate, poly(phosphazene), poly(phosphate ester), poly(amino acid), maleic anhydride copolymers, polyiminocarbonates, poly[(97.5% dimethyl-trimethylene carbonate)-co-(2.5% trimethylene carbonate)], poly(orthoesters), polyalkylene oxides, dextran, hydroxypropylmethylcellulose, polysaccharides, and copolymers or mixtures thereof.

5. The method according to claim 1, wherein the Second Component is a straight-chain or branched, linear or cyclic, aliphatic or aromatic hydrocarbon which comprises at least one amine group.

6. The method according to claim 1, wherein the Second Component is a non-polymer compound selected from the group consisting of: 1,2-diaminoethane, 1,2-diaminopropane, 1,3-diaminopropane, 1,3-diamino-2-propanol, 3,3'-diamino-N-methyldipropylamine, 1,4-diaminobutane, 1,3-diaminobutane, 1,2-diaminobutane, 1,5-diaminopentane, 1,4-diaminopentane, 1,3-diaminopentane, 1,2-diaminopentane, 1,5-diamino-2-methylpentane, 1,6-diaminohexane, 1,5-diaminohexane, 1,4-diaminohexane, 1,3-diaminohexane, 1,2-diaminohexane 1,12-dodecanediamine, 1,11-diamino-3,6,9-trioxaundecane, diethylenetriamine, isophoronediamine, and mixtures thereof.

7. The method according to claim 1, wherein the Second Component is a polymer comprising at least one amine group selected from the group consisting of: polyethylene glycols, polypropylene glycols, poly(dimethyl siloxanes), poly(vinyl alcohols), poly(acrylamides), poly(acrylates), poly(methacrylates), poly(methacrylamides), poly(vinyl pyrrolidone), poly(tetrahydrofurans), polylactic acid, polyglycolic acid, poly(L-lactide), poly(D,L-lactide) polyglycolic acid[polyglycolide], poly(L-lactide-co-D,L-lactide), poly(L-lactide-co-glycolide), poly(D, L-lactide-2-co-glycolide), co-glycolide), poly(glycolide-co-trimethylene carbonate), poly(D,L-lactide-co-caprolactone), poly(glycolide-co-caprolactone), polydioxanone, polypropylene fumarate, poly(ethyl glutamate-co-glutamic acid), poly(tert-butyloxy-carbonylmethyl glutamate), polycaprolactone, polycaprolactone co-butylacrylate, polyhydroxybutyrate, zwitterionic polymers, and copolymers or mixtures thereof.

8. The method according to claim 1:
    further comprising the addition of a compound comprising a photoreactive group in step a); or
    wherein at least one of the First Component or the Second Component further comprises at least one photoreactive group.

9. The method according to claim 1, wherein the First Component and the Second Component are in a ratio of about 4:1 to about 1:4.

10. The method according to claim 1, wherein the at least one bioactive agent is selected from the group consisting of: pharmaceutical drugs; compounds which act as quorum sensing inhibitors; metal complexing compounds, antimicrobial compounds; amino acids; peptides; peptidomimetics; synthetic analogues of natural bioactive molecules; synthetic peptide mimetics; proteins; receptor-targeting ligands; gene silencing agents; ambisenses; antisenses; an RNA; a living cell; antibiotics; and mixtures thereof.

11. The method according to claim 1, wherein the substrate is selected from the group consisting of: plastics, metals, ceramics, woven materials, silicon materials, and combinations thereof.

12. The method according to claim 1, wherein the polymer coating is antimicrobial or antifouling.

13. The method according to claim 1, wherein the substrate is in the form of a medical device to which the polymer coating is applied, wherein the medical device is selected from the group consisting of: surgical, medical or dental instruments, blood oxygenators, pumps, tubing, wiring, electrodes, contraceptive devices, feminine hygiene products, endoscopes, grafts, stents, pacemakers, implantable cardioverter-defibrillators, cardiac resynchronisation therapy devices, ventricular assist devices, heart valves, catheters including vascular, urinary, neurological, peritoneal, and interventional catheters, shunts, wound drains, dialysis membranes, infusion ports, cochlear implants, endotracheal tubes, guide wires, fluid collection bags, sensors, wound treatments including dressings, bandages, sutures, cell scaffolds, bone cements and particles, ophthalmic devices, orthopaedic devices including hip implants, knee implants, spinal implants, screws, plates, rivets, rods, intramedullary nails, bone cements, artificial tendons, and other prosthetics or fracture repair devices, dental implants, breast implants, penile implants, maxillofacial implants, cosmetic implants, valves, appliances, scaffolding, suturing material, needles, hernia repair meshes, tension-free vaginal tape and vaginal slings, tissue regeneration or cell culture devices.

* * * * *